(12) United States Patent
Lundqvist

(10) Patent No.: US 9,186,454 B2
(45) Date of Patent: Nov. 17, 2015

(54) ATTACHMENT DEVICE AND METHOD

(75) Inventor: Kristian Lundqvist, The Gap (AU)

(73) Assignee: The Lundqvist Family Trust, The Gap, Queensland (AU)

( * ) Notice: Subject to any disclaimer, the term of this patent is extended or adjusted under 35 U.S.C. 154(b) by 1075 days.

(21) Appl. No.: 12/087,853

(22) PCT Filed: Jan. 15, 2007

(86) PCT No.: PCT/AU2007/000031
§ 371 (c)(1),
(2), (4) Date: Jul. 16, 2008

(87) PCT Pub. No.: WO2007/082333
PCT Pub. Date: Jul. 26, 2007

(65) Prior Publication Data
US 2009/0054843 A1 Feb. 26, 2009

(30) Foreign Application Priority Data

Jan. 18, 2006 (AU) ................. 2006900247
Sep. 27, 2006 (AU) ................. 2006905336

(51) Int. Cl.
*A61M 5/14* (2006.01)
*A61M 25/02* (2006.01)

(52) U.S. Cl.
CPC ........... *A61M 5/1418* (2013.01); *A61M 5/1415* (2013.01); *A61M 25/02* (2013.01); *A61M 2005/1416* (2013.01); *A61M 2025/024* (2013.01)

(58) Field of Classification Search
CPC . A61M 5/1418; A61M 5/1415; A61M 25/02; A61M 2005/1416; A61M 2025/024

USPC .................... 604/103.03, 174, 175, 177, 178; 606/108

See application file for complete search history.

(56) References Cited

U.S. PATENT DOCUMENTS

| | | | |
|---|---|---|---|
| 4,164,943 | A | 8/1979 | Hill et al. |
| 4,397,647 | A | 8/1983 | Gordon |
| 4,683,895 | A | 8/1987 | Pohndorf |

(Continued)

FOREIGN PATENT DOCUMENTS

| | | |
|---|---|---|
| EP | 0116526 | 8/1984 |
| EP | 0567029 A1 | 10/1993 |

(Continued)

OTHER PUBLICATIONS

International Search Report for PCT/AU2007/000031 dated Apr. 29, 2007.

(Continued)

*Primary Examiner* — Emily Schmidt
*Assistant Examiner* — Lauren M Peng
(74) *Attorney, Agent, or Firm* — Klarquist Sparkman, LLP

(57) ABSTRACT

An attachment device for anchoring a medical device to a patient has, in one aspect, an anchoring portion for attachment to the tissue of a patient by operation of at least one piercing member which in use is deployed for anchoring the device to the tissue of a patient. Alternatively, or additionally, in a further aspect an attachment device comprises a holding part, for holding an elongate object, which is operable between an open position which allows removal of the elongate object and a closed position adapted to securely retain the elongate object. The holding part may include first and second holding portions, for respectively engaging first and second surface parts of the elongate object.

12 Claims, 81 Drawing Sheets

(56) References Cited

U.S. PATENT DOCUMENTS

| | | | |
|---|---|---|---|
| 5,267,970 A | 12/1993 | Chin et al. | |
| 5,354,282 A | 10/1994 | Bierman | |
| 5,382,239 A | 1/1995 | Orr et al. | |
| 5,470,321 A * | 11/1995 | Forster | A61M 25/02 128/DIG. 26 |
| 5,540,648 A * | 7/1996 | Yoon | 600/114 |
| 5,683,378 A * | 11/1997 | Christy | 606/1 |
| 5,755,225 A | 5/1998 | Hutson | |
| 5,800,402 A | 9/1998 | Bierman | |
| 6,387,076 B1 | 5/2002 | Landuyt | |
| 6,572,587 B2 * | 6/2003 | Lerman | A61M 25/02 604/174 |
| 6,572,588 B1 | 6/2003 | Bierman et al. | |
| 2003/0167055 A1 | 9/2003 | Kolata et al. | |
| 2004/0087996 A1 | 5/2004 | Gambale et al. | |
| 2004/0199122 A1 | 10/2004 | Bierman et al. | |
| 2004/0204684 A1 | 10/2004 | Bierman | |
| 2004/0254536 A1 | 12/2004 | Conlon et al. | |
| 2005/0054985 A1 | 3/2005 | Mogg | |
| 2005/0256459 A1 * | 11/2005 | Howard et al. | 604/174 |
| 2005/0283119 A1 * | 12/2005 | Uth et al. | 604/175 |

FOREIGN PATENT DOCUMENTS

| | | |
|---|---|---|
| WO | WO84/03217 | 8/1984 |
| WO | WO01/68180 | 9/2001 |
| WO | WO03/092781 | 11/2003 |

OTHER PUBLICATIONS

European Search Report and Opinion for PCT/AU2007000031 dated Jul. 13, 2010.

* cited by examiner

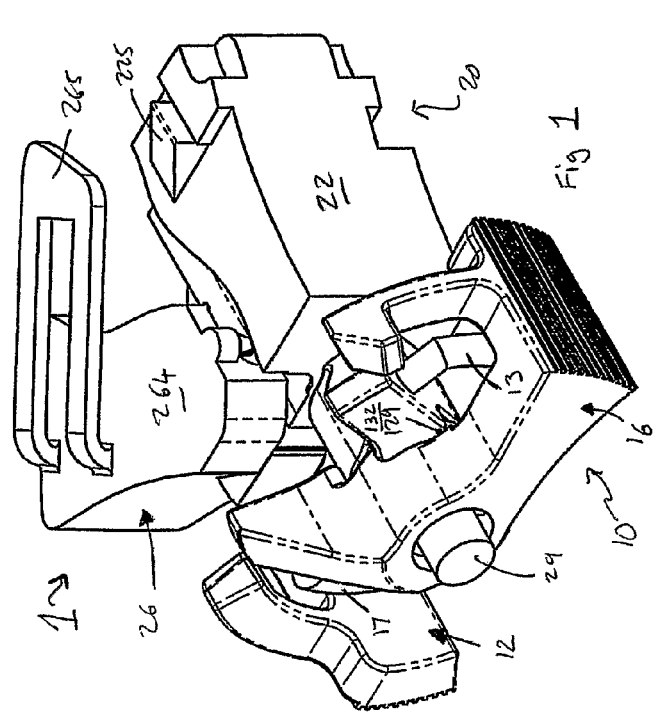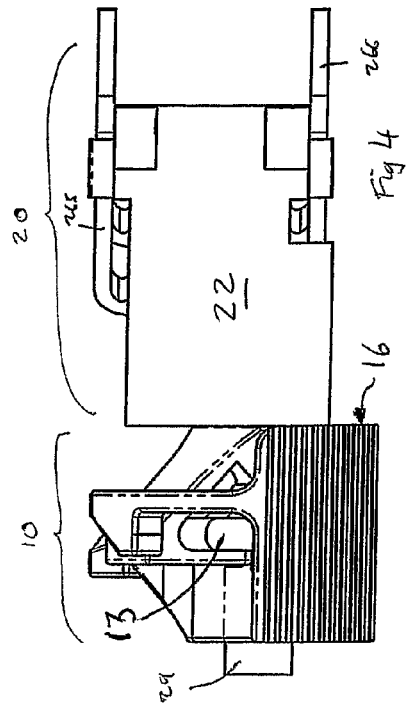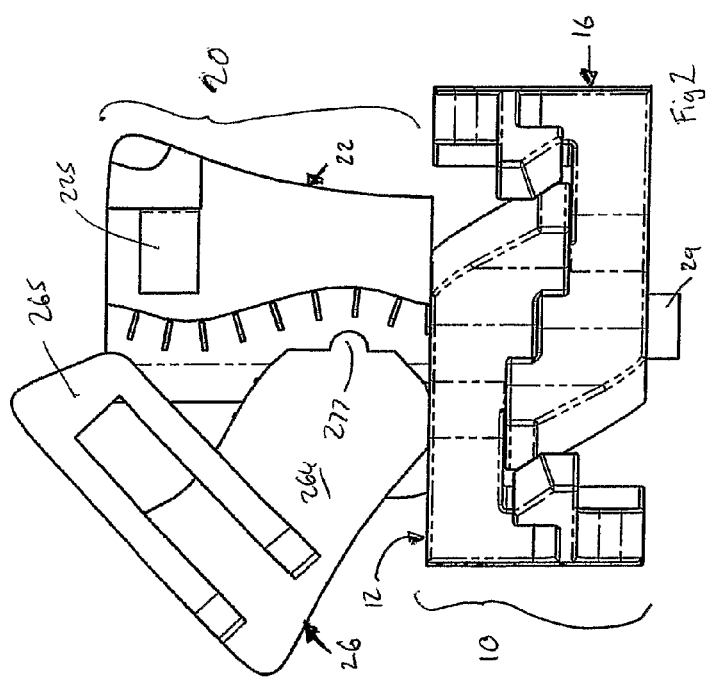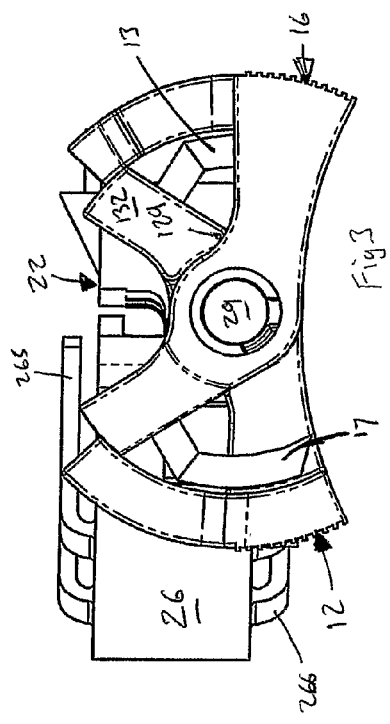

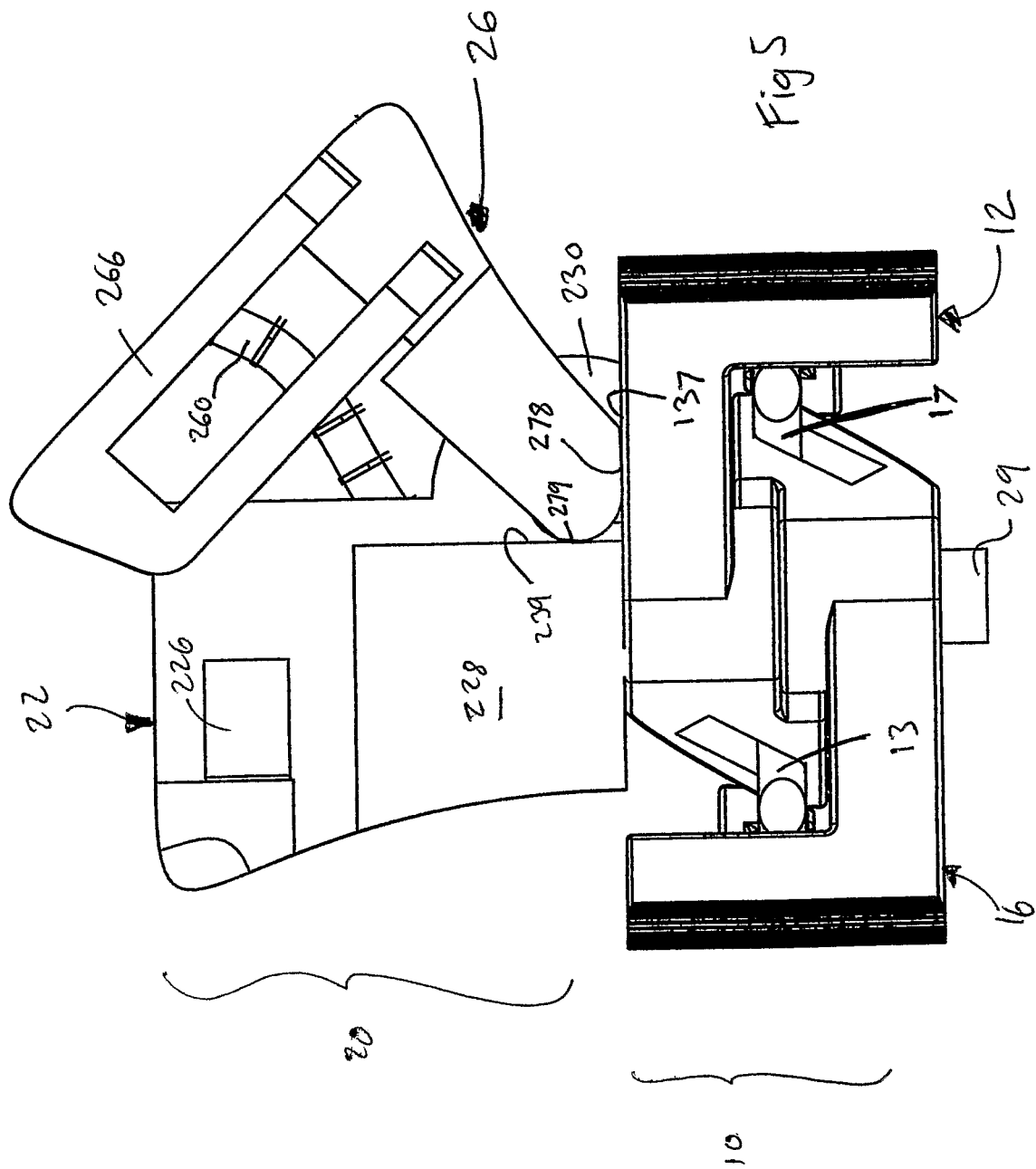

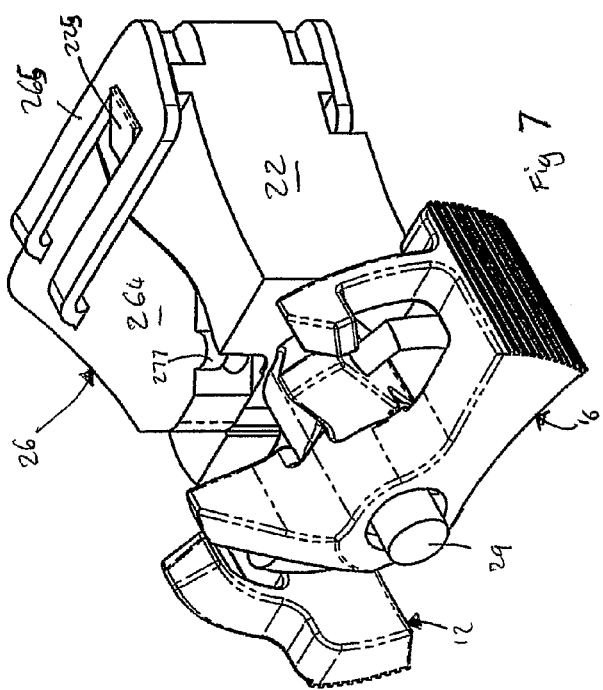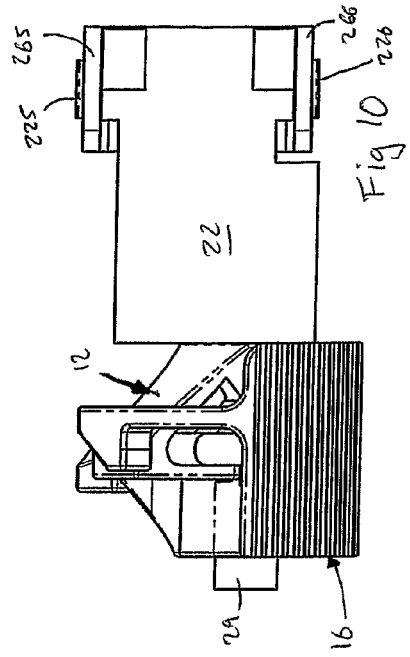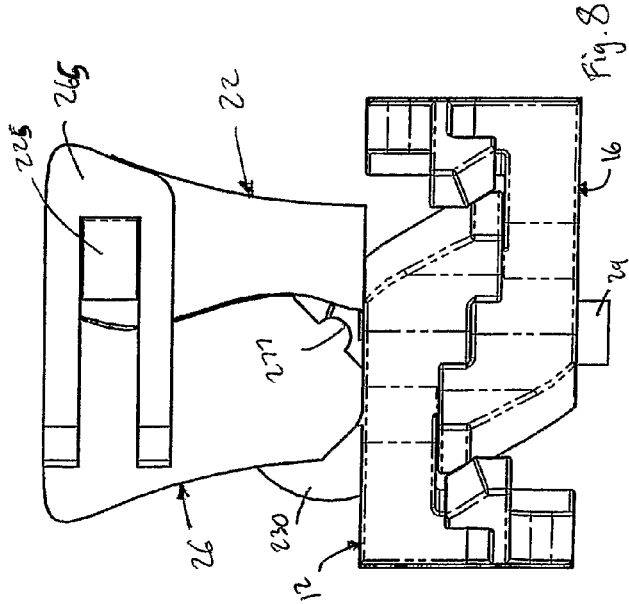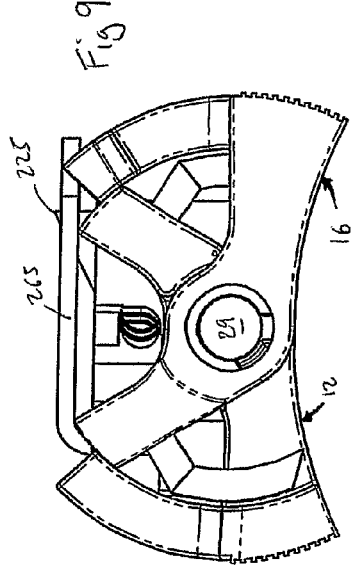

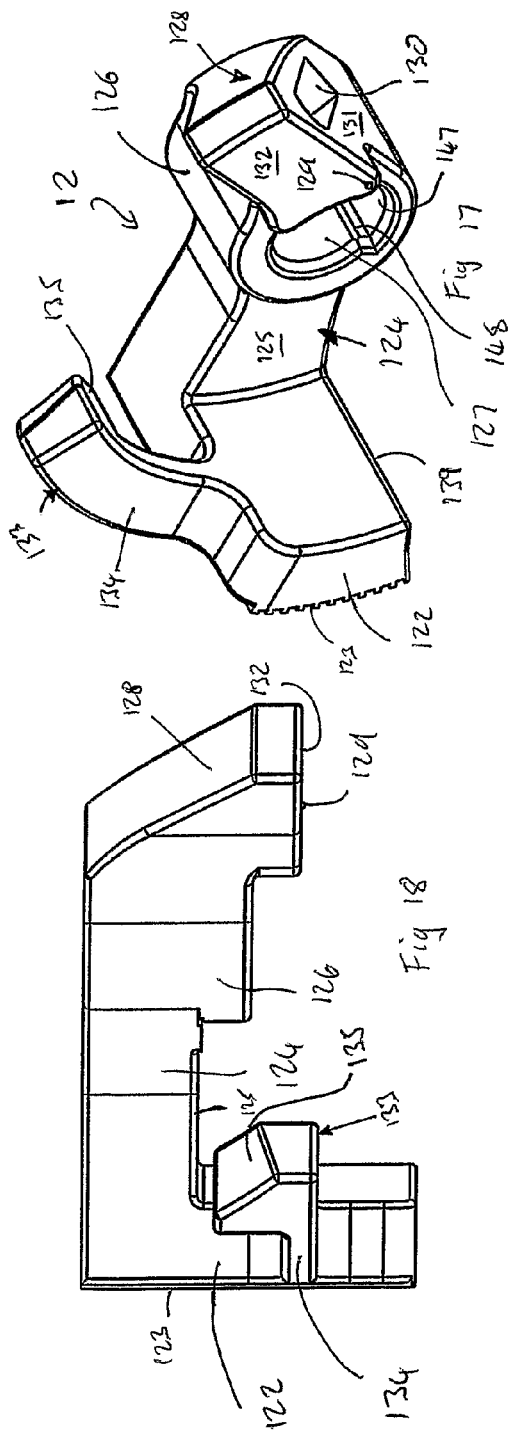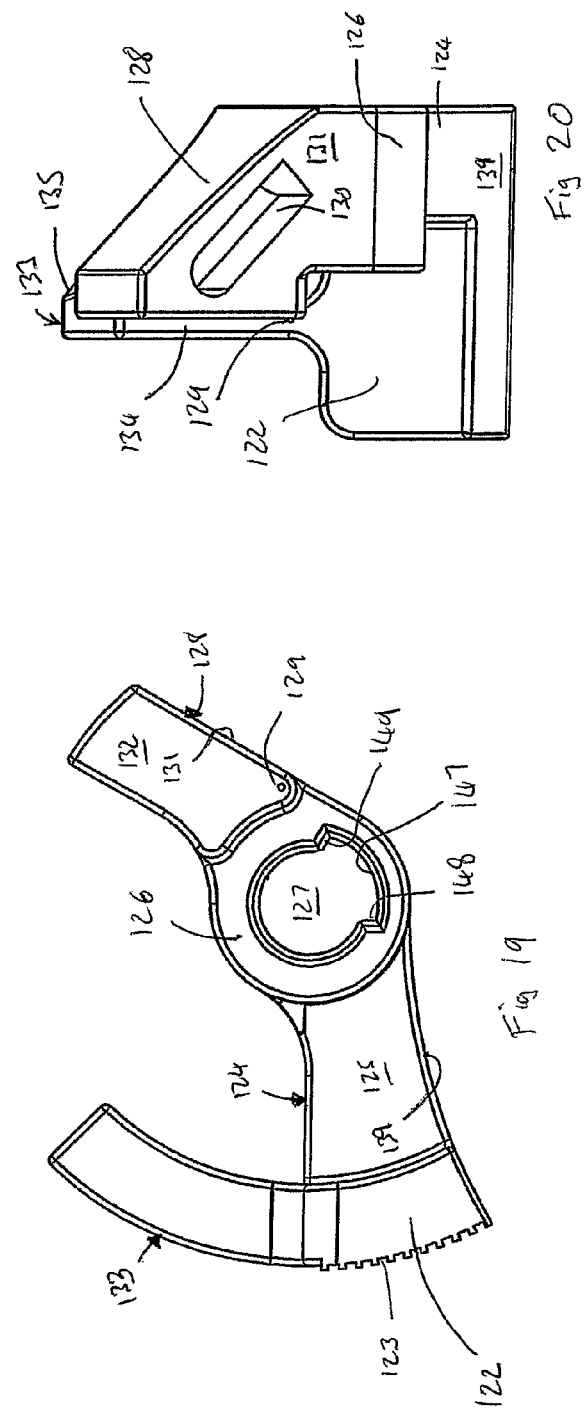

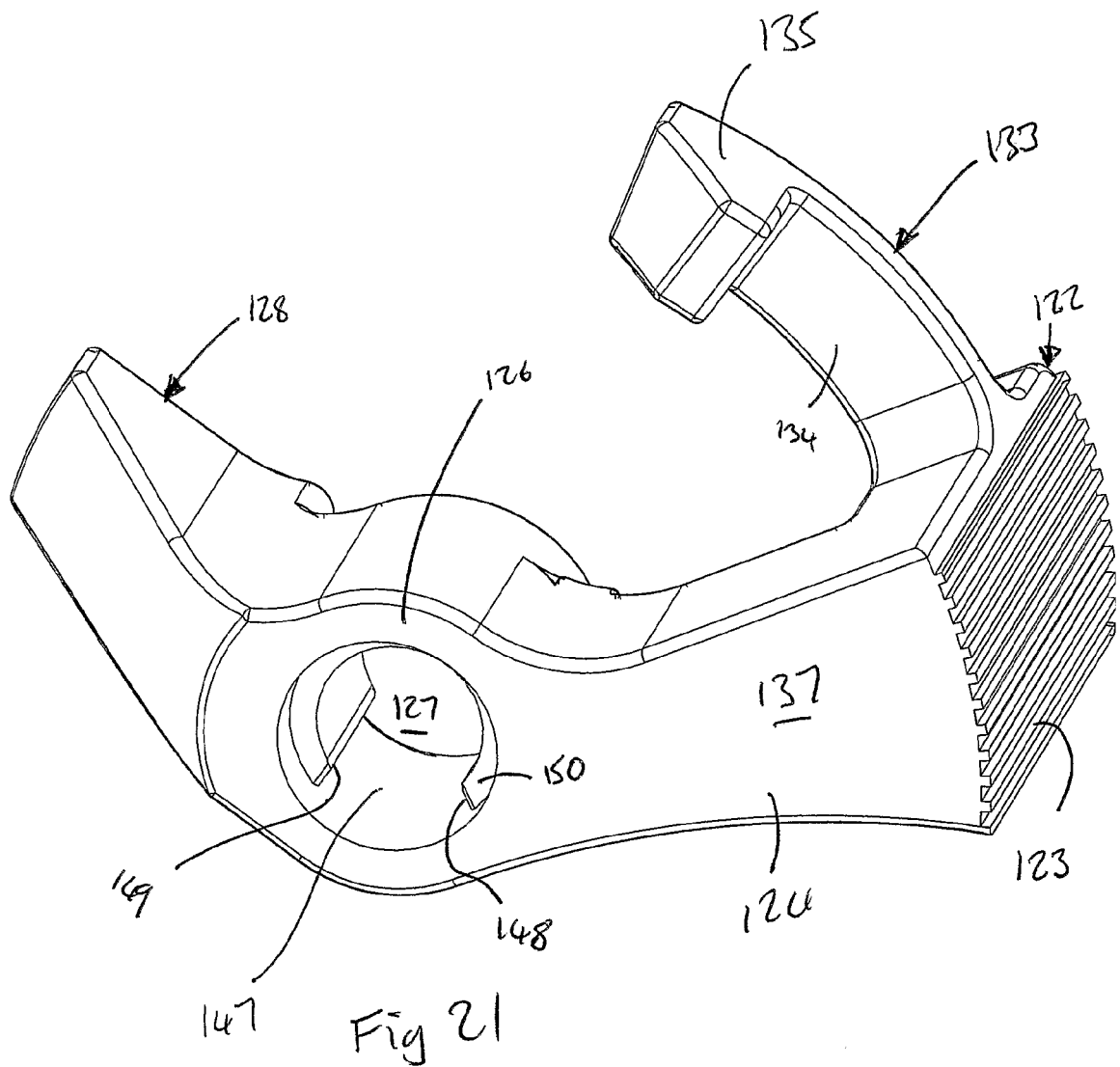

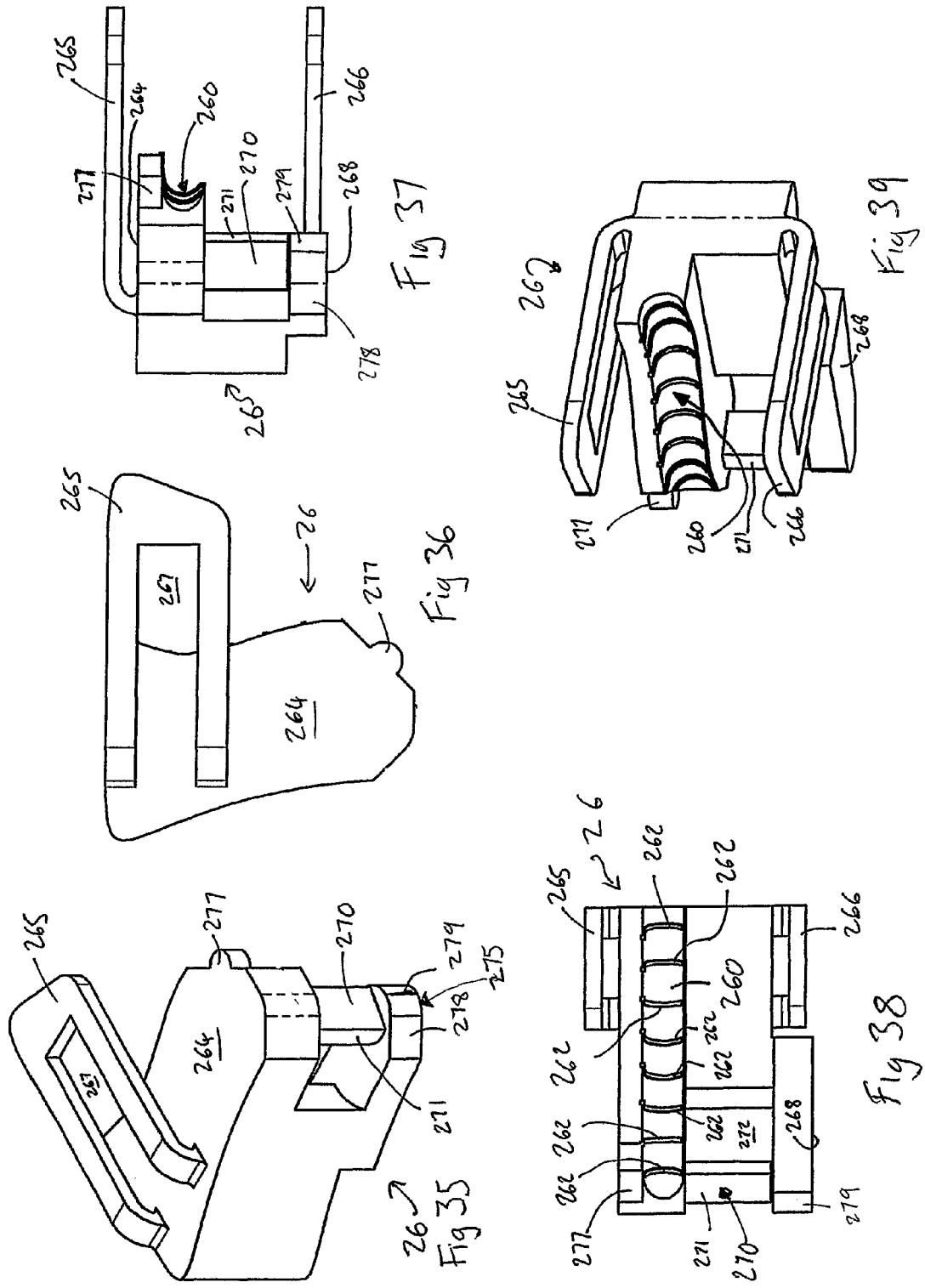

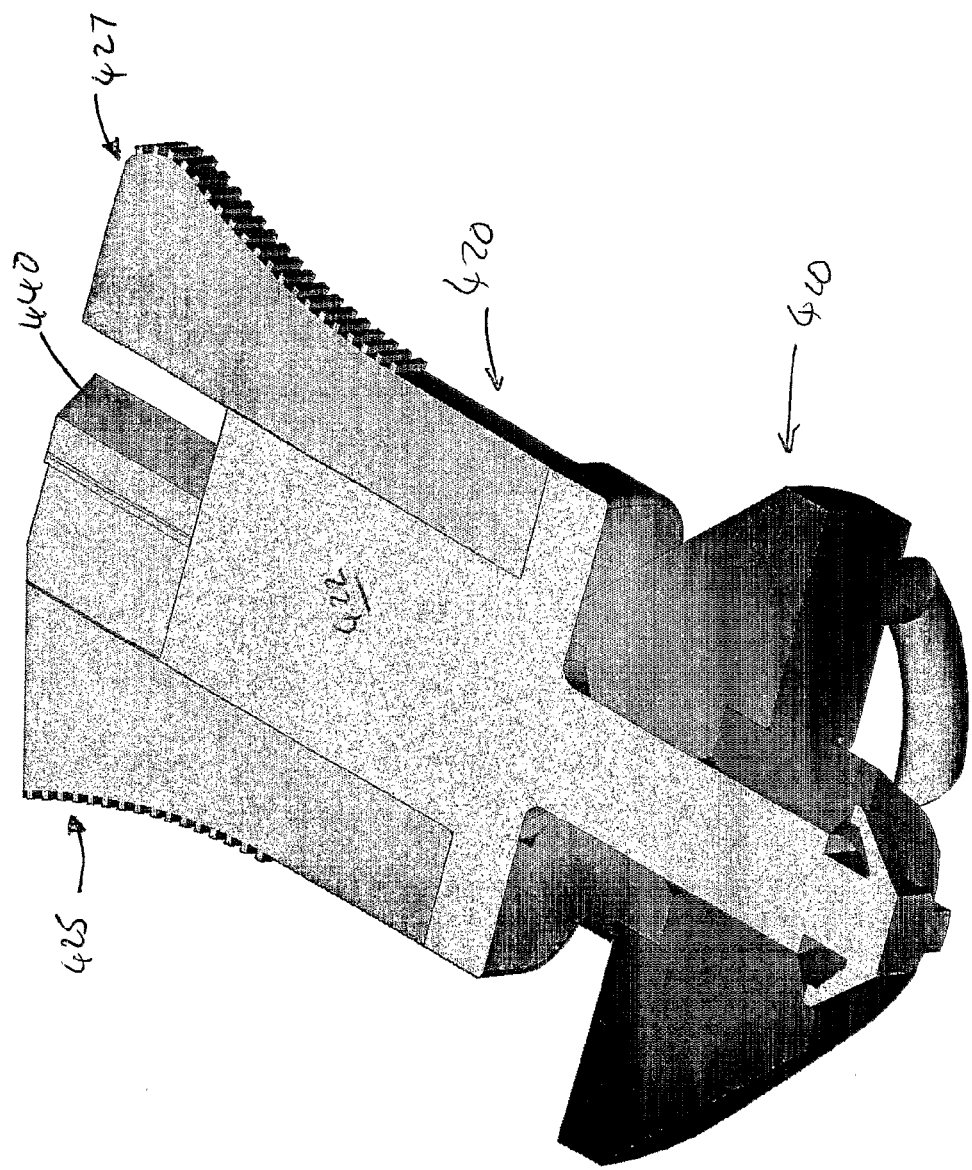

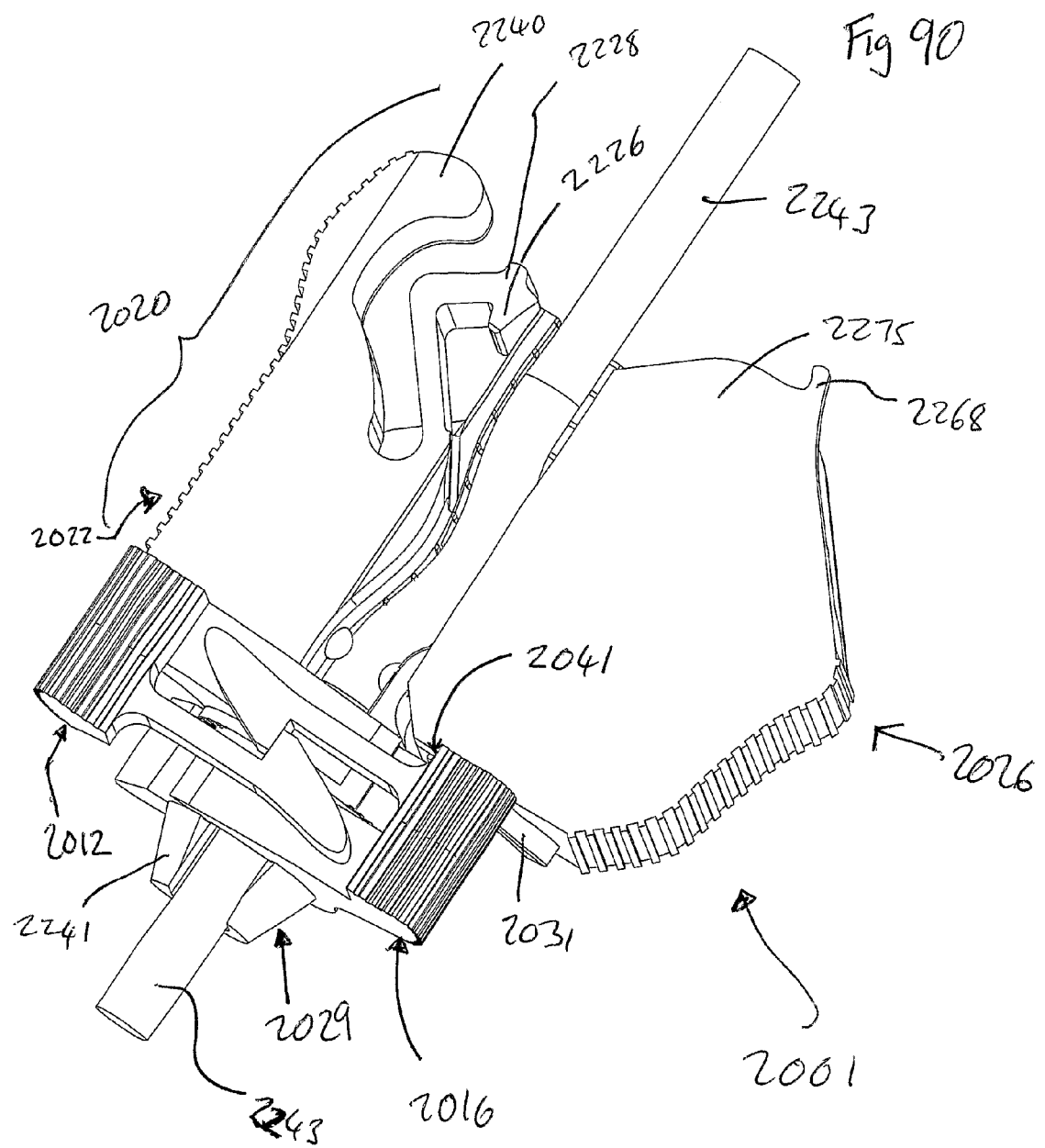

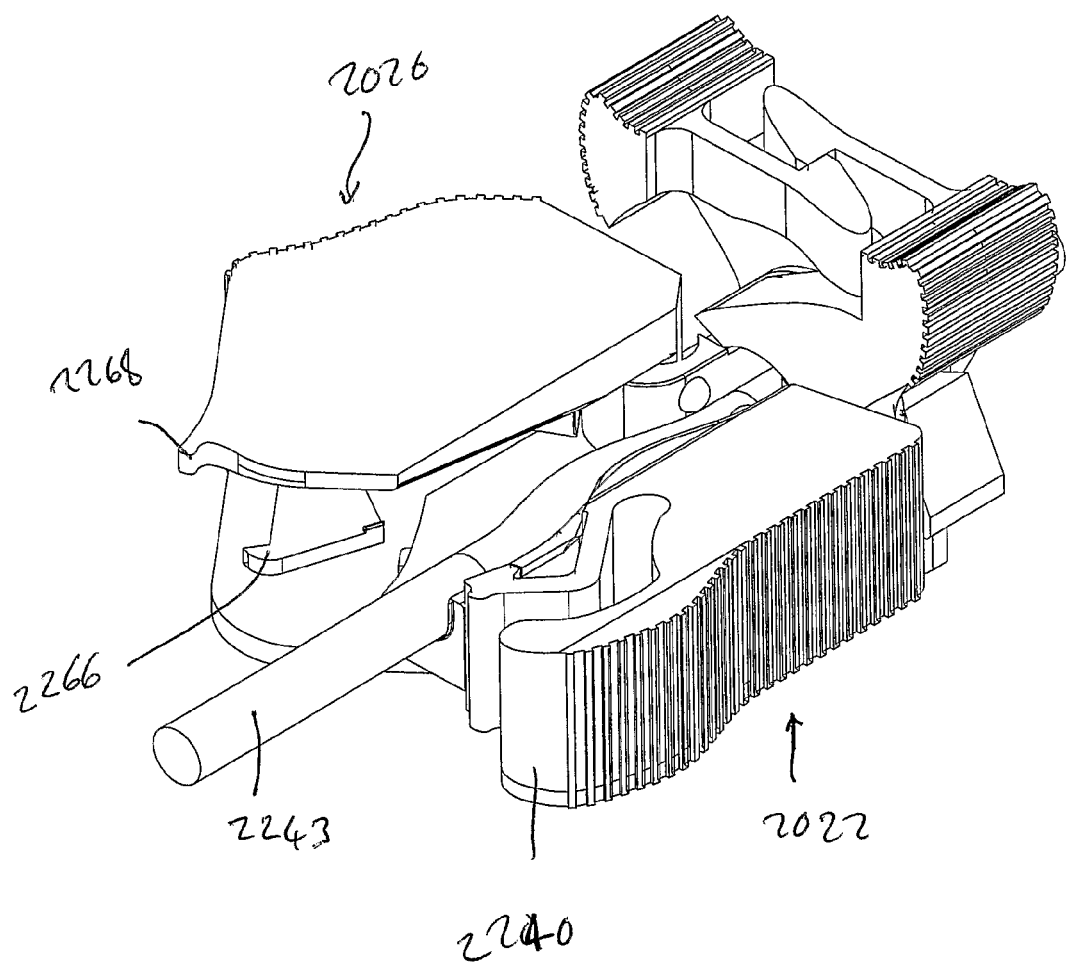

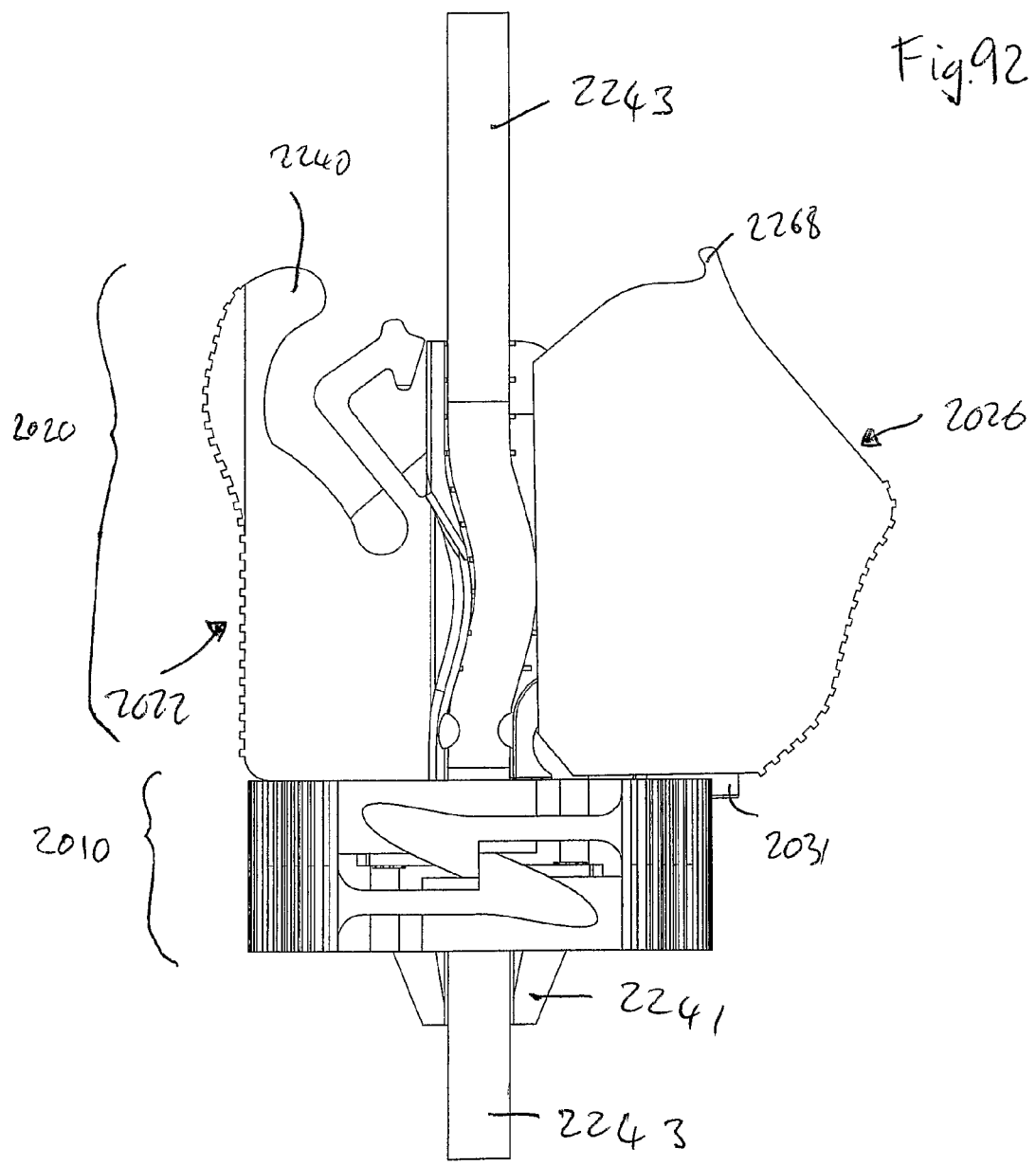

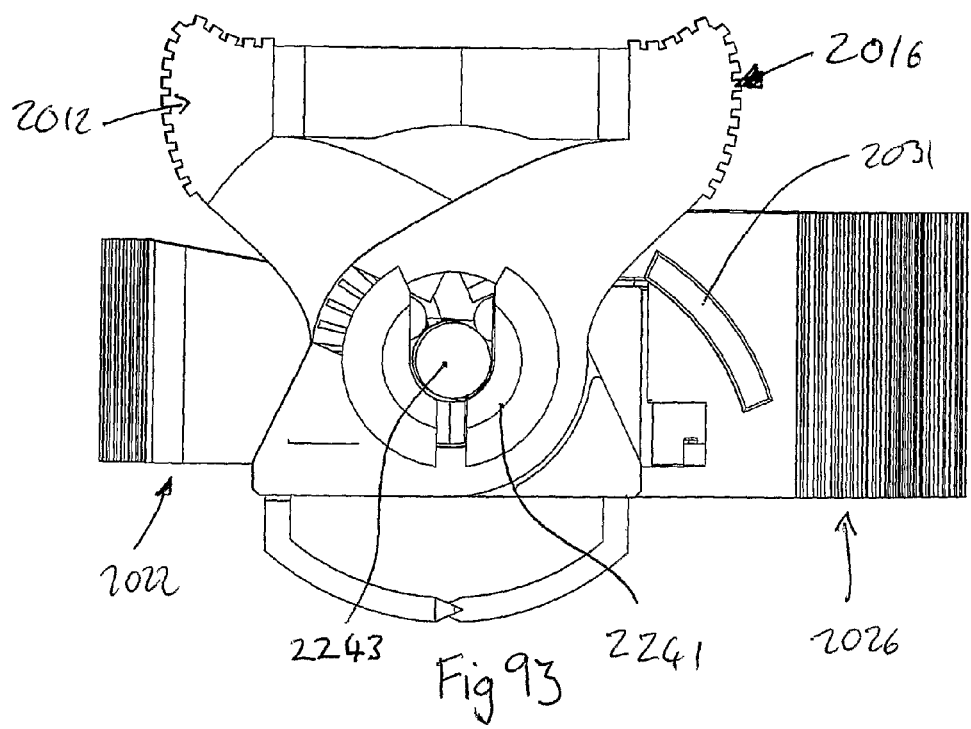
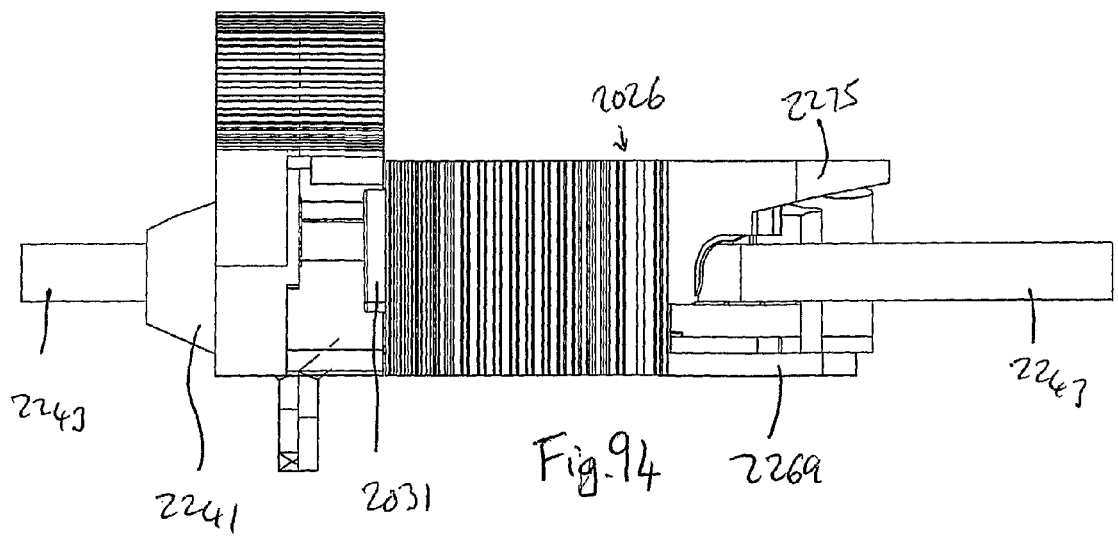

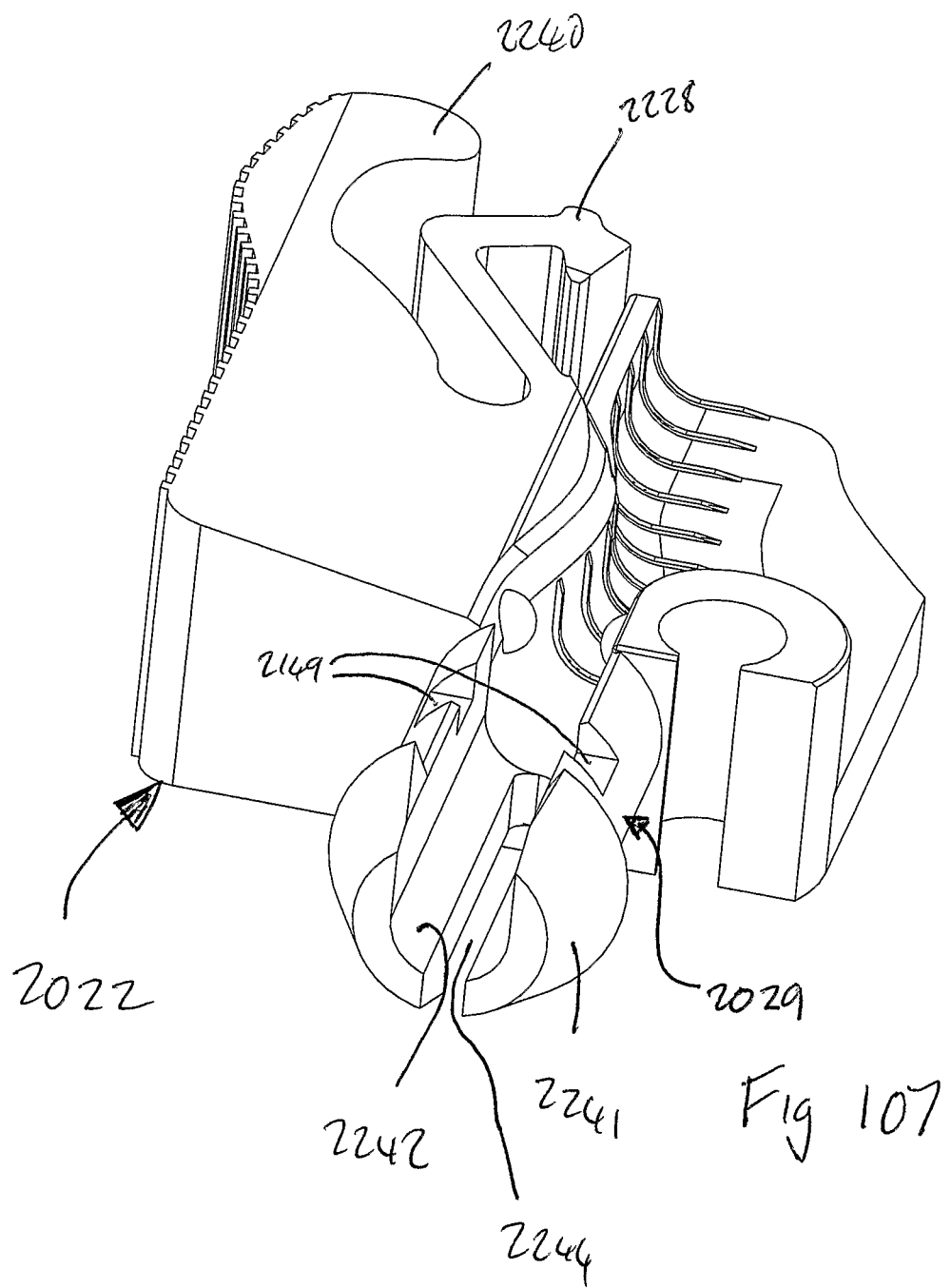

ATTACHMENT DEVICE AND METHOD

FIELD OF THE INVENTION

The present invention relates to an attachment device and method and especially, but not exclusively to an attachment device and method for use in securely attaching a tube such as a catheter tube, or the tube of a surgical drain, to a patient.

BACKGROUND OF THE INVENTION

For many medical applications it is important that tubes, such as catheter or surgical drain tubes, are securely attached relative to a patient. The consequences of accidental movement of such a tube can range from discomfort (for example in the case of small peripheral vein catheters) to fatal trauma (for example in the case of main line catheters).

A typical method used to secure a catheter is to use a plastic base which includes two apertures and a holding clip for a catheter tube and to sew or suture the base to the patient, using a needle and thread by passing the needle through the apertures and through the skin and/or other tissue of the patient. This is a relatively complex and time consuming operation and is prone to error. For example the thread may be sewn too tight, causing unnecessary tissue damage or too loose, resulting in an inadequately secured catheter. Furthermore, there is a significant risk of needle stick injuries, which are a serious health hazard due to the widespread existence of diseases which are transmissible via bodily fluids.

One approach to avoiding needle stick injuries has been to dispense with the use of sutures and to secure a base of an attachment device to the skin of a patient using an adhesive. However, this approach does have accompanying disadvantages. The adhesive may inadequately fix the catheter, or be effective for only an inadequately short time. Hair on the skin and/or occurrence of perspiration may result in a significant loss of adhesion, or the adhesive may suffer from reduced adhesion over time due to oils excreted by the skin, or other factors. The adhesive may intrinsically provide inadequate adhesion. If a very strong adhesive is used, removal of the attachment device may result in tearing the skin. The adhesive may provoke an irritant and/or allergic reaction as may a cleaning agent (typically benzoin or tinc benz) used to clean the skin prior to application of the adhesive.

Known attachment devices have employed various means for securing the medical tube to the attachment device, but at least some such means are less than optimally convenient in use. For example, some such devices do not allow convenient attachment and release of the tube when the attachment device is securely attached to the patient, and some require the use of separate elements which must be attached to the tube prior to securing the tube to the main part of the attachment device.

There is therefore a need for an improved, or at least alternative, attachment device and method for use in securing catheter tubes and/or other medical devices to a patient.

SUMMARY OF THE INVENTION

According to a first aspect of the present invention, there is provided an attachment device for anchoring to a patient, the attachment device comprising an anchoring portion comprising:

a first piercing member for anchoring the device by insertion of at least a pointed end part of the first piercing member into the tissue of a patient, the first piercing member being attached to and supported by a first support body;

a second piercing member for anchoring the device by insertion of at least a pointed end part of the second piercing member into the tissue of a patient, the second piercing member being attached to and supported by a second support body;

wherein the first and second support bodies are moveable relative to each other between an open position of the anchoring portion in which the anchoring portion is inoperative and a closed position of the anchoring portion for anchoring the device to the tissue of a patient.

Preferably, in the open position of the anchoring portion the first support body provides a first shielding portion which shields at least the pointed end part of the second piercing member against inadvertent contact with another object.

Preferably, in the open position of the anchoring portion, the second support body provides a second shielding portion which shields at least the pointed end part of the first piercing member against inadvertent contact with another object.

Preferably, in use, the open position of the anchoring portion corresponds to the piercing members being in retracted positions.

Preferably, in use, the closed position corresponds to the piercing members being extended from the device so that they extend into the skin or other tissue of a patient to anchor the device.

Preferably the first shielding portion comprises a part of the first support body which is adapted to contact the tissue of a patient when the anchoring portion is in its open position, and which is, in use, retracted away from the tissue of a patient when the anchoring portion is in its closed position.

Preferably the second shielding portion comprises a part of the second support body which is adapted to contact the tissue of a patient when the anchoring portion is in its open position, and which is, in use, retracted away from the tissue of a patient when the anchoring portion is in its closed position.

Preferably the first support body comprises a control portion via which a force can be applied to effect relative movement of the first and second support bodies.

Preferably the second support body comprises a control portion via which a force can be applied to effect relative movement of the first and second support bodies.

Preferably, the anchoring portion is operable from its open position to its closed position by drawing together control portions of the first and second support bodies.

Preferably, the anchoring portion is adapted to allow the control portions of the first and second support bodies to be manually drawn together without the use of tools.

Preferably, the anchoring portion is adapted to allow the control portions of the first and second support bodies to be manually drawn together by the use of a thumb tip and finger tip of a user.

Preferably, in use, drawing together of the control portions of the first and second support bodies comprises drawing each control portion away from the tissue of the patient to which the attachment device is being anchored.

Preferably, in use, drawing together of the control portions of the first and second support bodies comprises rotating the first and second support bodies in opposite directions, about a common axis.

In one embodiment the device is adapted to retain a tube of a medical device substantially coincident with said axis.

The device may be adapted to retain said tube of a medical device such that said tube passes though the first and second support bodies.

The device may be adapted to retain said tube of a medical device such that said tube passes though the first and second support bodies substantially along the axes of rotation thereof.

Preferably the first shielding portion comprises a part of the control portion of the first support body.

Preferably the first shielding portion comprises a tissue contact surface part of the control portion of the first support body.

Preferably the second shielding portion comprises a part of the control portion of the second support body.

Preferably the second shielding portion comprises a tissue contact surface part of the control portion of the second support body.

Preferably the first support body comprises a support portion for connection to, and support of, the first piercing member.

Preferably the second support body comprises a support portion for connection to, and support of, the second respective piercing member.

Preferably the first and second support bodies are relatively pivotably coupled.

Preferably the first support body comprises a first coupling portion for pivotable coupling to the second support body.

Preferably the first coupling portion is at a generally central portion of the first support body.

Preferably the first coupling portion is provided generally between the control portion and the support portion of the first support body.

Preferably the first coupling portion is provided with a cavity adapted to receive and rotate relative to a coupling member.

Preferably the second support body comprises a second coupling portion for pivotable coupling to the first support body.

Preferably the second coupling portion is at a generally central portion of the second support body.

Preferably the second coupling portion is provided generally between the control portion and the support portion of the second support body.

Preferably the second coupling portion is provided with a cavity adapted to receive and rotate relative to a coupling member.

Preferably the attachment device further comprises at least one body element.

Preferably the body element is provided with the said coupling member for receipt in, and coupling to, cavities in the first and second support bodies. The body element may be provided with a base surface for contacting the tissue of the patient when the attachment device is attached to said patient.

In an alternative embodiment the coupling member can be part of the coupling portion of one of the support bodies, which extends from that support body and into a cavity in the other support body.

Preferably the attachment device comprises limiting means to limit relative rotation of the first and second support bodies.

Preferably the limiting means comprises one or more abutment portions on the first coupling portion.

Preferably the limiting means comprises one or more abutment portions on the second coupling portion.

Preferably the limiting means comprises one or more abutment portions on the coupling member.

In one embodiment the limiting means comprises a recess with limited circumferential extent in the internal surface of the cavity of at least one coupling portion, and a projection on the coupling member which, in use is located in the recess. In another embodiment the limiting means comprises a recess with limited circumferential extent in the coupling member, and a projection on an internal surface of at least one coupling portion which, in use, is locatable in the recess.

Preferably the coupling member comprises retention means, for retaining at least one support body thereon.

Preferably the attachment device comprises an anchoring portion locking means for locking the anchoring portion in its closed position.

Preferably the anchoring portion locking means is adapted to lock the anchoring portion in its closed position automatically when the anchoring portion is operated to its closed position.

Preferably the anchoring portion locking means comprises complementary first and second locking portions.

Preferably the first and second locking portions are provided, respectively, on the first and second support bodies.

In one embodiment, the anchoring portion locking means is substantially secure against manual unlocking without tools. In this case, the anchoring portion locking means is adapted to be unlocked by use of a tool.

In an alternative embodiment, the anchoring portion locking means is adapted to be unlockable, manually, without use of a tool. In such an embodiment it is, of course, important that the device is designed and/or used such that there is little or no likelihood of inadvertent opening of the anchoring portion.

Preferably the anchoring portion locking means is adapted to be unlocked by insertion of a tool between the complementary first and second locking portions.

Preferably the attachment device comprises anchoring portion retaining means for retaining the anchoring portion in its open position.

Preferably the anchoring portion retaining means comprises an irregularity on at least one of two slidably engageable surfaces of the attachment device.

Preferably the irregularity is a projection.

Preferably at least one of said two slidably engageable surfaces is a surface of one of the support bodies.

Preferably said two slidably engagable surfaces are surfaces of the respective first and second support bodies.

Preferably the anchoring portion retaining means is adapted to prevent inadvertent closure of the anchoring portion.

Preferably the anchoring portion retaining means is adapted to prevent closure of the anchoring portion when a force less than a predetermined force is applied to close the device, but to allow closure of the anchoring portion when a force greater than a predetermined force is applied to close the device.

Preferably the predetermined force is of a magnitude that can be applied to the device by the grip of a finger and thumb by a single hand of a user.

Preferably the predetermined force is less than 30 Newtons.

The attachment device may comprise an anchoring portion restraining means for locking the anchoring portion in its open position.

Preferably the anchoring portion restraining means comprises at least one restraining element adapted to prevent operation of the anchoring portion from its open position to its closed position.

Preferably the at least one restraining element is operable between a first position in which it locks the anchoring portion in its open position, and a second position in which it does not lock the anchoring portion in its open position.

Preferably the at least one restraining element is adapted to prevent relative movement of the first and second support bodies.

There may be provided at least first and second restraining elements, the first restraining element being adapted to prevent movement of the first support body from the open position to the closed position of the anchoring portion, and the second restraining element being adapted to prevent movement of the second support body from the open position to the closed position of the anchoring portion. In one alternative there may be a single restraining element, a first part of which is adapted to prevent movement of the first support body from the open position to the closed position of the anchoring portion, and a second part of which is adapted to prevent movement of the second support body from the open position to the closed position of the anchoring portion.

The at least one restraining element is preferably provided on a moveable element of the attachment device which is moveable relative to the anchoring portion to operate the at least one restraining element between the first position in which it locks the anchoring portion in its open position, and the second position in which it does not lock the anchoring portion in its open position. In an alternative embodiment there is provided a moveable element of the attachment device which is moveable relative to the anchoring portion, but which does not operate a restraining element between a first position in which it locks the anchoring portion in its open position, and a second position in which it does not lock the anchoring portion in its open position.

Preferably the moveable element forms part of a holding means which is for holding an element in order to attach it to the attachment device.

Preferably the holding means comprises a first holding portion for engaging a first surface part of an elongate object and a second holding portion for engaging a second surface part of an elongate object, the first and second holding portions being mutually relatively movable, between an open position which allows removal of said elongate object and a closed position adapted to securely retain said elongate object.

Preferably, the moveable element comprises a holding portion of the holding means.

Preferably, when the moveable element is in a first position, preferably corresponding the holding means being open, the restraining element is in the first position in which it locks the anchoring portion in its open position.

Preferably, when the moveable element is in a second position, preferably corresponding the holding portion being closed, the restraining element is in the second position in which it does not lock the anchoring portion in its open position.

Further shielding portions may be provided to shield one or both of the said piercing members against inadvertent contact with another object when the anchoring portion is in its open position.

A shielding portion may be provided by a base surface of the attachment device.

Said base surface may be a base surface of an element of a holding portion of the device.

Said base surface may be a base surface of the body element.

Said base surface may be a base surface of a moveable element of the holding portion.

A shielding portion may be provided by one or more surface portions of one or both of the coupling portions of the first and second support bodies.

Preferably the first piercing member is made substantially from metal.

Preferably the first piercing member comprises a first insertion portion, adjacent the pointed end, for insertion into the tissue.

Preferably the first insertion portion is substantially arcuate.

Preferably the first piercing member comprises a first mounting portion for mounting in the first support body.

Preferably the first piercing member comprises a first intermediate portion, between the first mounting portion and the first insertion portion.

Preferably the first support body is made of a plastic.

Preferably the first support body is moulded around at least the first mounting portion of the first piercing member.

Preferably the first piercing member is made substantially from metal.

Preferably the second piercing member comprises a second insertion portion, adjacent the pointed end, for insertion into the tissue.

Preferably the second insertion portion is substantially arcuate.

Preferably the second piercing member comprises a mounting portion for mounting in the second support body.

Preferably the second piercing member comprises a second intermediate portion, between the second mounting portion and the second insertion portion.

Preferably the second support body is made of a plastic.

Preferably the second support body is moulded around at least the second mounting portion of the second piercing member.

Preferably the first and second insertion portions are substantially coplanar.

In one embodiment, the first and second insertion portions are not exactly coplanar but are aligned in substantially parallel closely spaced apart planes.

Preferably, the pointed end parts of the first and second piercing members are located in close proximity when the anchoring portion is in the closed position.

The pointed end parts may oppose each other when the anchoring portion is in the closed position.

Preferably the attachment device comprises holding means, coupled to the anchoring portion, for holding an elongate object. The holding means may be adapted for holding a catheter tube, drainage tube and/or other tube or elongate medical apparatus. The holding means may comprise first and second holding portions.

The attachment device in accordance with the first aspect of the invention may also be in accordance with the second aspect.

According to a second aspect of the present invention, there is provided an attachment device for attaching an elongate object to a patient, the attachment device comprising:
attachment means for attaching the device to a patient; and
holding means for holding an elongate object;
wherein the holding means comprises a first holding portion for engaging a first surface part of an elongate object and a second holding portion for engaging a second surface part of an elongate object, the first and second holding portions being mutually relatively movable, between an open position which allows removal of said elongate object and a closed position adapted to securely retain said elongate object.

Preferably, the first and second holding portions are moveable about a pivotal connection therebetween.

Preferably, the axis of the pivotal connection is not substantially parallel to the axis which said elongate object is aligned when held securely by the attachment device.

It will be appreciated that in some embodiments the elongate object is not to be held oriented in a single axis, and it should therefore be appreciated that reference to the axis in which the elongate object is aligned should be considered an approximation under some circumstances.

Preferably the axis of the pivotal connection is substantially perpendicular to the axis along which the elongate object is aligned when held securely by the attachment device.

The attachment means may be an anchoring portion of the attachment device which uses one or more piercing members to secure the device to the tissue of a patient. The attachment device in accordance with the second aspect of the invention may also be in accordance with the first aspect.

Alternatively, other suitable attachment means may be used.

Preferably the first holding portion defines a first cross sectional part of a passageway for accommodating the elongate object.

Preferably the second holding portion defines a second cross sectional part of a passageway for accommodating the elongate object.

Preferably the first cross sectional part of the passageway for accommodating the elongate object comprises a first channel portion.

Preferably the first channel portion has a wall portion with a surface which is substantially arcuate in radial cross section.

Preferably the second cross sectional part of the passageway for accommodating the elongate object comprises a second channel portion.

Preferably the second channel portion has a wall portion with a surface which is substantially arcuate in radial cross section.

There may be provided one or more subsequent holding portions with respective subsequent channel portions.

Preferably, when the holding portion is in its closed configuration the channel portions form a passageway which is adapted to securely hold the elongate object.

Preferably the passageway is provided with one or more grip elements therein.

Preferably the grip elements are projections which extend inwardly from one or more wall portions of the passageway.

Preferably, at least one grip element is made from a material which is more easily deformable than the material from which at least one holding portion is made.

Preferably, at least one grip element is made from a material with a higher coefficient of friction than the material from which at least one holding portion is made.

At least part of the passageway may be provided with a tacky material thereon.

Use of a tacky material and/or soft and/or high friction grip elements can enhance the security with which an elongate object is held.

Preferably the passageway is somewhat curvilinear in form.

Preferably the passageway is somewhat serpentine in form.

In some embodiments the passage is substantially in a single plane.

The axis of the pivotal connection may be substantially perpendicular to the said plane of the passage.

Preferably, the attachment device has a substantially planar base surface.

Preferably the substantially planar base surface is for contact with the skin of a patient.

In some embodiments, the passage is in substantially a single plane. In this case, the plane of the passage may be substantially parallel to the plane of the planar base surface.

In some embodiments the attachment device may be adapted to direct the elongate object towards the patient. This may assist in keeping a catheter tube or drain tube close to the patient in the region adjacent the attachment device and thereby reducing the likelihood of inadvertent snagging or other deleterious accidental contact with the tube.

The passage may be inclined towards the base surface at or adjacent one or more of the ends of the passage.

Preferably the axis of the pivotal connection is substantially perpendicular to the plane of the planar base surface.

Preferably, the relative movement of the first and second holding portions is generally in a plane substantially parallel to the plane of the base surface.

Preferably there is provided a locking means for locking the holding portion in its closed position.

Preferably the locking means comprises a first locking element provided on the first holding portion and a second complementary locking element provided on the second holding portion.

Preferably the pivotal connection comprises a hinge.

Preferably the hinge comprises an outer hinge element and an inner hinge element located within, and pivotally moveable with respect to, the outer hinge element.

Preferably, the outer hinge element is provided on one of the holding portions.

Preferably, the inner hinge element is provided on another of the holding portions.

Preferably the holding means is provided with object retaining means for removably retaining an object when the holding means is in its open position.

Preferably the object retaining means comprises at least two contact portions, spaced apart so as to gently hold an elongate object of given cross sectional dimensions therebetween.

Preferably a first contact portion is provided on one holding portion, and a second contact portion is provided on a different holding portion.

Alternatively, both or all the contact portions may be provided on a single element of the holding means.

Preferably, the attachment device is provided with a holding portion position retaining means to prevent inadvertent closure of the holding means.

Preferably the holding portion position retaining means is adapted to prevent closure of the holding means when a force less than a predetermined force is applied to close the holding means, but to allow closure of the holding means when a force greater than a predetermined force is applied to close the holding means.

Preferably the predetermined force is of a magnitude that can be applied to the device by the grip of a finger and thumb by a single hand of a user.

Preferably the predetermined force is less than 30 Newtons.

Preferably the position retaining means comprises a bearing portion provided on one part of the attachment device and a complementary bearing portion provided on another part of the attachment device, said bearing portions being arranged so that they may slide past each other upon application of a predetermined force.

Preferably, the bearing portion is provided on one holding portion.

Preferably, the complementary bearing portion is provided on another holding portion. The bearing portion on one holding portion may comprise a shaped surface part which projects further from the axis of the rotation about which the said holding portion can move, than adjacent surface parts. The bearing portion may therefore offer resistance, by bearing against the complimentary bearing portion.

Alternatively, the bearing portion may comprise a projection on a generally planar surface of the holding means which offers resistance against sliding past of the complimentary bearing portion. The complimentary bearing portion may comprise an edge of a holding portion.

Preferably the outer hinge element has a partially cylindrical inner surface, and is provided with an axially extending opening.

Preferably the inner hinge element has at least one partially cylindrical surface portion for contact with the partially cylindrical inner surface of the outer hinge element.

Preferably the inner hinge element has cross sectional shape with a lesser width in a first radial direction than in a second radial direction, so that it can be inserted into the outer hinge element through the axially extending opening when orientated with the first radial direction aligned with the width of the axially extending opening, and can be retained in the outer hinge element when not so oriented.

According to a third aspect of the present invention there is provided an attachment device for attaching an elongate object to a patient comprising:

an anchoring portion, operable between an open position in which the anchoring portion is inoperative and a closed position in which at least one piercing member is deployed for anchoring the device to the tissue of a patient; and holding means for holding said elongate object wherein the holding means is operable between an open position which allows removal of said elongate object and a closed position adapted to securely retain said elongate object.

Preferably the anchoring portion is operable from the open position to the closed position by manually forcing two relatively moveable parts of the anchoring portion.

Preferably the anchoring portion is provided with anchoring portion locking means for locking the anchoring portion in the closed position.

Preferably the holding means is operable from the open position to the closed position by manually forcing two relatively moveable parts of the holding means.

Preferably the holding means is provided with holding means locking means for locking the holding means in the closed position.

Preferably the anchoring portion and the holding means comprise complementary restraining portions for preventing operation of the anchoring portion from the open position to the closed position when the holding means is in its open position.

According to a fourth aspect of the present invention there is provided a method of attaching an elongate object to a person or animal, the method comprising:

securely attaching an attachment device to the elongate object;

securely attaching the attachment device to the person or animal.

Preferably, the elongate object is a tube.

Preferably, the tube is a catheter tube or drain tube.

Preferably, the step of attaching the attachment device comprises inserting at least one piercing member into tissue of the person or animal.

Preferably, the method comprises use of an attachment device in accordance with the first aspect of the present invention.

Preferably, the method comprises use of an attachment device in accordance with the second aspect of the present invention.

Preferably, the step of attaching the elongate object to the attachment device comprises placing the attachment device at or close to the position where the attachment device is to be attached to the person or animal.

Preferably, the step of attaching the elongate object to the attachment device comprises moving a first holding portion of the attachment device relative to a second holding portion of the attachment device to secure the elongate object between parts of the first and second holding portions.

Preferably, the step of attaching the elongate object to the attachment device comprises moving the first holding portion in a plane generally parallel to the plane of the skin adjacent the attachment device.

It will be appreciated that features set out in relation to an aspect of the invention may be of relevance to other aspects.

BRIEF DESCRIPTION OF THE DRAWINGS

Embodiments of the invention will now be described, by way of example only, with reference to the accompanying drawings in which:

FIG. 1 is a perspective view of an attachment device in which a clip portion for attachment to the skin of a patient and a gripping portion for gripping a catheter tube are both shown in their open positions;

FIG. 2 is a plan view from above corresponding to FIG. 1;

FIG. 3 is a first end view corresponding to FIG. 1;

FIG. 4 is a first side view corresponding to FIG. 1;

FIG. 5 is a bottom plan view corresponding to FIG. 1;

FIG. 7 is a perspective view of the attachment device of FIG. 1 but showing the gripping portion of the device in its closed position;

FIG. 8 is a plan view corresponding to FIG. 7;

FIG. 9 is a first end view corresponding to FIG. 7;

FIG. 10 is a first side view corresponding to FIG. 7;

FIG. 17 is a perspective view of a clip body which forms part of the clip portion of the attachment device of FIG. 1;

FIGS. 18, 19 and 20 show the clip body of FIG. 17 in positions corresponding to the positions of FIGS. 2, 3 and 4 with all other features of the attachment device of FIG. 1 omitted;

FIGS. 21 and 22 are further views of the clip body of FIG. 17;

FIG. 35 is a perspective view from above of a moveable element of the gripping portion;

FIG. 36 is a plan view from above of the moveable element of FIG. 35;

FIG. 37 is a first end view of the moveable element of FIG. 35;

FIG. 38 is a first side view of the moveable element of FIG. 35;

FIGS. 39 and 40 are perspective views from below of the moveable element of FIG. 35;

FIG. 89 is a cross sectional perspective view corresponding to FIG. 88;

FIG. 90 is a perspective view of a further alternative embodiment of an attachment device (which has many similarities to the embodiment of FIGS. 47 to 85) in which a clip portion is shown in its closed position and a gripping portion is shown in its open position;

FIG. 91 is a further perspective view corresponding to FIG. 90;

FIG. 92 is a plan view from above corresponding to FIG. 90;

FIG. 93 is a first end view corresponding to FIG. 90;

FIG. 94 is a first side view corresponding to FIG. 90;

FIG. 107 to 111 are perspective views of a main body of the gripping portion of the embodiment of FIGS. 90 to 103 from, respectively, above front, below front, above rear, below rear, and substantially front;

DETAILED DESCRIPTION OF PREFERRED EMBODIMENTS

Figure 6:
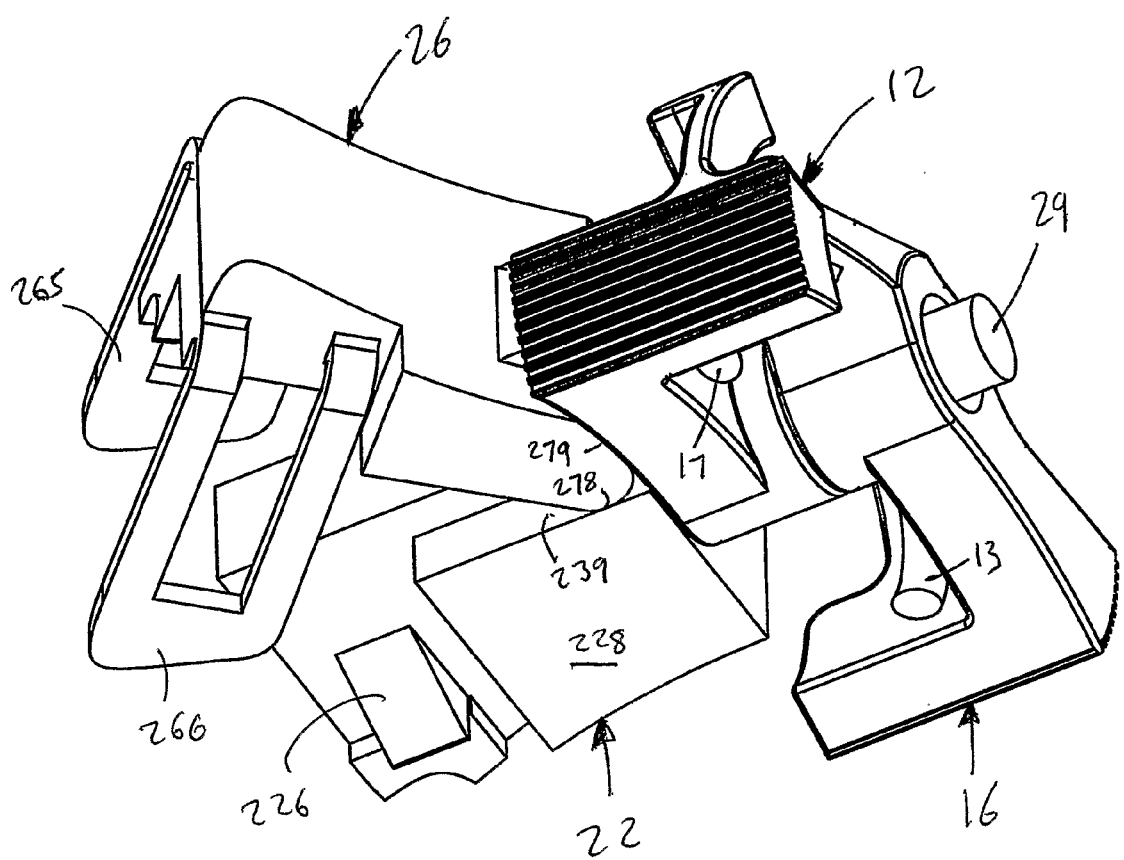
FIG. 6 is a perspective view from beneath corresponding to FIG. 1.
Figure 11:
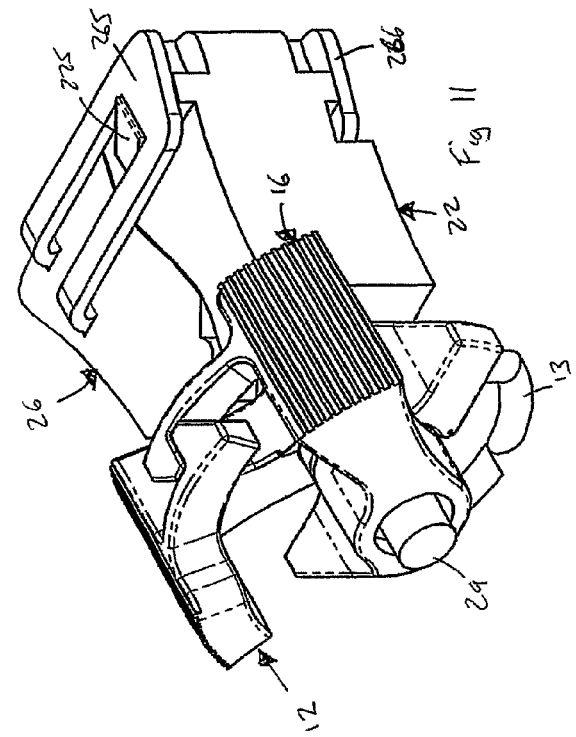
FIG. 11 is a perspective view generally corresponding to the views of FIGS. 1 and 7 but showing both the gripping portion and the clip portion in their closed positions.
Figure 14:
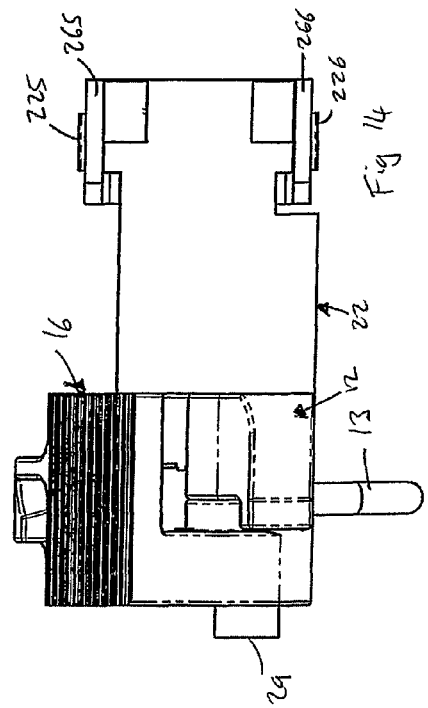
FIG. 14 is a first side view corresponding to FIG. 11.
Figure 12:
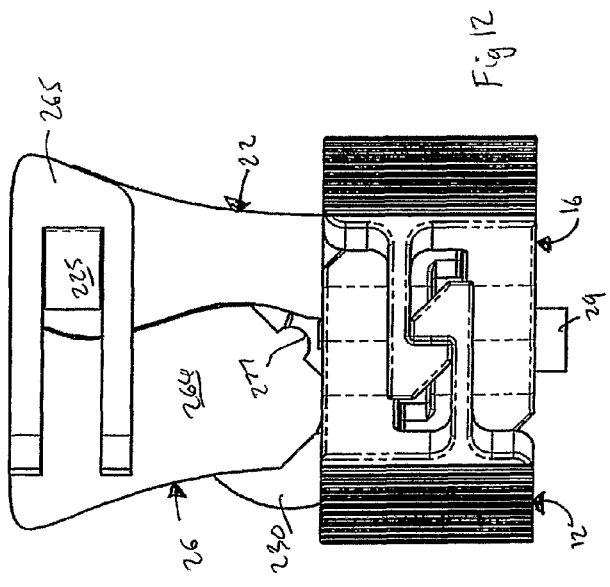
FIG. 12 is a plan view corresponding to FIG. 11.
Figure 13:
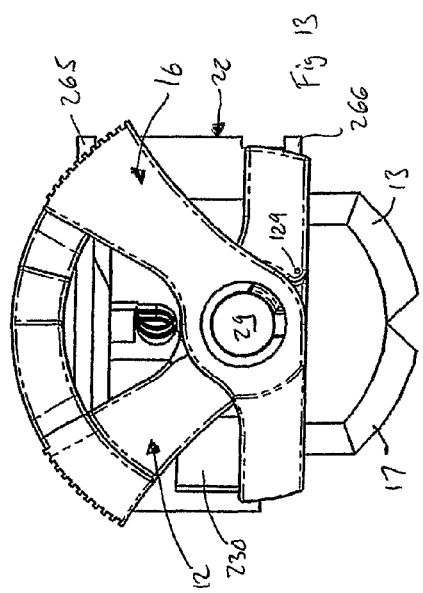
FIG. 13 is a first end view corresponding to FIG. 11.

With reference to FIGS. 1 to 46, and in particular FIGS. 1 to 16, an embodiment of an attachment device generally designated 1 comprises a clip portion 10, for attachment to the skin of the patient, at one end thereof and a gripping portion 20 for gripping a tube such as a catheter or surgical drain tube at the second end thereof. The clip portion 10 comprises a first clip body 12 to which is mounted a first piercing member in the form of a first prong 13. The clip portion 10 further comprises a second clip body 16 upon which is mounted a second piercing member in the form of a second prong 17.

The gripping portion 20 comprises a main body 22 and a movable element 26 which can be moved relative to the main body 22 and secured in order to grip a tube such as a catheter tube between a part of the movable element 26 and a part of the main body 22 (as illustrated by the configuration of the device shown in FIGS. 7 to 16). The main body 22 is provided with an attachment element 29 which projects therefrom towards the first end of the attachment device and upon which are mounted the first and second clip bodies 12,16. The first and second clip bodies 12,16 can pivot about the attachment element and can be secured so that the first and second prongs 13,17 penetrate into the tissue of a patient and secure the attachment device to the patient, (when the device is in the configuration shown in FIGS. 11 to 16).

In the illustrated embodiment each of the first and second clip bodies is substantially identical and such a clip body is illustrated in isolation in FIGS. 17 to 22. It will be appreciated that the clip body shown in FIGS. 17 to 20 is shown in positions corresponding to the position of the first clip body as shown in FIGS. 1 to 4, respectively but with the first piercing member omitted. Since in the preferred embodiment the first clip body 12 and second clip body 16 are substantially identical in form, the clip body illustrated in FIGS. 17 to 22 will be described hereafter as the first clip body 12 although it will be appreciated that the second clip body (at least in this embodiment) comprises corresponding features.

As illustrated by FIGS. 17 to 22 the first clip body 12 comprises an operating portion 122 via which a user may operate the clip portion 10. The operating portion is provided with a grip surface 123 enhancing secure contact with the fingertip or thumb tip of a user. A shank portion 124 connects the operating portion to a connection portion in the form of a boss 126 provided with a through aperture 127. The shank portion 124 extends away from the boss 126 in a direction generally perpendicular to the axis of the through aperture 127. The shank portion 124 is provided with an inner side surface 125 generally perpendicular to the axial direction of the through aperture 127 and an outer side surface 137 on the opposite side of the shank portion, and generally parallel to the inner side surface.

Projecting away from the boss 126 on a side of the boss generally opposed to the side at which the shank portion 124 is connected to the boss, there is provided a prong support portion 128. The prong support portion 128 projects away from the boss in a direction generally perpendicular to the axis of the through aperture 127 and may be regarded as projecting in a direction approximately 135° from the direction at which the shank portion 124 projects away from the boss 126.

The prong support portion 128 is provided with an inner side surface 132 generally parallel to the inner side surface 125 of the shank portion. The inner side surface 132 is generally planar, but is provided with a small restraining projection 129 which projects away from the planar surface of the inner side surface 132. The prong support portion 128 is provided with a prong fitting cavity 130 for fitting the first prong 13 (not shown in FIGS. 17 to 22) thereto. The prong fitting cavity extends close to the inner side surface 132 so that the first prong 13 can project from the prong support portion 128 from a position close to the inner side surface 132. At least part of the prong support portion 128 may be regarded as offset from the shank portion 124.

More particularly, in this embodiment, the inner side surface 132 of the prong support portion 128 is offset from the inner side surface 125 of the shank portion 124 in the axial direction of the through aperture 127 which is also, in this embodiment, the axial direction of the device as a whole. Projecting from the operating portion 122 there is provided a clasp portion 133 comprising an arcuate arm 134 and a clasping element 135 at the distal end of the arcuate arm.

In this embodiment the through aperture 127 is not merely cylindrical but comprises a generally cylindrical bore provided with a groove 147 which provides a region of increased radius over an angular extent of approximately ninety degrees. The groove 147 is bounded by first and second step portions 148, 149 angularly spaced apart, which connect a part-cylindrical inner surface of the groove 147 with the part-cylindrical inner surface of the rest of the through aperture 127. In this embodiment the step portions 148, 149 are not aligned in radial planes of the through aperture 127. The through aperture 127 is provided with an interior circumferential step which provides a part annular shoulder 150 in a radial plane of the through aperture 127, adjacent the end of the through aperture 127 that connects to the outer side surface 137 of the shank portion of the clip body. This effectively provides a slight widening of the through aperture at the end which is at the outer side of the clip.

In use, first and second substantially identical clip bodies 12, 16 are mounted on the attachment element 29 so that they may pivot about a common axis, defined by the central axis of the through apertures 127 of each body, and by the attachment element 29. The clip bodies 12, 16 are retained on the attachment element so that the inner side surface 125 of the shank element 124 of each clip body 12, 16 engages and can bear against the inner side surface 132 of the prong support portion 128 of the other clip body.

Figure 23:
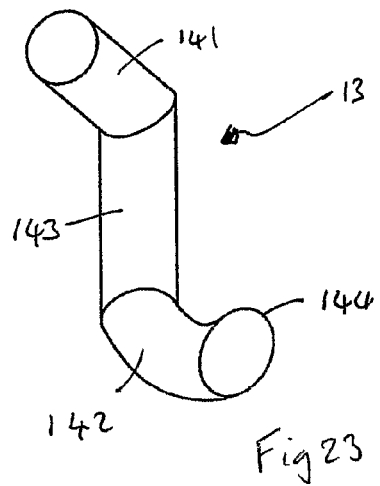
FIGS. 23 to 26 are views of a prong for use in the clip portion.
Figure 24:
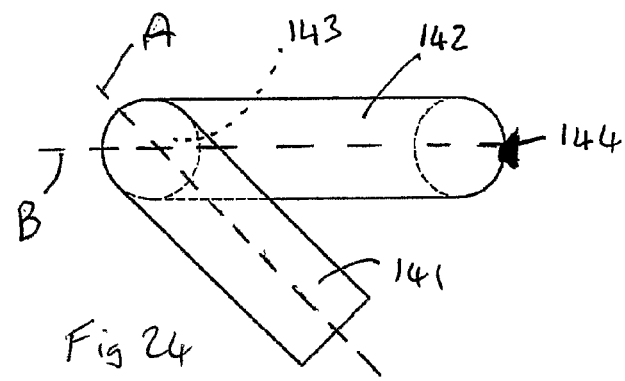
Figure 25:
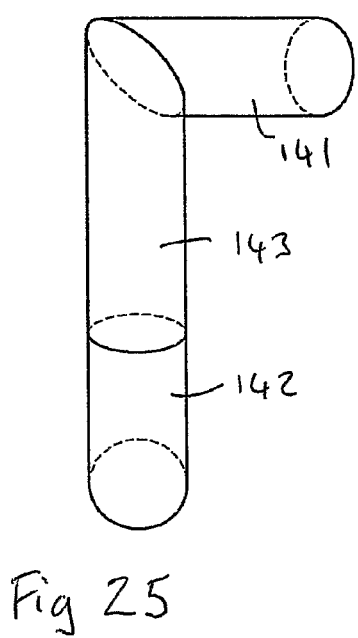

With reference to FIGS. 23 to 25, a first prong 13, for mounting upon a first clip body 12 is illustrated. It will be appreciated that the second prong 17 for mounting on the second clip body 16 will be substantially identical, in a preferred embodiment.

The first prong 13 comprises a mounting portion 141 for mounting in the prong fitting cavity 130 of the first clip body. The first prong 13 further comprises an insertion portion 142 for insertion into the tissue of a patient in order to anchor the attachment device. The mounting portion 141 and insertion portion 142 are connected by an intermediate portion 143. The insertion portion 142 is slightly longer than the mounting portion 141 and is somewhat arcuate in form and is provided with a point 144 at the end which is further from the intermediate portion 143. The mounting portion 141 and intermediate portion 143 are generally straight and are generally circular in cross-section. The mounting portion 141 is generally perpendicular to the intermediate portion 143. The insertion portion 142 depends at an angle of approximately 135° from the intermediate portion. As illustrated in FIGS. 23 to 26, the first prong as a whole is not planar in form. Rather, the mounting portion 141 and intermediate portion 143 may be considered to define a first plane (designated A in FIG. 24) and the insertion portion 142 and intermediate portion 143 may be considered to define a second plane (designated B in FIG. 24) which forms an angle of about 45° with the first plane. That is, the mounting portion and insertion portion are angularly displaced (about the axis of the intermediate portion) by approximately 45°.

Figure 26:
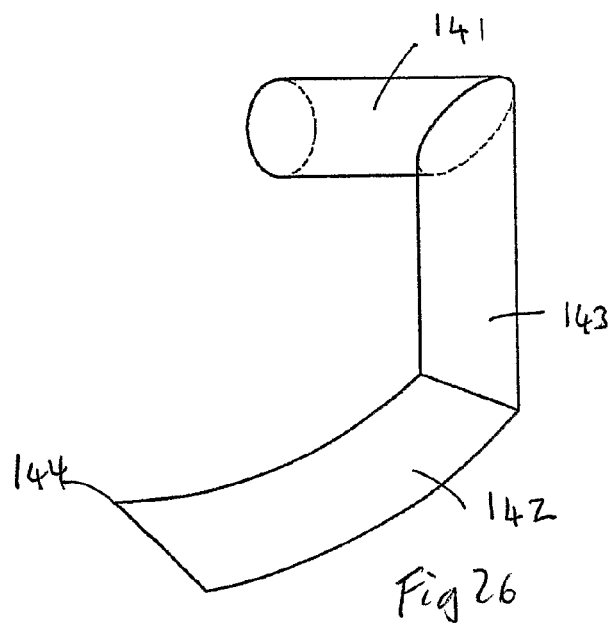
Figure 27:
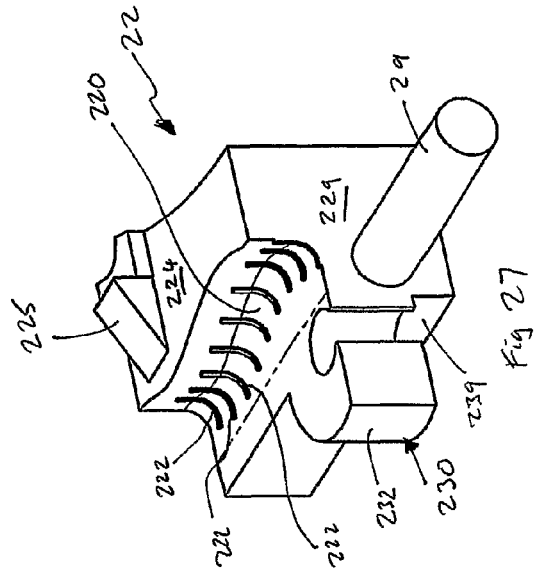
FIG. 27 is a perspective view of a main body of the gripping portion.
Figure 30:
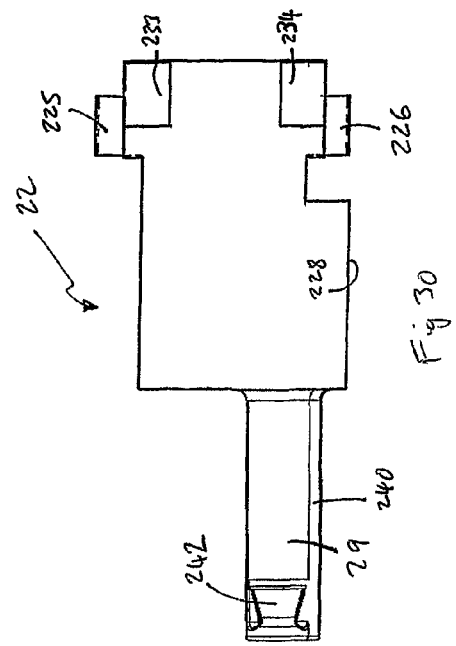
FIG. 30 is a first side view of the main body of FIG. 27.

As illustrated in FIG. 23, the intermediate portion is generally in the plane of the paper and the mounting portion 141 and insertion portion 142 extend outwardly from the plane of the paper somewhat to the left and right, respectively. As shown in FIG. 24, the axis of the mounting portion 141 is generally parallel to the plane of the paper, the axis of the intermediate portion 143 is generally perpendicular to the plane of the paper and the insertion portion 142 extends at an angle generally of 45° into the paper. As illustrated in FIG. 25, the intermediate portion 143 is generally in the plane of the paper. The plane defined by the insertion portion 142 and the intermediate portion 143 is generally perpendicular to the plane of the paper and the plane formed by the mounting portion 141 and the intermediate portion 143 is at approximately 45° to the plane of the paper, with the axis of the mounting portion 141 extending somewhat into the paper, away from the viewer. As illustrated in FIG. 26, the plane defined by the insertion portion 142 and intermediate portion 143 is generally in the plane of paper and the mounting portion 141 extends into the paper at an angle of approximately 45°.

The connection between the first prong 13 and the first clip body 12 may be made in any suitable way, for example including use of an adhesive. However, it is preferred that the first clip body should be actually moulded around the mounting portion 141 of the first prong 13. It will therefore be appreciated that the view of the prong fitting cavity 130 provided in the drawings is somewhat schematic and in a preferred embodiment, with the first prong 13 mounted in the first clip body, the prong fitting cavity 130 would not be externally visible.

FIGS. 28 to 34 show schematically and in isolation the main body 22 of the gripping portion 20. In FIGS. 27, 31, 32 and 34 (as in FIGS. 1 to 16) the attachment element 29 is shown schematically as a simple cylindrical rod. In a preferred embodiment, however, the attachment element 29 is in the form illustrated in FIGS. 28, 29, 30 and 33. The preferred form of the attachment element will be described in detail in due course.

The main body 22 of the gripping portion 20 defines a first channel portion 220 which is a somewhat serpentine in form and which is provided with a number of grip projections 222 which are preferably formed from a high friction material. The first channel portion 220 has a form which is partially arcuate in radial cross-section for receiving a tube such as a catheter tube. The main body 22 is provided with an upper surface 224 on which is provided an upper clasp element 225 and a basal surface 228 (for contact, in use, with the skin of a patient). A lower clasp element 226 is provided on a recessed portion 227 adjacent the basal surface 228 so that it does not project downwardly further than the basal surface 228. Also adjacent the basal surface 222, and generally perpendicular thereto, there is provided generally planar lower side surface 239.

The main body 22 is provided with a front surface 229 from which the attachment element 29 projects. As illustrated in FIGS. 28, 29, 30 and 33 the attachment element 29 is generally cylindrical in form. However, the attachment element further comprises an axially extending projecting rib 240 which extends substantially the entire length of the attachment element 29 on the underside thereof.

Figure 28:
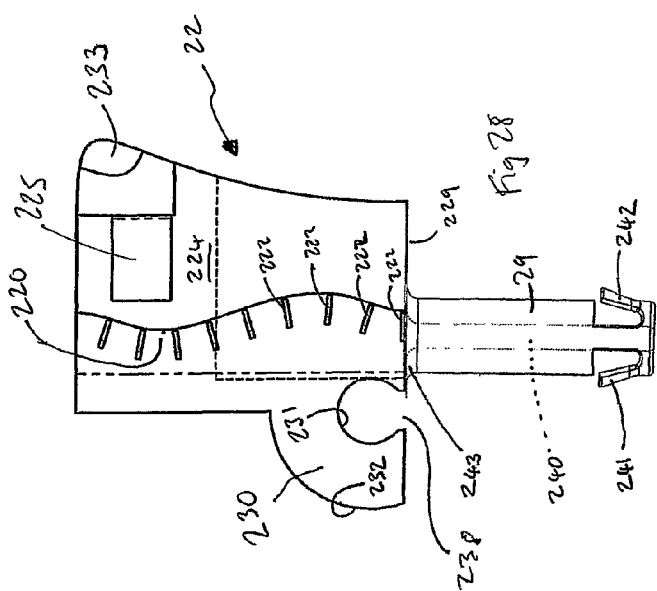
FIG. 28 is a plan view from above of the main body of FIG. 27.
Figure 29:
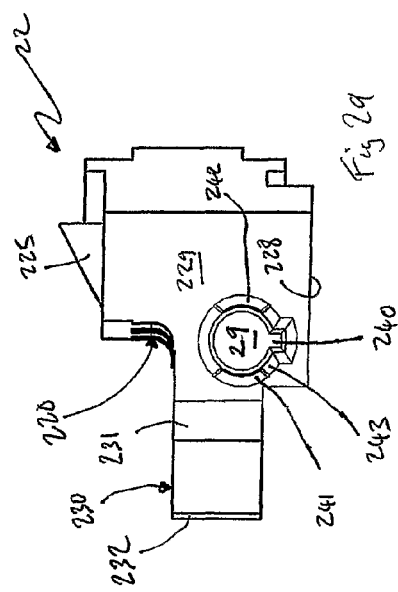
FIG. 29 is a first end view of the main body of FIG. 27.
Figure 31:
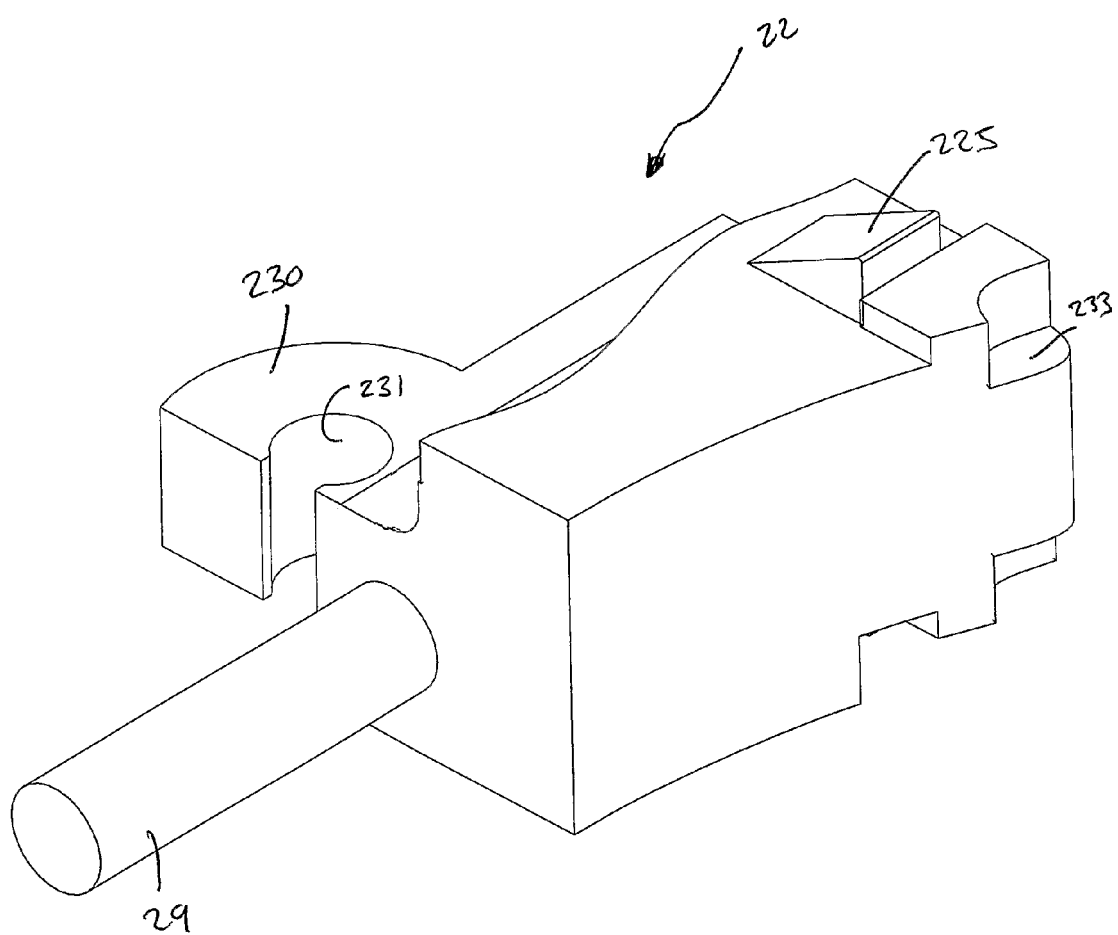
FIGS. 31 and 32 are additional perspective views, from above, of the main body of FIG. 27.
Figure 32:
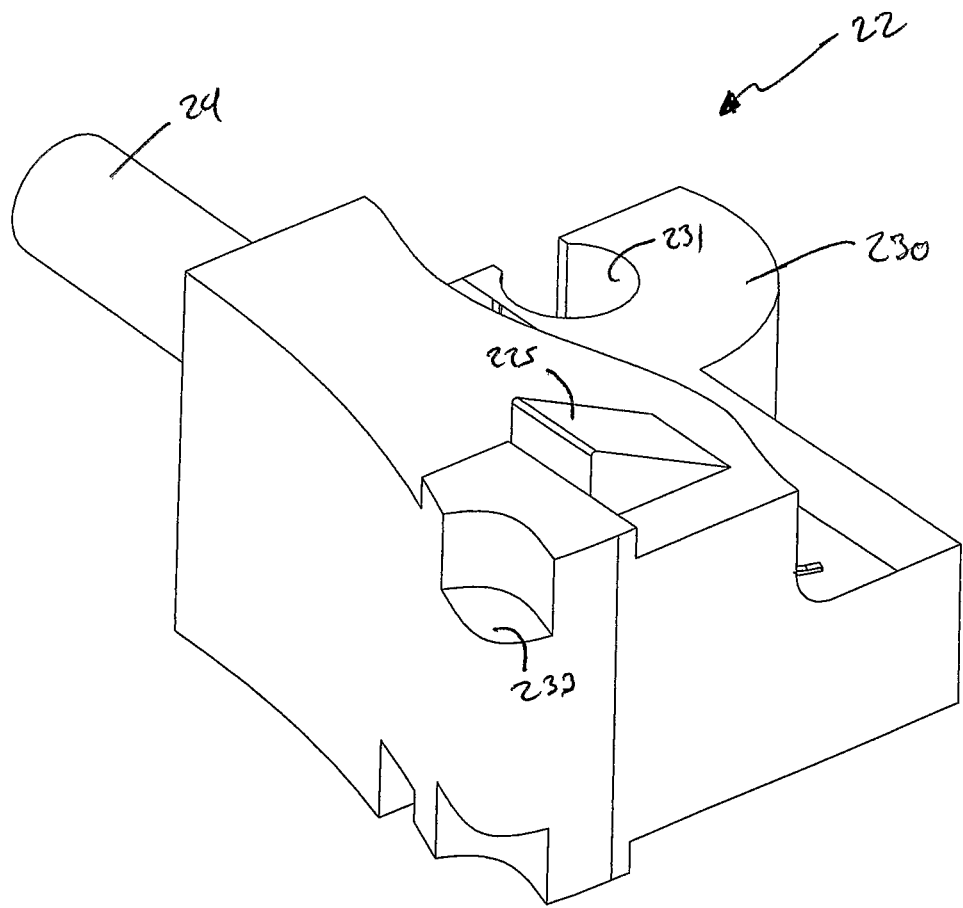
Figure 33:
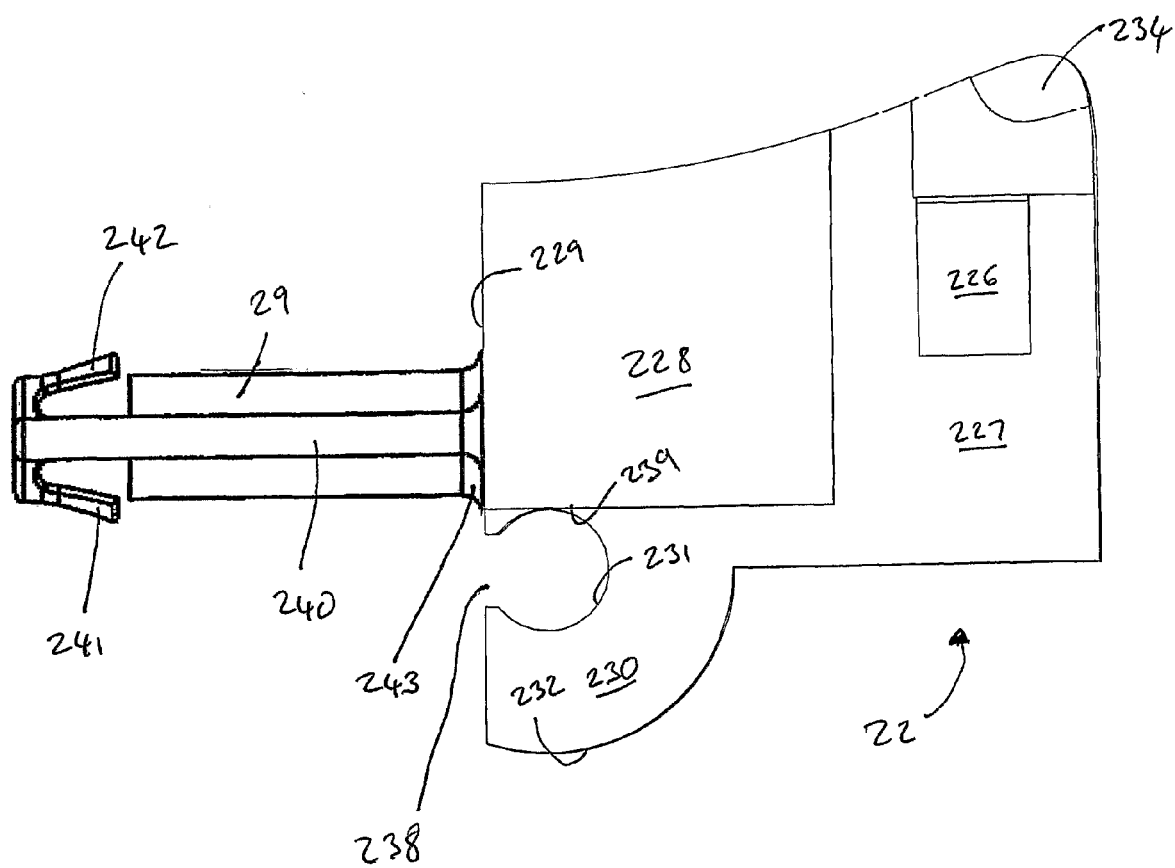
FIG. 33 is a bottom view of the main body of FIG. 27.
Figure 34:
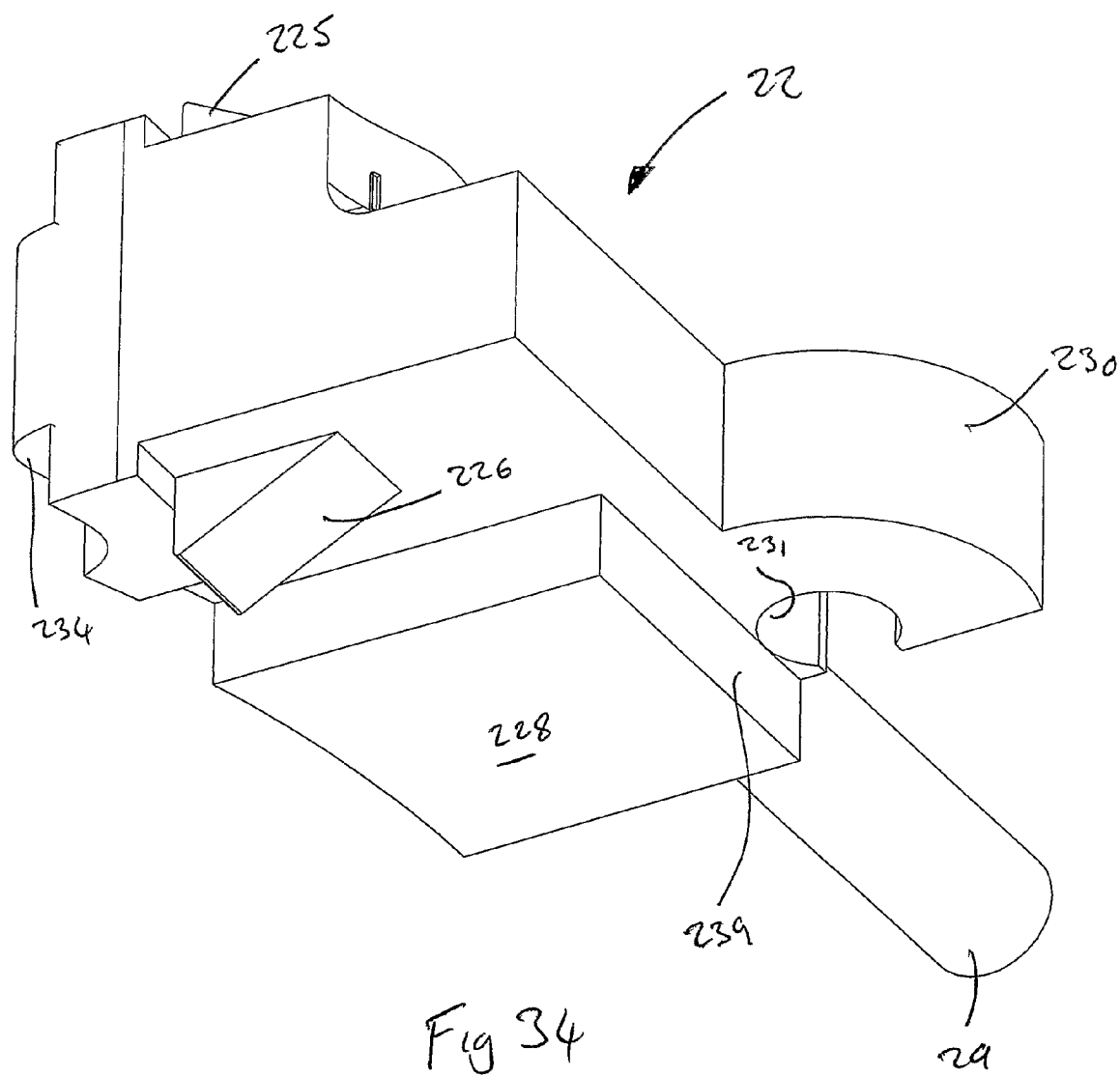
FIG. 34 is a perspective view from below of the main body of FIG. 27.
Figure 40:
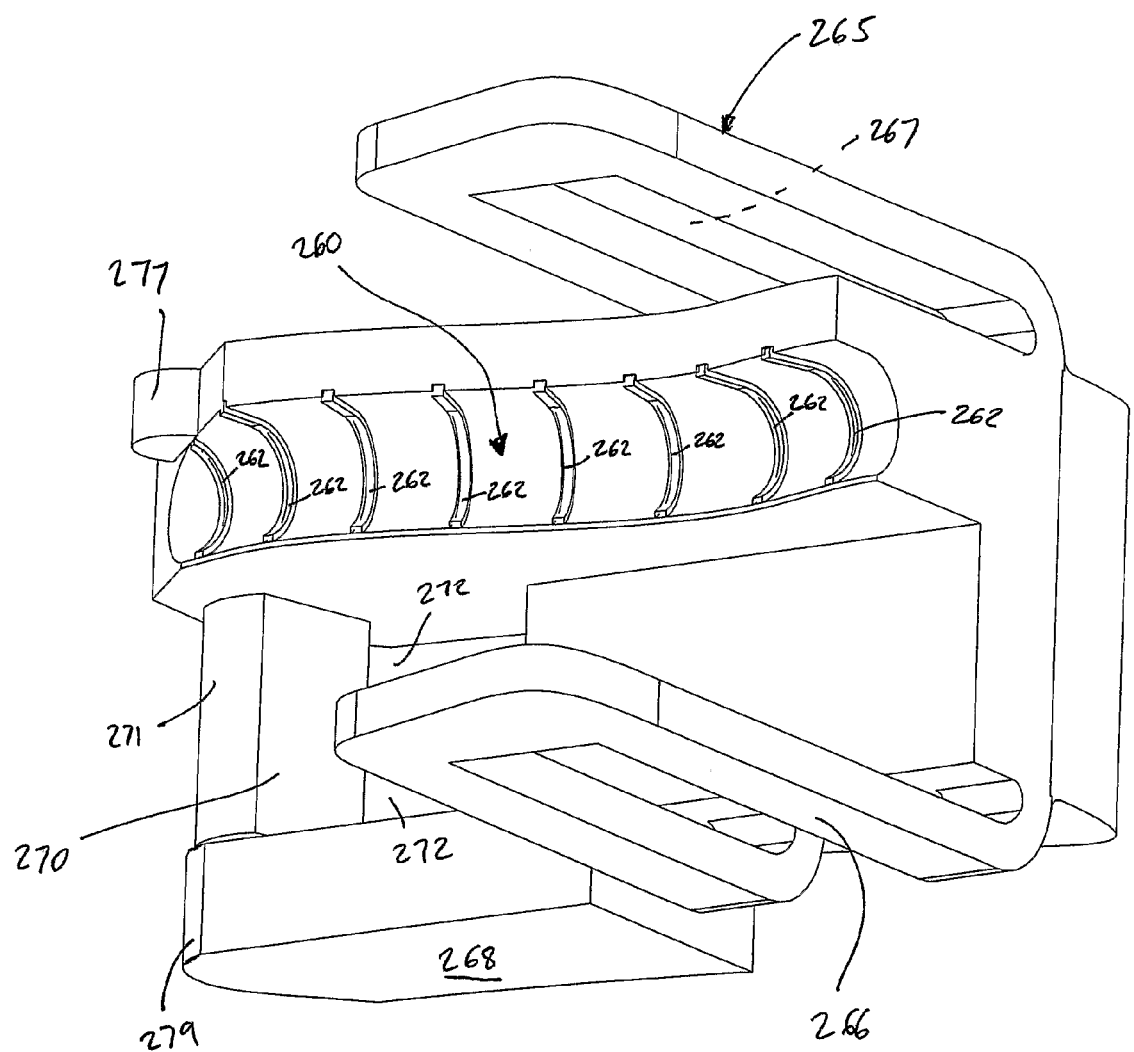
Figure 41:
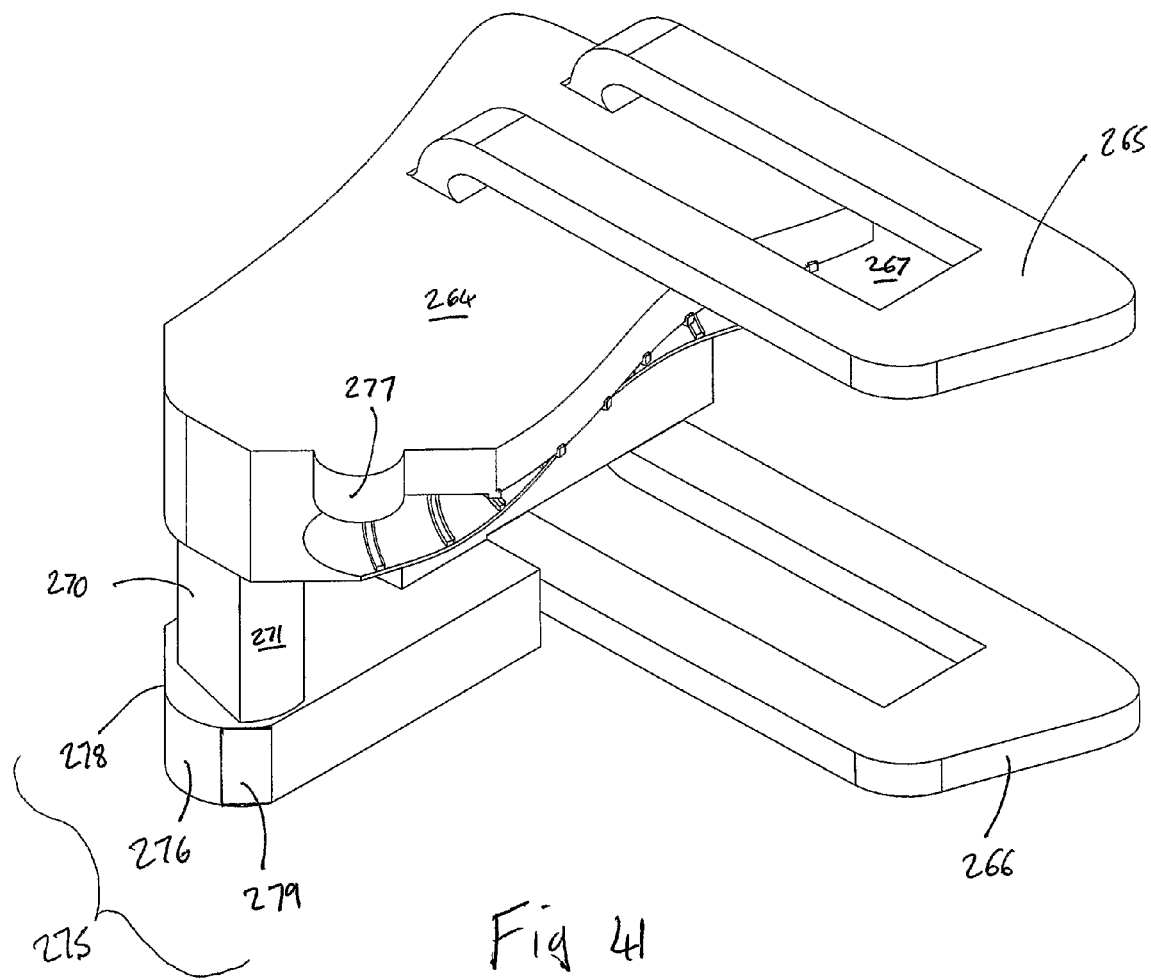
FIG. 41 is a further perspective view from above of the moveable element of FIG. 35.
Figure 42:
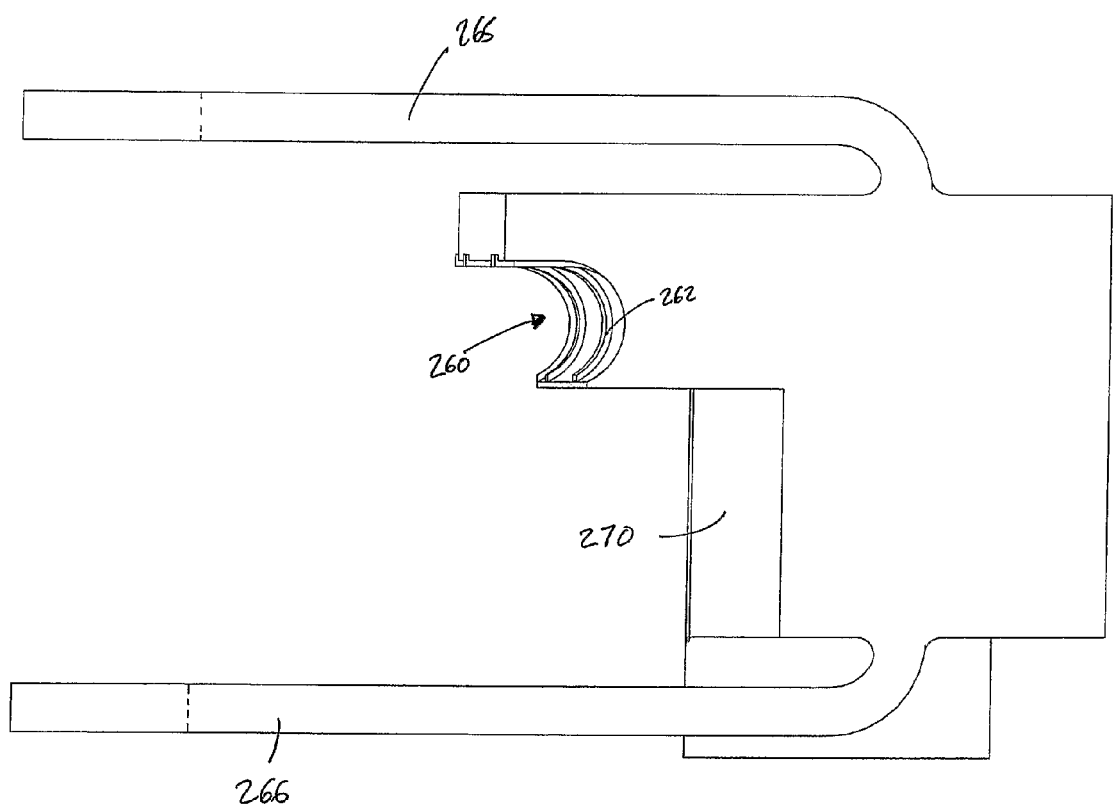
FIG. 42 is a second end view of the moveable element of FIG. 35.

At the end of the attachment element 29 which is distal from the rest of the main body 22 are provided first and second outwardly biased retaining elements 241, 242. As is best shown in FIGS. 28 and 29 the outwardly biased retaining elements 241, 242 are biased so that in their equilibrium positions they extend radially outward further than the generally cylindrical part of the attachment element 29. The outwardly biased retaining elements 241, 242, are therefore adapted to retain the first and second clip bodies 12, 16 on the connection element.

The main body 22 is further provided with a hinge portion 230 provided on one side thereof adjacent the generally planar lower side surface 239. The hinge portion 230 is for allowing pivotal connection of the main body 22 and the movable element 26 of the gripping portion 20. The hinge portion is part-circular in form having a part cylindrical inner surface 231 and a part cylindrical outer surface 232.

Adjacent the upper clasp element 225 there is provided an upper indentation 233 and adjacent the lower clasp element 226 there is provided a lower indentation 234. The indentations 233, 234 are provided in order to allow release of the clasping mechanism which will be described in due course.

With reference to FIGS. 35 to 42, the movable element 26 of the gripping portion 20 is provided with a second channel portion 260 which is complementary to the first channel portion 220 so that when the movable element 26 and the main body 22 are secured together, a tube such as a catheter tube can be securely gripped in a channel or passageway defined by the first and second channel portions 220, 260. The second channel portion 260 is provided with a number of grip projections 262, preferably made from a deformable and/or high friction material. Additionally, (or possibly as an alternative to providing grip projections) the interior surfaces of the channel portions may be provided with a tacky or gently adhesive material.

The movable element 26 of the gripping portion 20 further comprises an upper surface 264 from which projects an upper clasp element 265 adapted to securely attach to the upper clasp element 225 of the main body 22. The movable element further comprises a lower clasp element 266 projecting from a lower surface 268 of the movable element 26. The lower clasp element 266 is adapted to connect to the lower clasp element 226 of the main body 22. In a preferred embodiment each clasp element 265, 266 of the movable element 26 is provided with a slot 267 adapted to receive the respective ramp- or tooth-like clasp element (225, 226) on the main body 22. However, it will be appreciated that any suitable securing or clasp arrangement may be used (see, for example, the alternate embodiment of FIGS. 47 to 78).

The movable element 26 further comprises a hinge portion in the form of a hinge post 270 adapted to be received in the hinge portion 230 of the main body. The post 270 may be regarded as being in the form of a cylinder with two sides cut away so that the post 270 has two diametrically opposed convex part cylindrical surfaces 271 and two diametrically opposed planar surfaces 271a. Adjacent and partially defining the hinge portion of the moveable element 26, the movable element is provided with a void 272 for receiving at least part of the part cylindrical hinge portion 230 of the main body. The void 272 is defined at one side thereof by the hinge post 270 and at another side by a concave part-cylindrical surface 273 which is adapted to slidingly engage the part cylindrical outer surface 232 of the hinge portion 230 of the main body 22.

The movable element 26 further comprises a shaped lower front surface 275 which comprises first and second generally straight (or planar) abutment surfaces 278, 279 which are connected by a curved surface 276 and which are oriented generally at right angles relative to each other. Adjacent the hinge portion 270 and the shaped lower front surface 275 there is provided a tube-retaining projection 277 which projects markedly from an otherwise relatively smooth perimeter of the movable element.

Figure 15:
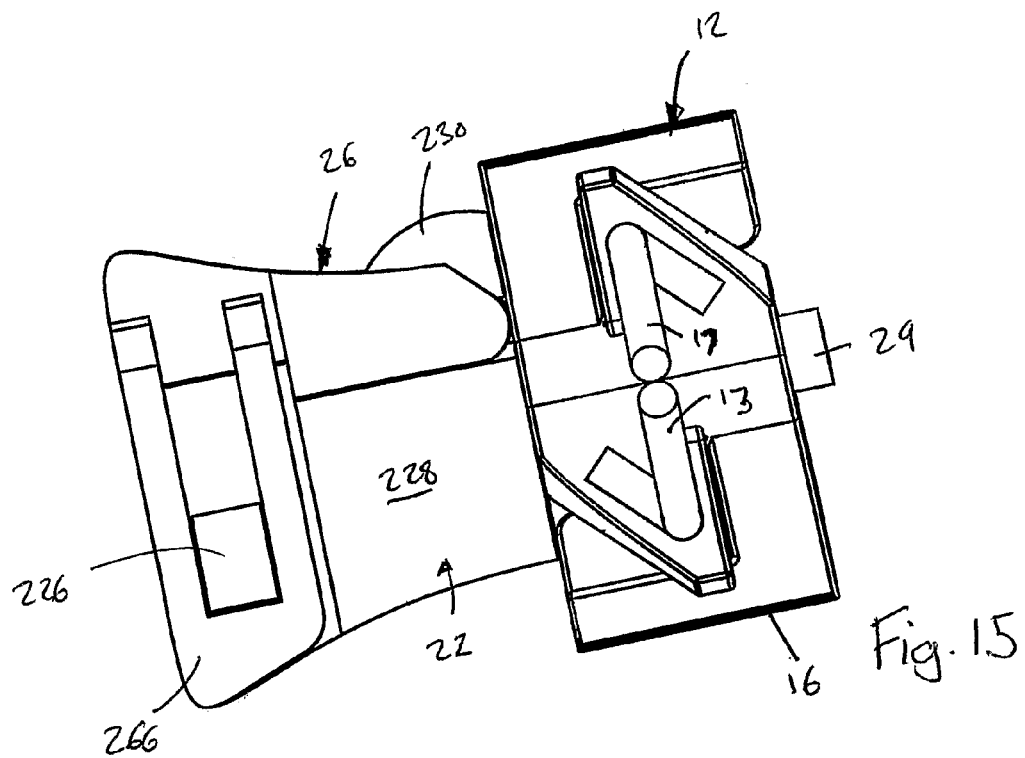
FIG. 15 is a bottom plan view corresponding to FIG. 11.
Figure 16:
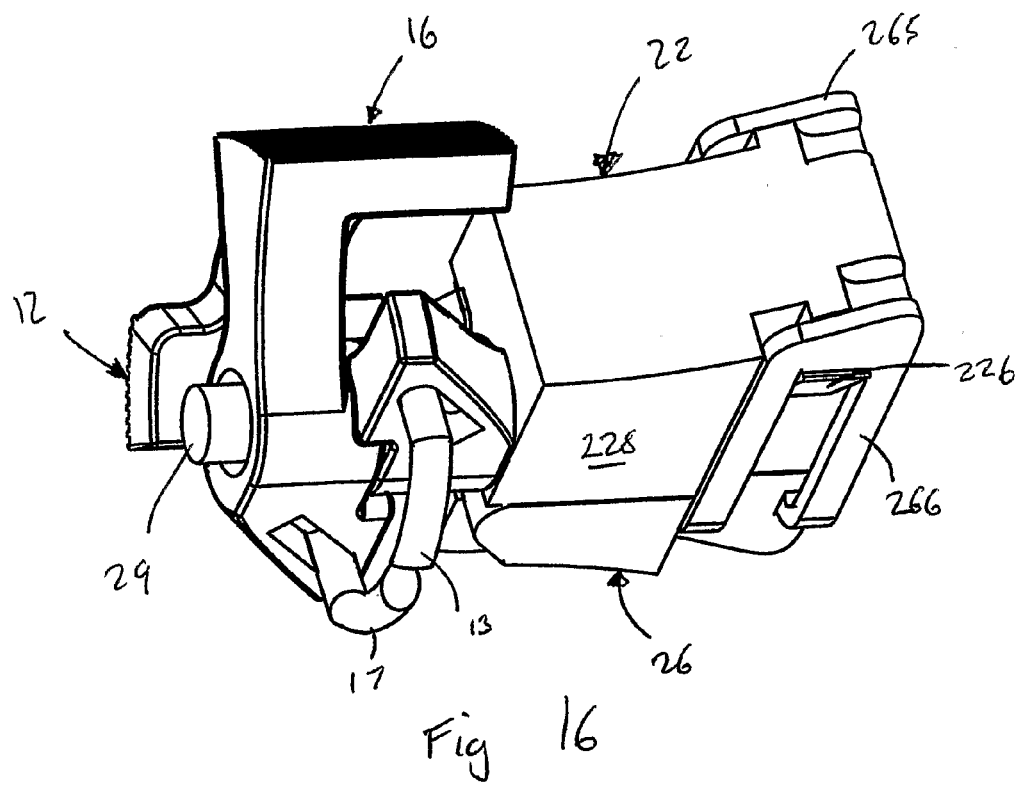
FIG. 16 is a perspective view from beneath and one side corresponding to FIG. 11.
Figure 22:
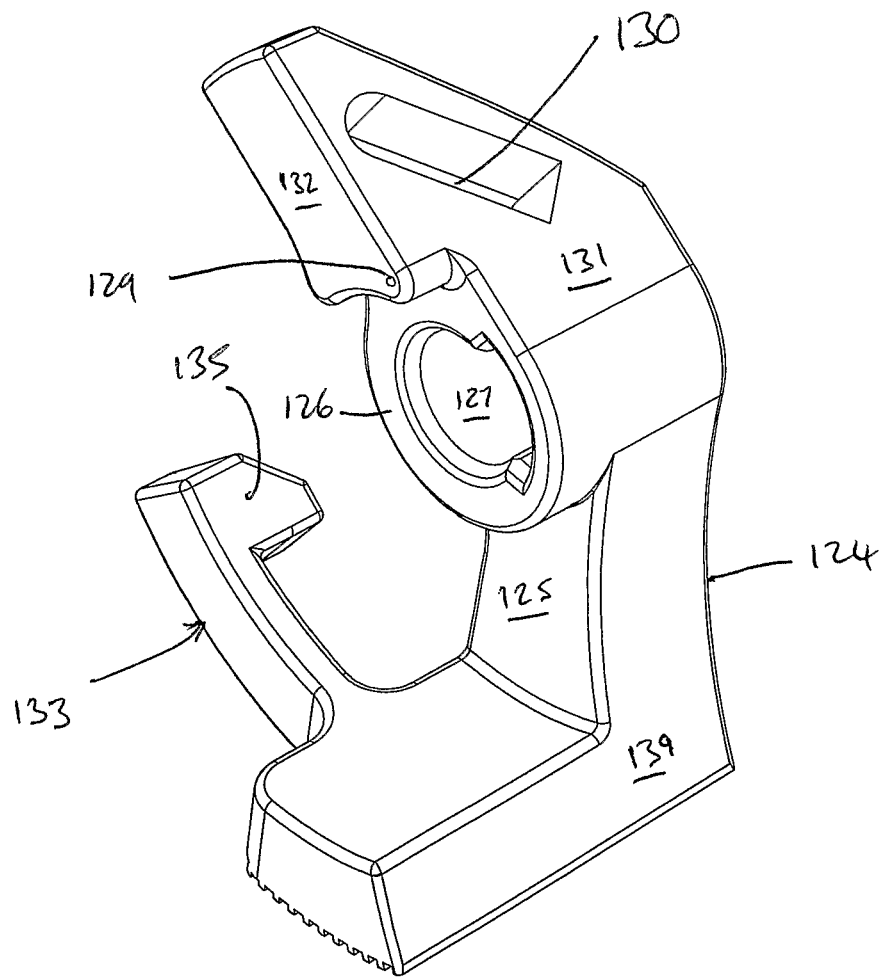
Figure 43:
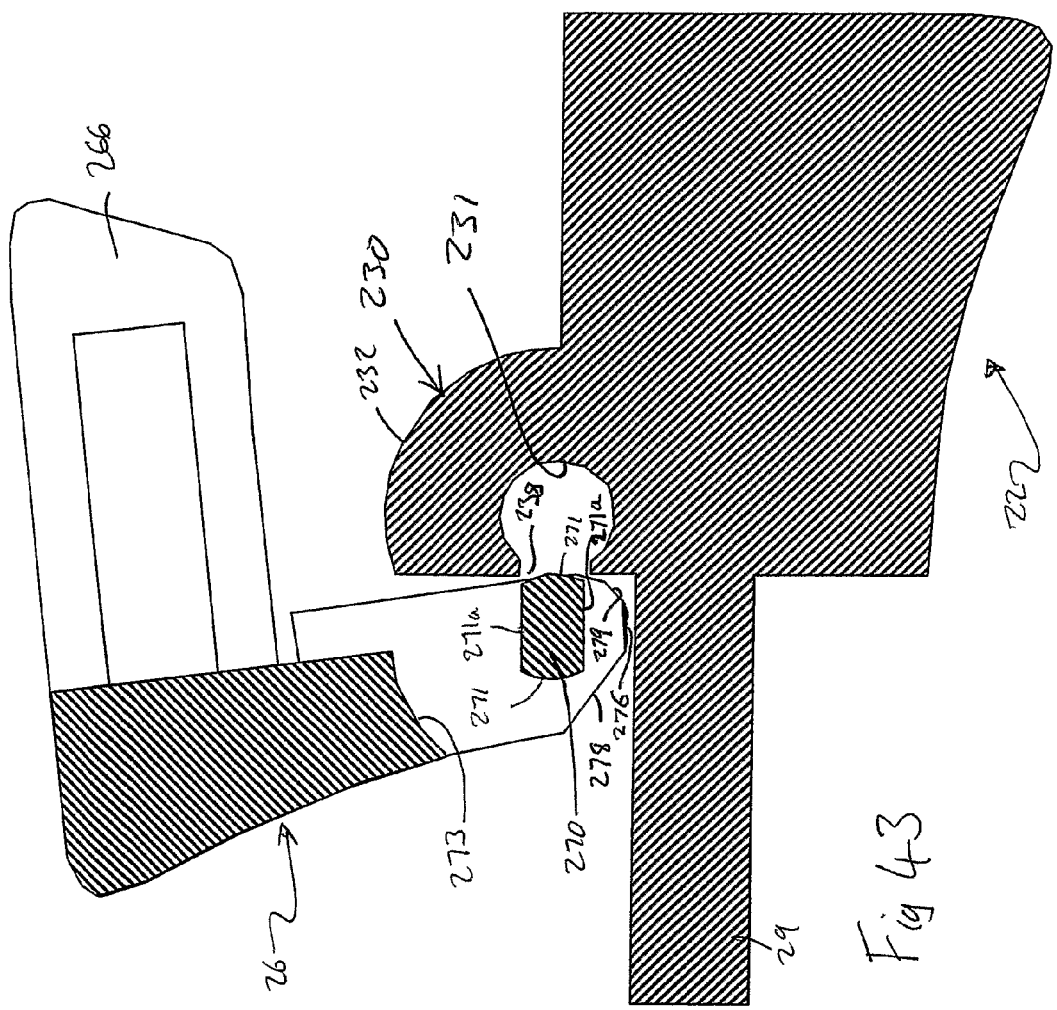
FIGS. 43 to 46 are schematic horizontal cross sectional views illustrating sequentially assembly and then closure of the gripping portion.
Figure 44:
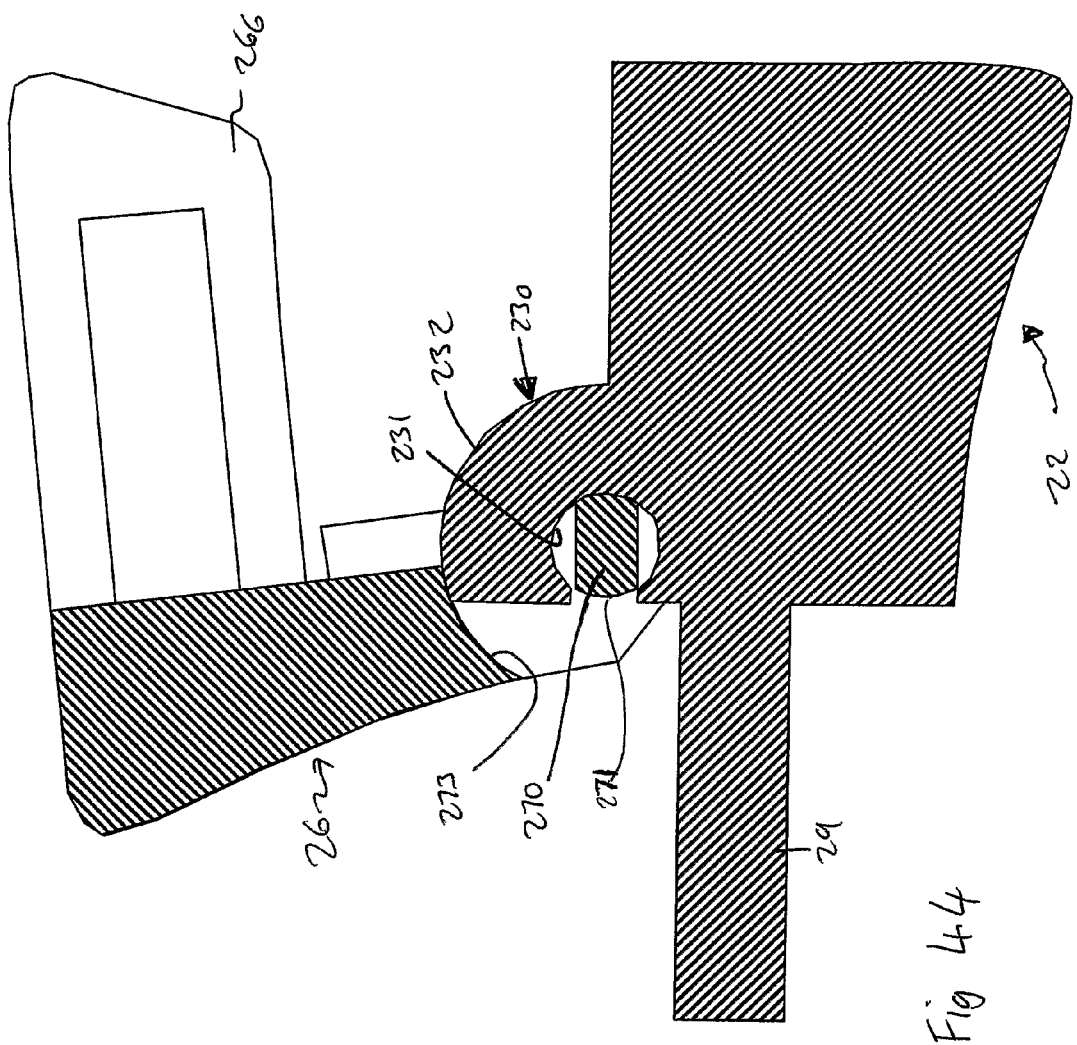
Figure 45:
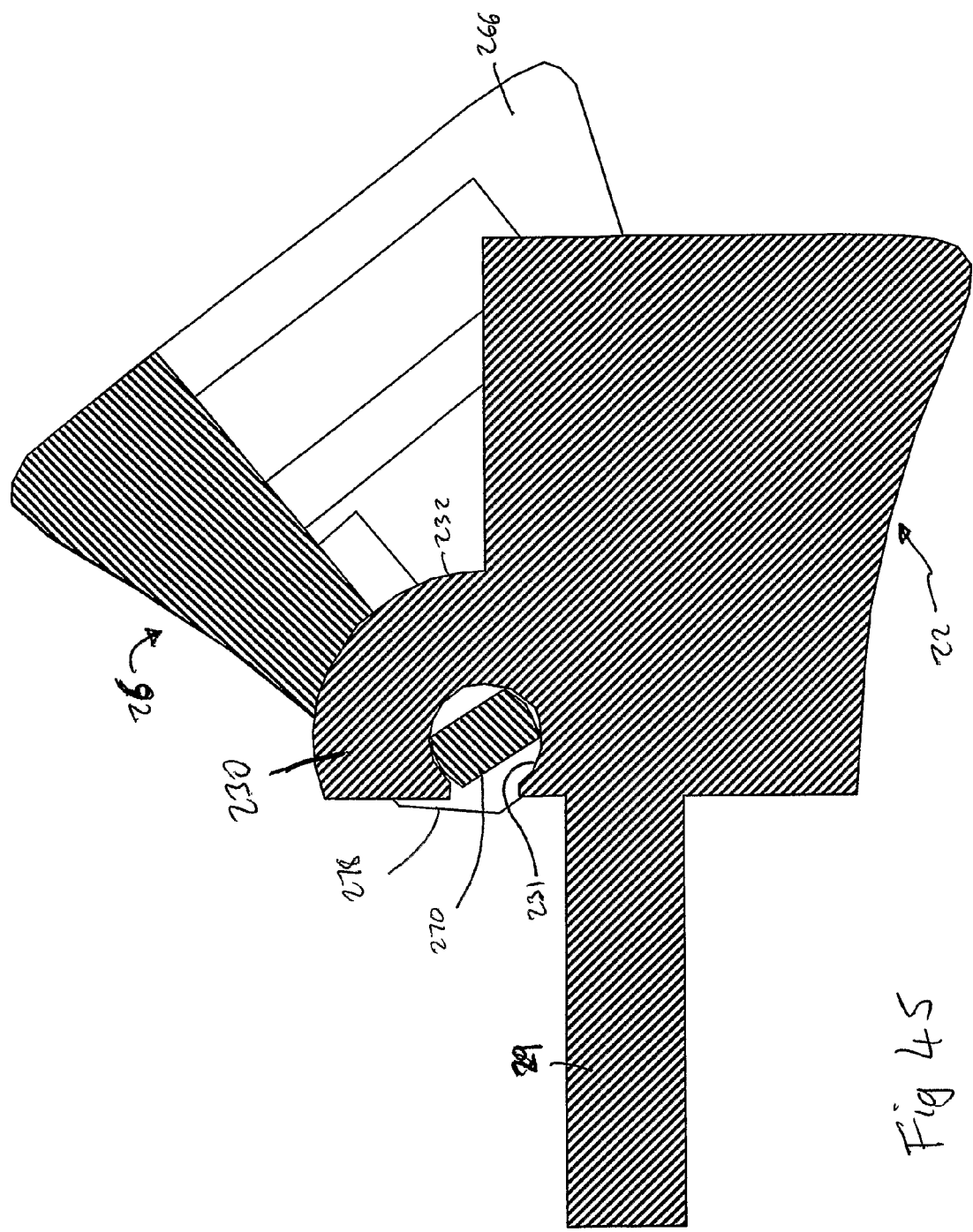
Figure 46:
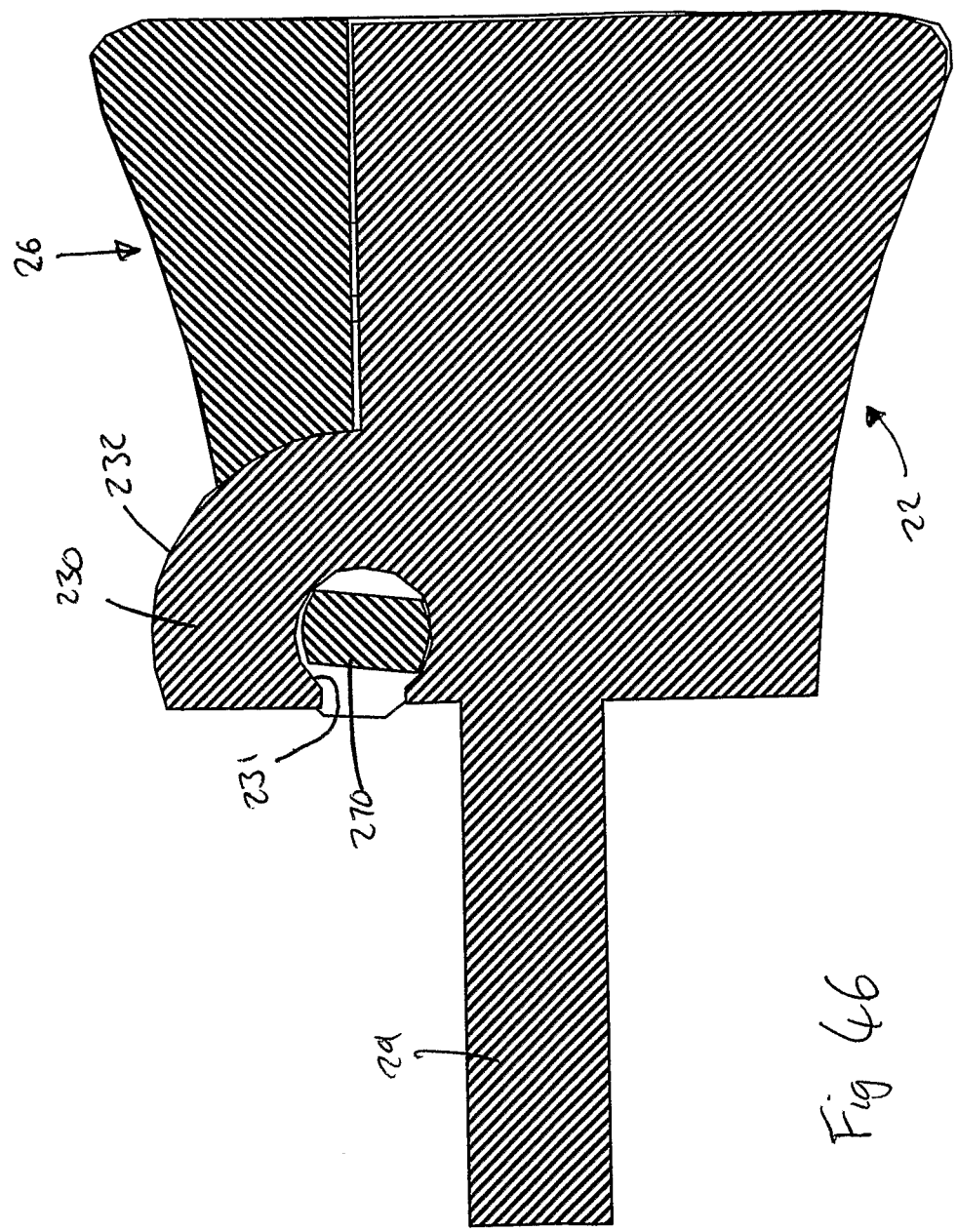
Figure 47:
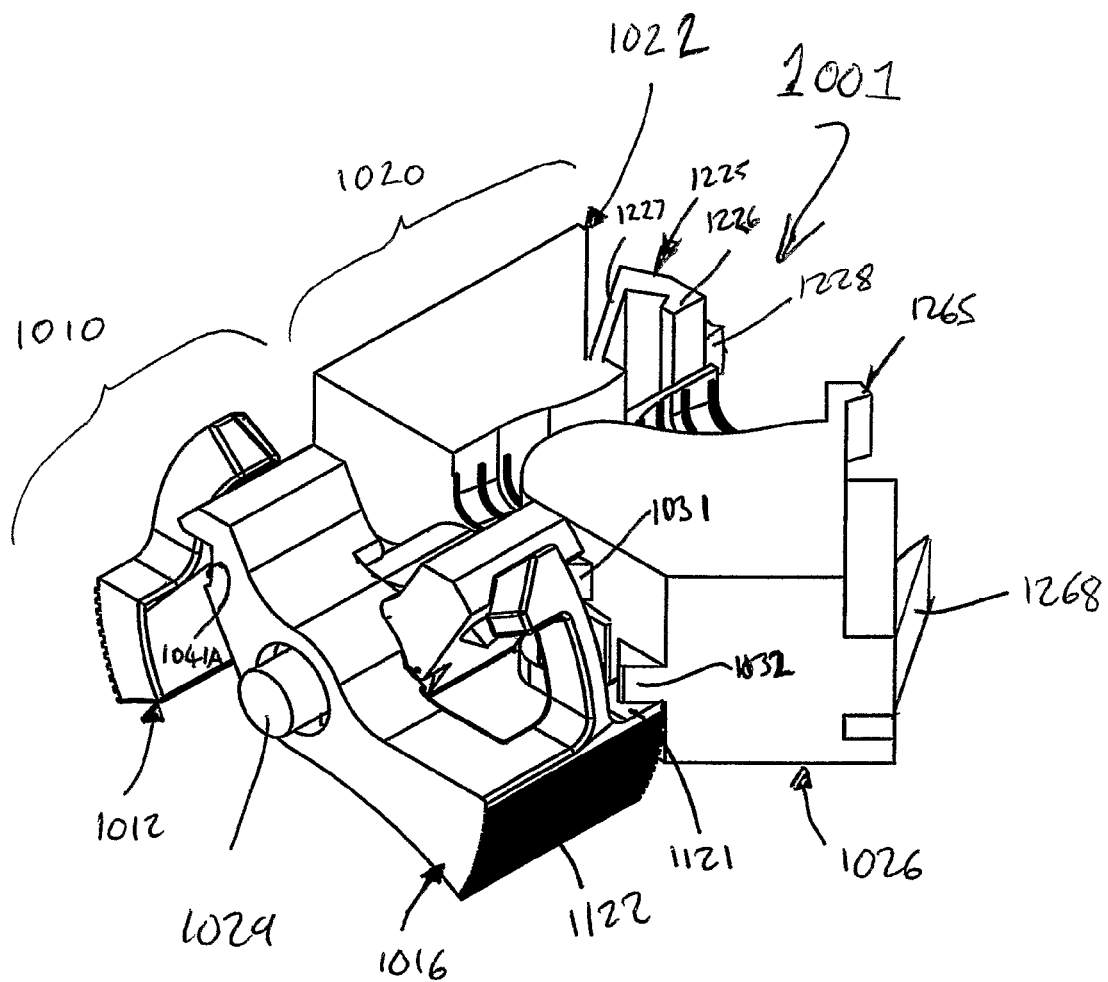
FIG. 47 is a perspective view of an alternative embodiment of an attachment device in which a clip portion and a gripping portion are both shown in their open positions.
Figure 48:
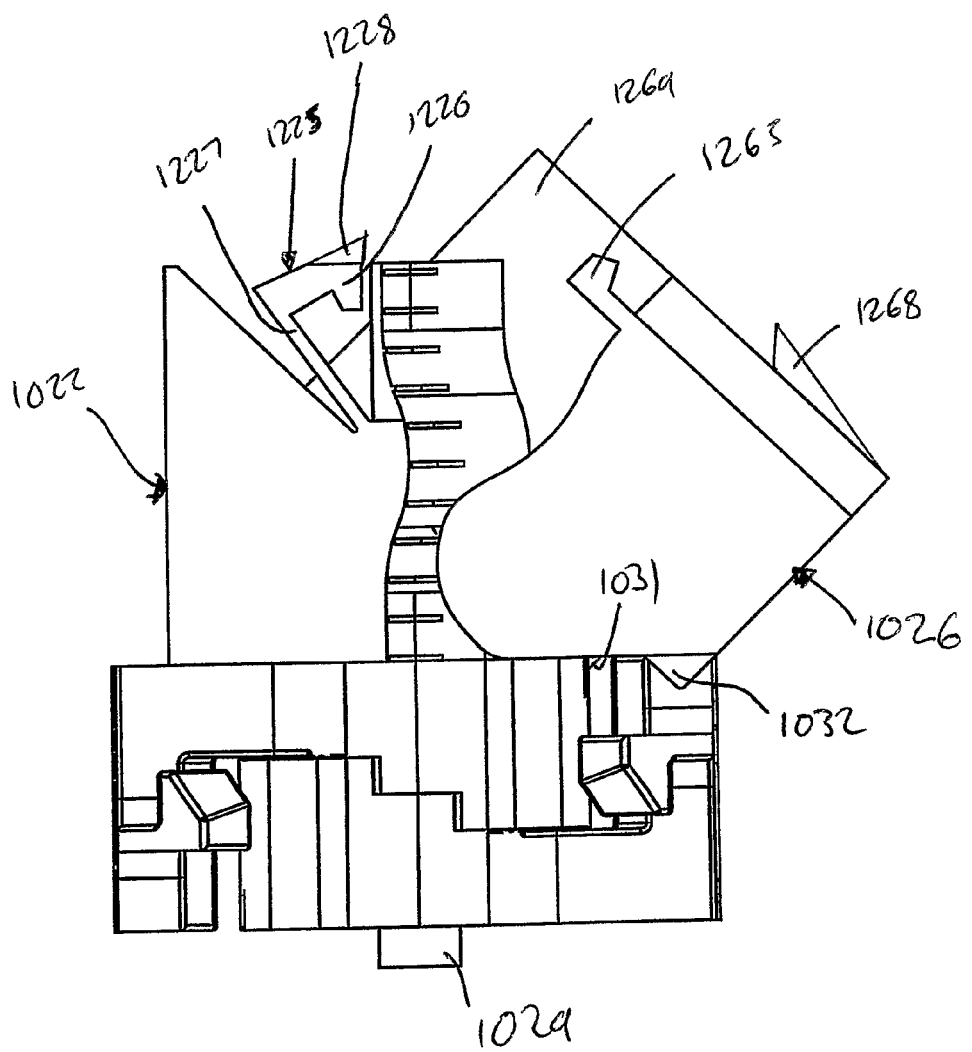
FIG. 48 is a plan view from above corresponding to FIG. 47.
Figure 49:
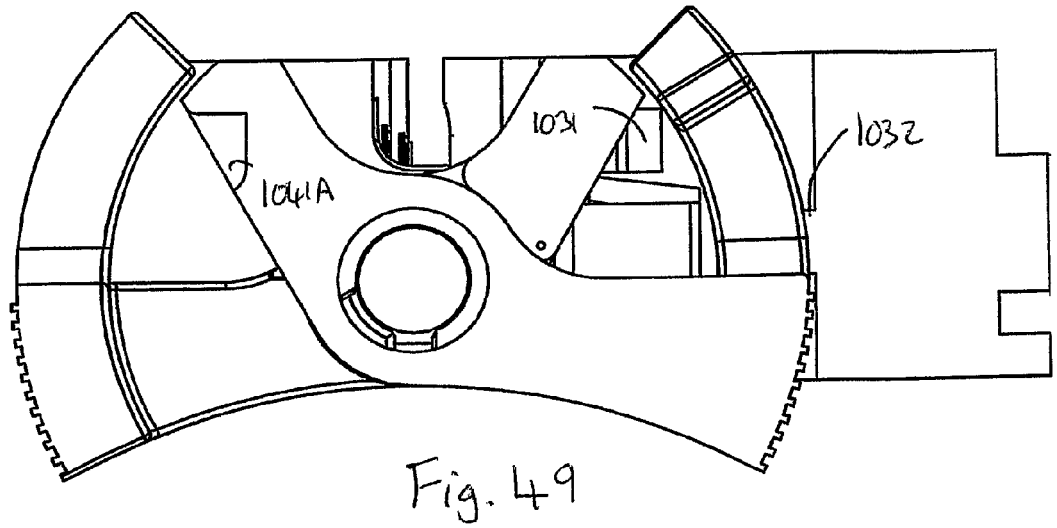
FIG. 49 is a first end view corresponding to FIG. 47.
Figure 50:
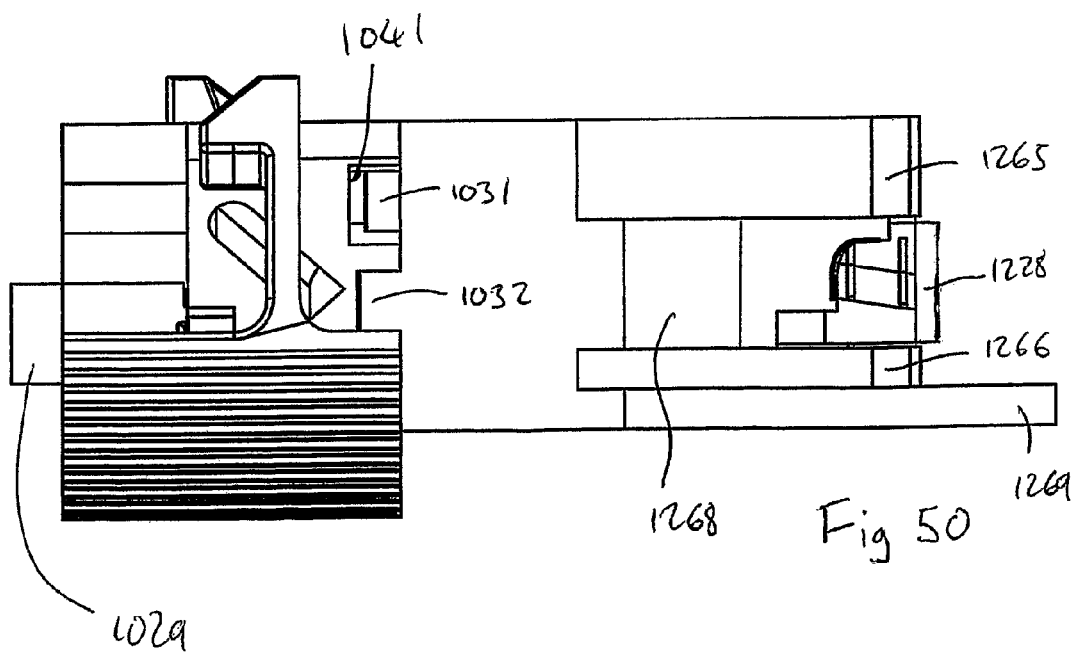
FIG. 50 is a first side view corresponding to FIG. 47.
Figure 51:
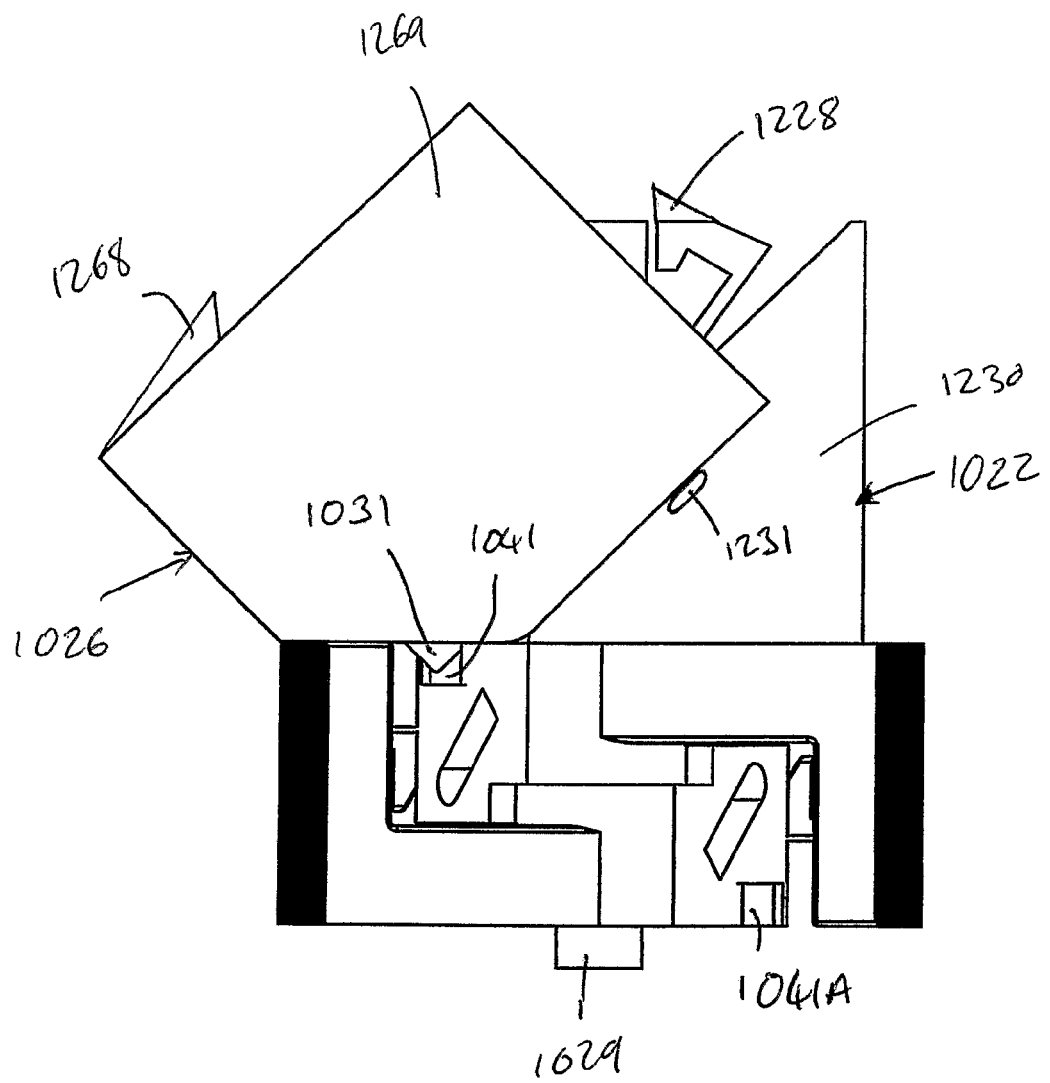
FIG. 51 is a bottom plan view corresponding to FIG. 47.
Figure 52:
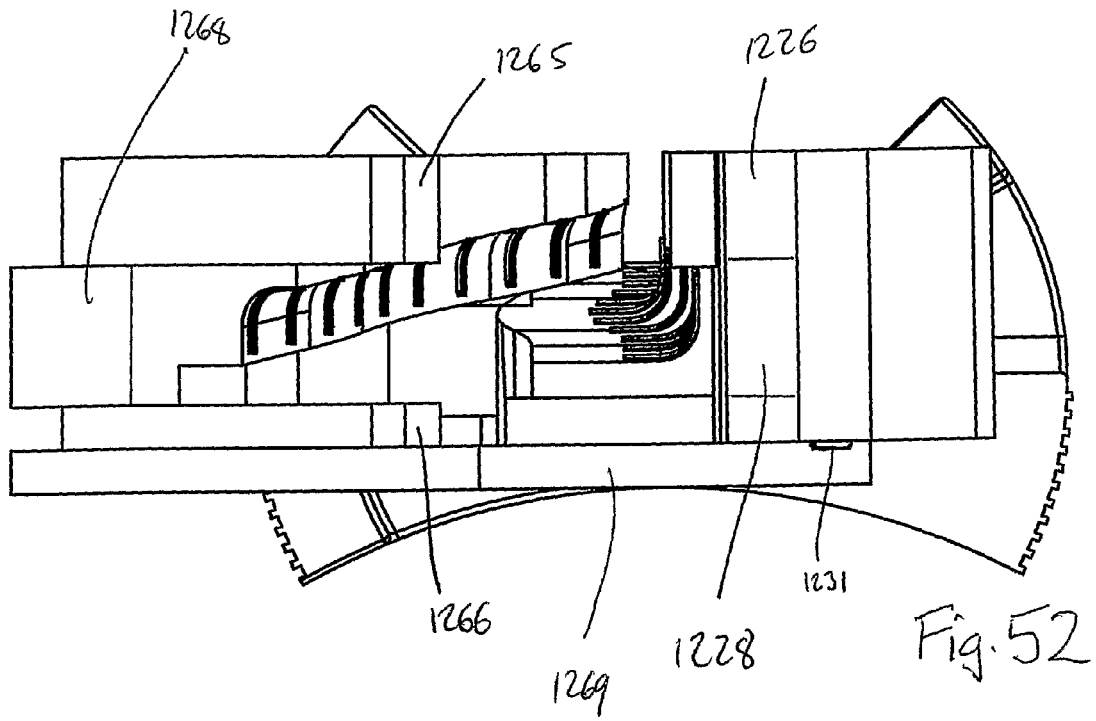
FIG. 52 is a second end view corresponding to FIG. 47.
Figure 53:
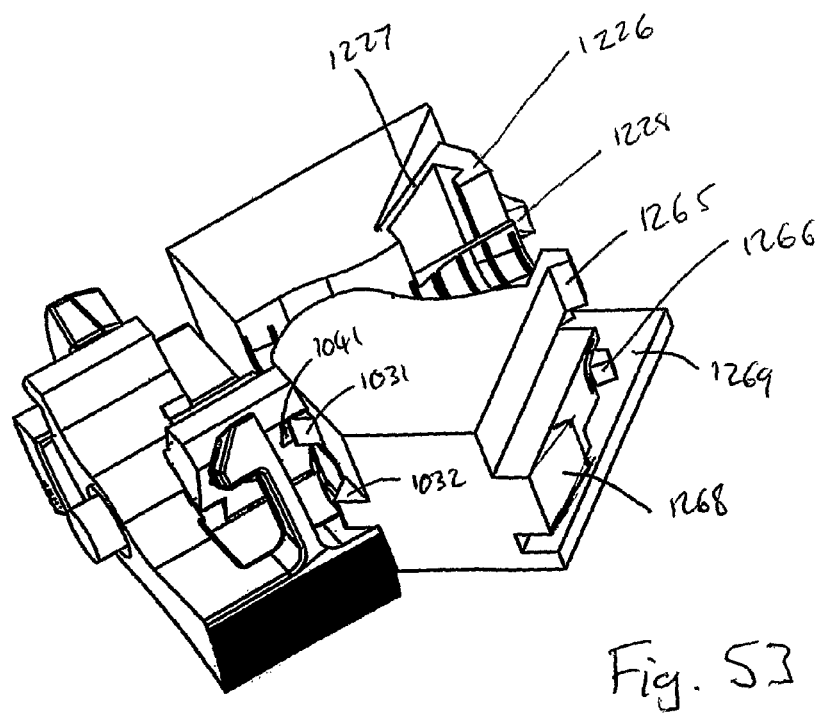
FIG. 53 is a further perspective view corresponding to FIG. 47.

In use, the first and second clip bodies 12, 16, main body 22 and movable element 26 are manufactured separately and an attachment device comprising these four elements, as illustrated in FIGS. 1 to 16 is assembled prior to use. In a preferred embodiment, the assembly is performed by first connecting the movable element 26 to the main body 22. As illustrated by FIGS. 43 to 45 which show a horizontal cross-section through the main body 22 and movable element 26 this is achieved by relatively aligning the main body 22 and movable element 26 so that the post 270 can be inserted through an opening 238 in the hinge portion 230 of the main body 22. It will be appreciated that the opposed planar surfaces 271a of the post 270 are closer together than the opposed convex part cylindrical surfaces 271 and that feeding a convex surface 271 through the opening 238 (see FIGS. 43 and 44) and then rotating the attachment element slightly (see FIG. 45) will cause the convex part-cylindrical surfaces 271 of the post 270 to engage the part-cylindrical inner surface 231 of the hinge portion 230. This arrangement allows a degree of relative pivotal motion therebetween while maintaining the post 270 captured in the hinge portion 230 unless the movable element 26 is rotated sufficiently for one of the convex part cylindrical surfaces 271 to align with the opening 238 (which would allow the post 270 to be removed from the hinge portion 230). However, as will be described in due course, the device is structured so that once it is assembled the moveable element 26 cannot be inadvertently rotated sufficiently to allow post 270 to be removed from the hinge portion 230. FIGS. 45 and 46 show, in horizontal cross section, the gripping portion 20 of the attachment device in open and closed (i.e. gripping) configurations respectively. FIGS. 5 and 15 show views from beneath the device which include the gripping portion 20 in open and closed configuration, respectively. During assembly of the device the gripping portion 20 will be retained in its open position by engagement of the second abutment surface 279 with the lower side surface 239 of the moveable element 26. Because of the engagement of these surfaces 279, 239 a definite force is required to move the moveable element 26 relative to the main body 22 from the open position illustrated in FIGS. 1 to 6 and 45 to any other position.

Assembly of the device is completed by passing the attachment element 29 through the apertures 127 of the first and second clip bodies 12, 16. The clip bodies 12, 16 are mounted on the attachment element 29 so that the outer side surface 137 of the first clip body 12 is adjacent to the main body 22 and moveable element 26, and so that the outer side surface (equivalent to 137) of the second clip body is distal from the main body.

Furthermore, the clip bodies 12, 16 are mounted on the attachment element so that the inner side surface 132 of the prong support portion 128 of each clip body 12, 16 contacts the inner side surface 125 of the shank portion 124 of the other clip body 16, 12.

The first and second clip bodies 12, 16 are retained on the attachment element 29, and maintained in mutual contact by the first and second biased retaining elements 241, 242 of the attachment element. It will be appreciated that the first and second biased retaining elements 241, 242 are forced inwardly as the attachment element is passed into and through the through apertures 127 but spring outwardly to engage the part annular shoulder 150 of the second clip body 16 when the attachment element 29 is fed sufficiently far through the apertures 127. Because the part annular shoulder 150 is somewhat recessed compared to the adjacent outer side surface 137, the biased retaining elements cannot be inadvertently pressed radially inward but can be deliberately pressed radially inwardly, for example by use of pointed forceps, if it is desired to detach the clip bodies 12, 16 from the main body 22.

It will be appreciated that the clip bodies 12, 16 are mounted on the connection element so that the projecting rib 240 is located within the groove 147 (of each clip body), and so that most of the outer cylindrical surface of the connection element 29 is in snug but slidable contact with the inner cylindrical surface of the aperture 127. The projecting rib 240 is considerably laterally narrower than the groove 147 so presence of the projecting rib does not prevent rotational movement of the clip bodies 12, 16, but restricts the rotational movement of each clip body 12, 16 to approximately 60 degrees of angular extent by abutment with one of the step portions 148, 149 to prevent further relative rotation of the clip body 12, 16 and connection element 29. (The lateral width of the projecting rib causes the travel to be limited to approximately 60 degrees, despite the angular extent of the groove being approximately 90 degrees, and the fact that the lateral edges of the projecting rib 240 are not in radial planes relative to the connection element accounts for why the first and second step portions are not in radial planes relative to the through aperture, since flush abutment of the lateral edges of the projecting rib 240 and the step portions is desirable.)

The interaction of the projecting rib 240 and groove 147 thus limits rotation of the clip bodies so that, in use, they cannot move beyond the open and closed positions of the clip portion 10.

Upon assembly, the first and second clip bodies 12, 16 are placed in the open position of the clip portion 10 (as shown in FIGS. 1 to 10), that is, with the clasping elements 135 of the clasp portion 133 spaced apart and with the bottom surface of each clip body 12, 16 somewhat parallel to the basal surface 228 of the main body. It will be appreciated that in the open position of the clip portion 10, the first and second prongs 13, 17 do not extend downwardly further than the bottom surfaces of the clip bodies 12, 16. Thus the bottom surface of each clip body effectively provides a shielding surface 139 which prevents the prong mounted to the other clip body from inadvertently contacting other objects. Thus renders the clip portion 10 effectively "sharps-safe" when in the open position.

It will further be appreciated that in the open position of the clip portion 10 the restraining projection 129 provided on the inner side surface 132 of the prong support portion 128 of each clip body 12, 16 is located just above the shank portion 124 (and/or boss 126) of the other clip body (see, eg. FIGS. 1 and 3). In order to close the clip portion 10 the edge of each shank portion 124 (and/or boss 126) must ride over the projection. This provides a retaining mechanism for retaining the clip portion in the open position until a predetermined force is applied. Such a retaining mechanism reduces the likelihood of inadvertently closing or partially closing the clip portion 10, and helps retain the open clip portion 10 in a sharps-safe configuration. Other retaining mechanisms could be employed, see for example the description of the alternative embodiment of FIGS. 47 to 78.

When the clip bodies 12, 16 are retained on the attachment element 29 and the gripping portion 20 is in its open configuration, the outer side surface 137 of the shank portion 124 of the first clip body 12 engages (and is at least partially substantially co-planar with) the first abutment surface 278 of the movable element 26 of the gripping portion 20. This engagement helps retain the movable element in position and prevent inadvertent closure of the gripping portion 20. Furthermore, the position of the outer side surface 137 prevents rotation of the movable element away from the closed position past the open position which could result in the hinge post 270 being able to exit the opening 238 of the hinge portion 230. Thus, with the attachment device assembled, the post 270 is retained in the hinge portion 230 and the hinge assembly effectively functions (through the limited available range of rotation) similarly to a hinge comprising a cylindrical post in a cylindrical cavity.

In use, the assembled attachment device, with clip portion 10 and gripping portion 20 in their open positions (as illustrated in FIGS. 1 to 6) is brought to the site where it is to be used, for example to attach a catheter tube to a patient.

A catheter tube is first loosely clipped to the attachment device by insertion of the catheter tube between the projection 277 (on the movable element 26) and the main body. The projection 277 is formed so that when the gripping portion 20 is in its open position the distance between the projection and the main body is fractionally smaller than the outside diameter of a catheter tube with which the attachment device is to be used. This allows a catheter tube to be gently gripped by the attachment device when the gripping portion is in its open position.

The attachment device 1 is brought into contact with the patient at the location where it is to be attached, so that at least part of the shielding surfaces 148, 149 are at the point of intended attachment.

The position of the catheter tube can then be fine tuned if required, before closure of the gripping portion 20 securely fixes the catheter tube in the desired position.

Closure of the gripping portion is performed by merely moving the movable element 26 from the open position to the closed position. This results in the upper and lower clasp elements 265, 266 on the movable element engaging and securing to the complementary upper and lower clasp elements 225, 226 of the main body 22, thus securing the gripping portion in its closed position and securing the tube to the attachment device 1.

The clip portion 10 is then operated to its closed position, rotating each of the clip bodies approximately 60 degrees about the attachment portion and driving the prongs into the tissue of the patient. The clasp elements 133 of the clip bodies engage, locking the clip portion 10 in the closed position, and also passing around (but not substantially bearing upon) the catheter tube.

If desired the clip portion 10 could be operated before the gripping portion 20.

A preferred embodiment of an attachment device is much smaller than the illustrations might suggest, and may have a total length of 2 cm or 3 cm and, in use, stand proud of the skin of a user by about 1.5 cm or 2 cm.

The prongs may penetrate approximately 0.5 cm into the tissue of the patient.

Of course, different sizes can be provided for different purposes or use under different circumstances and/or to accommodate catheter or surgical drain tubes of different diameters. It is also envisaged that a ratchet-type mechanism, such as that typically used on cable ties or zip ties, could be used to lock the gripping portion. This could provide facility for a single attachment device to have a channel which may be closed to different degrees to accommodate different sizes of tube. Many variations are possible without departing from the scope of the invention.

With reference to FIGS. 47 to 78 an alternative embodiment will be described. It will be appreciated that this alternative embodiment has many similarities to the embodiment of FIGS. 1 to 46 and only the differences will be described in detail, although details that the two embodiments have in common may be mentioned to enhance clarity.

There are a number of notable differences between the embodiment of FIGS. 47 to 78, generally designated as attachment device 1001, and the attachment device 1 illustrated in FIGS. 1 to 46.

First, the attachment device 1001 provides interaction between a gripping portion 1020 and a clip portion 1010 so that when both the gripping portion 1020 and clip portion 1010 are in their open positions (as illustrated in FIGS. 47 to 53) the clip portion 1010 cannot be closed. This means that the sharp ends of the prongs (not shown) cannot be exposed prior to operation of the gripping portion 1020, and the attachment device 1001 is thus effectively locked in its clip open "sharps-safe" configuration prior to use.

Second, the embodiment 1001 is provided with a different clasp mechanism on the gripping portion 1020. The clasp mechanism does not project beyond the top or bottom of the attachment device and is arranged so that it can be unfastened by application of a force in the direction opposite to the direction in which a force must be applied to close the gripping portion 1020 (that is, by effectively forcing apart a main body and moveable element of the gripping portion).

In the embodiment 1001 the clip portion comprises first and second clip bodies 1012, 1016 respectively mounted upon an attachment element 1029 which is in the form of a rod which extends forwardly from a main body 1022 of the gripping portion 1020 (and which is substantially identical to the attachment element 29). A movable element 1026 of the gripping portion 1020 is attached to the main body via a hinge arrangement 1030 so that it may be moved between an open position and a closed position of the gripping portion 1020. (The hinge arrangement 1030 is not shown in detail, but corresponds generally to the corresponding hinge of the attachment device 1, and the moveable element includes a hinge post 1270 similar to the hinge post 270.) In this respect the embodiment 1001 is similar to the embodiment 1 of FIGS. 1 to 46. However, in the embodiment 1001 the movable element 1026 is provided with first and second locking projections 1031, 1032 which are adapted to engage respectively with the first and second clip bodies 1012, 1016 in order to prevent operation of the clip portion 1010 when the gripping portion 1020 is in its open configuration.

Figure 54:
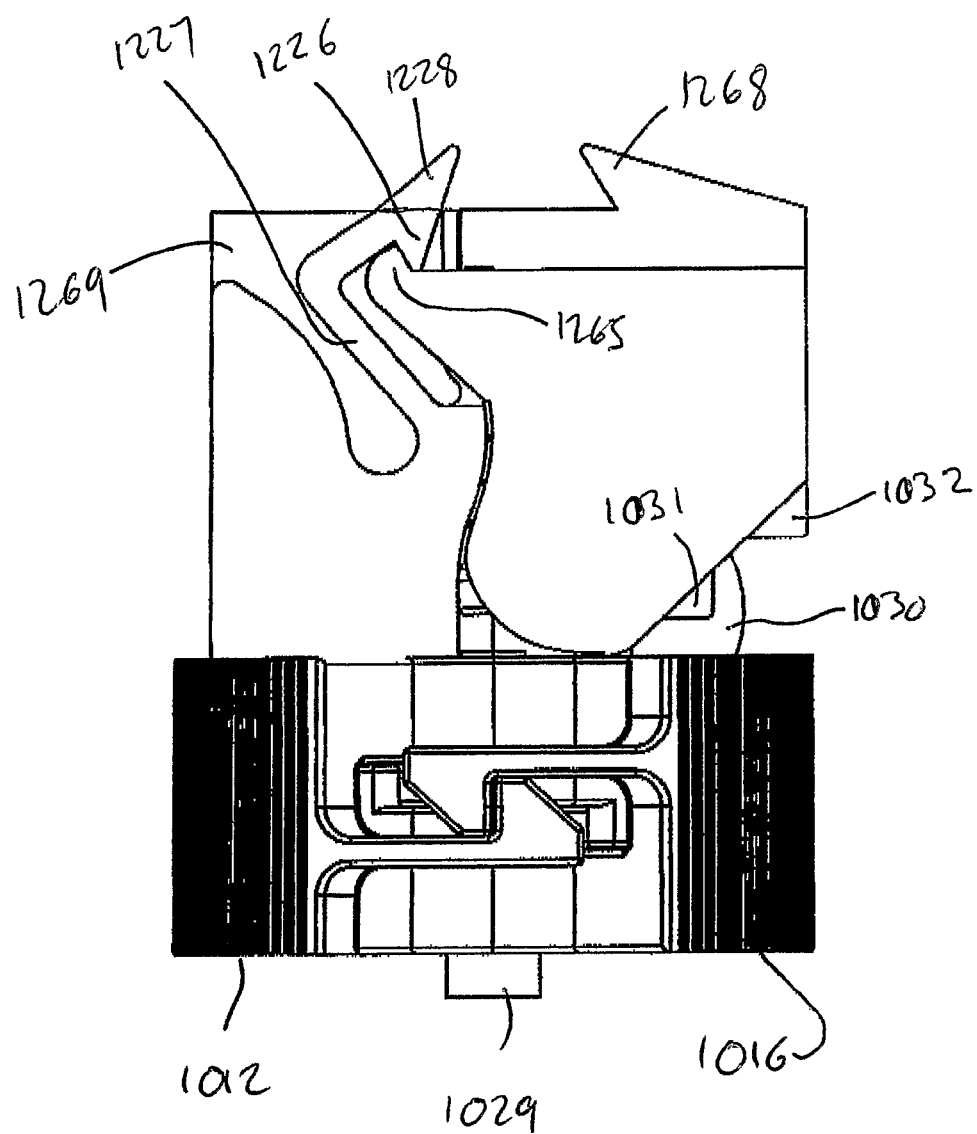
FIG. 54 is a plan view from above of the embodiment of FIGS. 47 to 53 with the clip portion and gripping portion shown in their closed positions.
Figure 55:
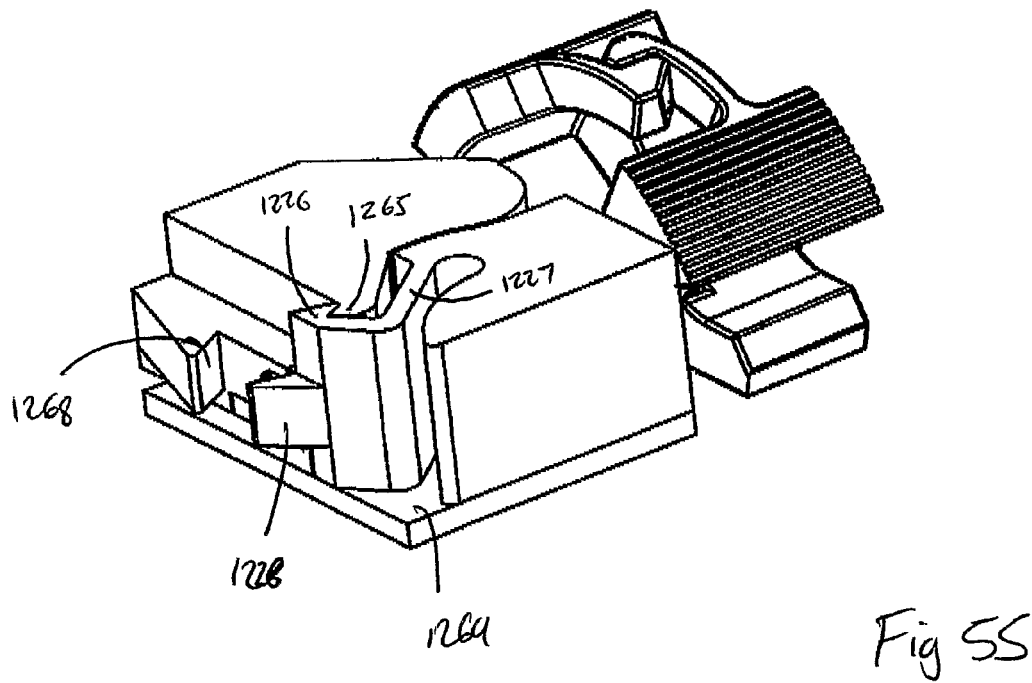
FIG. 55 is a perspective view corresponding to FIG. 54.

The locking projections 1031, 1032 project from a substantially vertical front/side wall of the movable element 1026 which is in close proximity to the clip bodies 1012, 1016 when the gripping portion 1020 is in its open position (see for example FIG. 47) and at least part of which is spaced apart from the clip bodies 1012 when the gripping portion 1020 is in its closed configuration (see for example FIG. 54). The first locking projection 1031 is adapted to engage in a recess 1041 provided on a mounting portion of the first clip body 1012. (The recess 1041 is not evident in FIG. 47 or 49 so a similar recess, provided on the second clip body 1016, is designated 1041A; it will be appreciated that for convenience of manufacture and assembly it is preferred that the first and second clip bodies are identical, even though the recess 1041A on the second clip body 1016 will not be used.)

The second locking projection 1032 is adapted to engage an upper surface 1121 of an operating portion 1122 of the second clip body 1016. In the illustrated embodiment the clip bodies 1012, 1016 are similar to the clip bodies 12, 16 but differ in the provision of the recesses 1041, 1041A, and the fact that clip bodies 1012, 1016 are somewhat "built-up" bulkier and less tapered in the region of the recesses 1041, 1041A.

It will be appreciated that in the embodiment of FIGS. 1 to 46 the movable element 26 is positioned (see for example FIG. 2) so that it is in close proximity to only the first clip body 12. In the attachment device 1001 the construction differs somewhat in that the movable element 1026 may be regarded as being to the opposite side of the device so it is in close proximity to the mounting portion of the first clip body 1012 and to the operating portion of the second clip 1016. In order to accommodate this change the main body 1022 and movable element 1026 may be regarded as being, in some respects, effectively mirror images of the main body 22 and movable element 26 respectively. An alternative to "reversing" positions of the main body 1022 and movable element 1026 would be to use clip bodies which are effectively mirror images of the illustrated clip bodies 1012, 1016.

The locking projections 1031, 1032 prevent rotational movement of the first and second clip bodies 1012, 1016 until the gripping portion 1020 is operated into its closed position. It will therefore be appreciated that the clip portion 1010 is effectively locked in its open, sharps-safe, position until the gripping portion 1020 is moved from its open position to its closed position. Once the gripping portion 1020 is moved from its open position to its closed position, as illustrated in FIG. 54, the first and second locking projections 1031, 1032 are taken out of contact with the first and second clip bodies 1012, 1016 and the clip portion 1010 can operated in a similar manner to the clip portion 10 of the attachment device 1.

Figure 56:
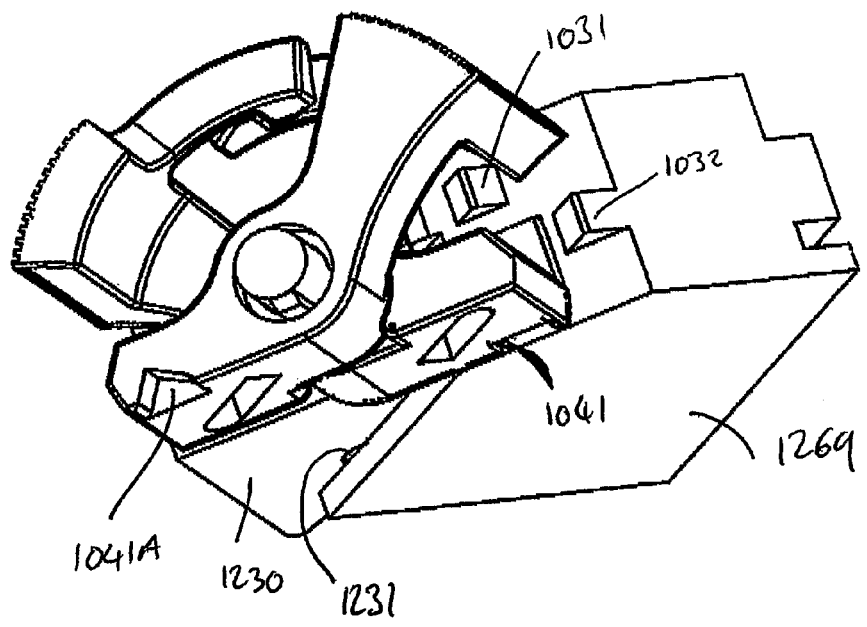
FIG. 56 is a perspective view from one end and below corresponding to FIGS. 54 and 55, but with the gripping portion in its open position.
Figure 57:
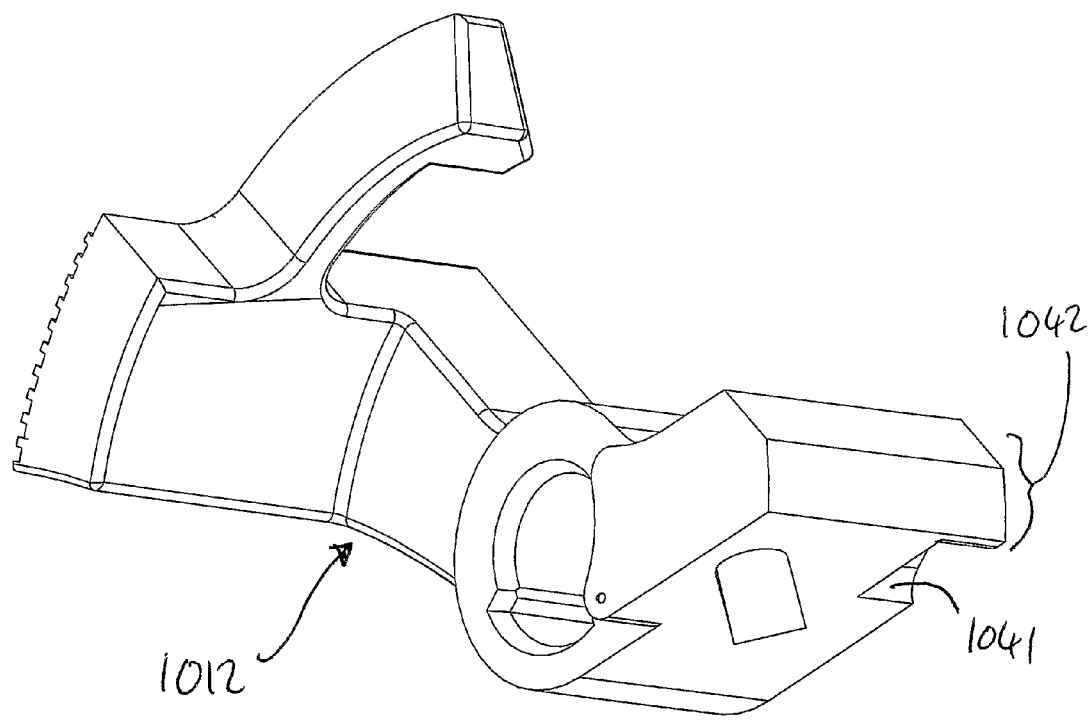
FIG. 57 is a perspective view of a clip body which forms part of the clip portion of the embodiment of FIGS. 47 to 56.
Figure 58:
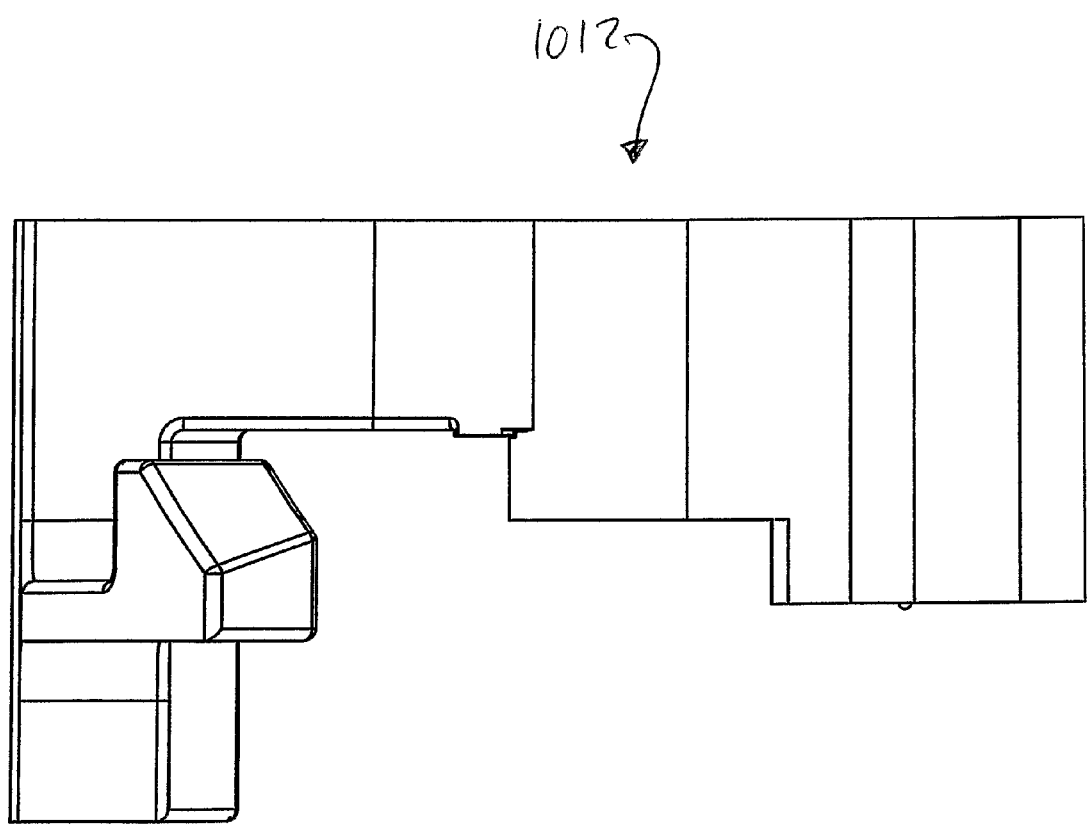
FIGS. 58 to 62 are alternative views of the clip body of FIG. 57.
Figure 59:
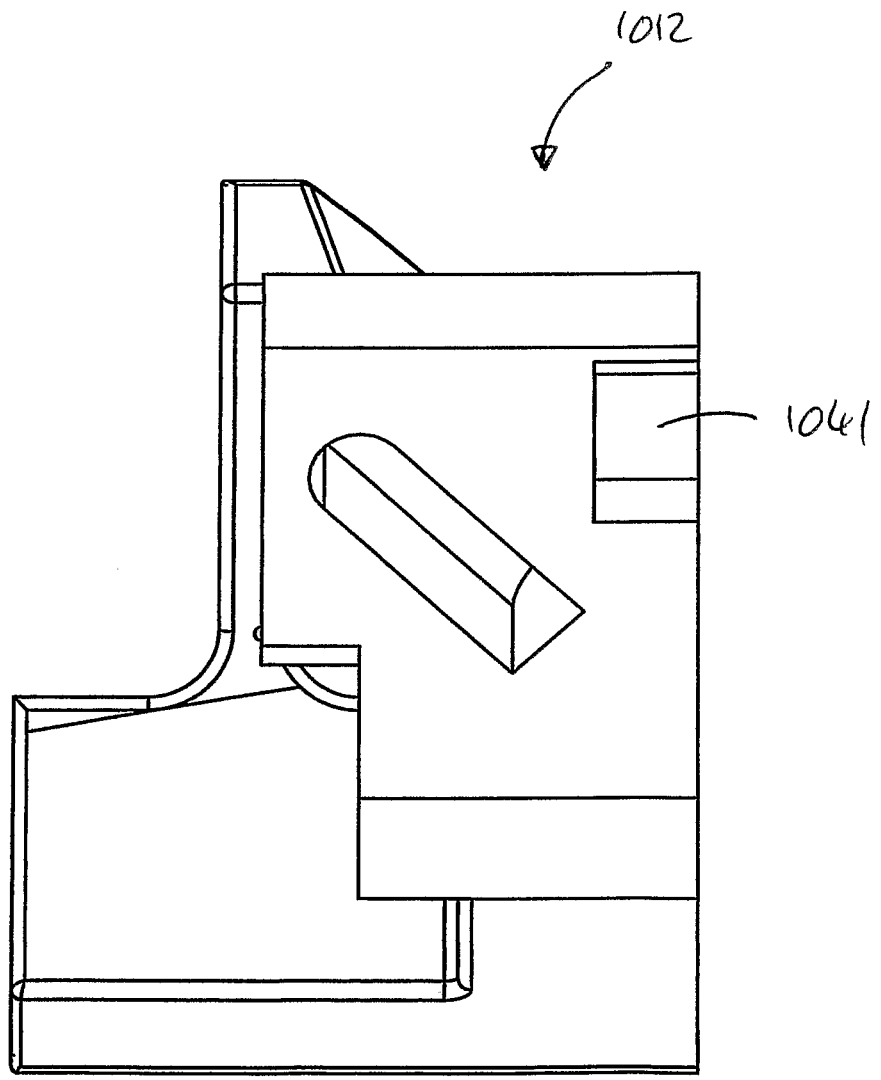
Figure 60:
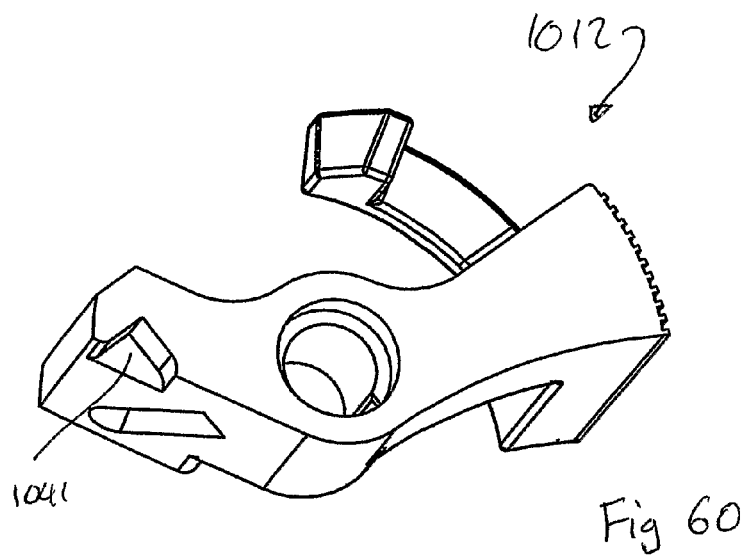
Figure 61:
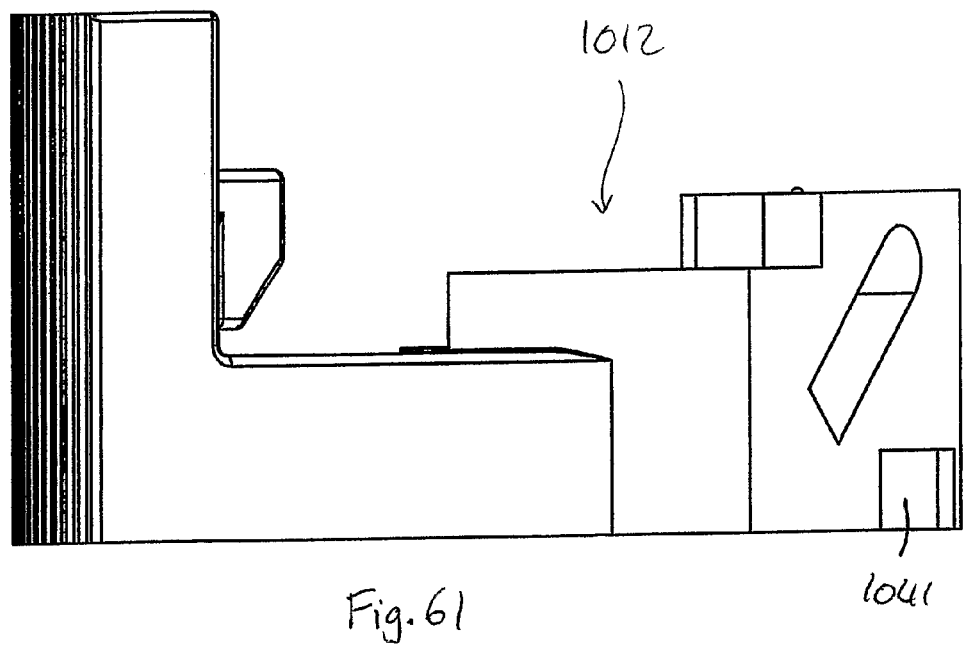
Figure 62:
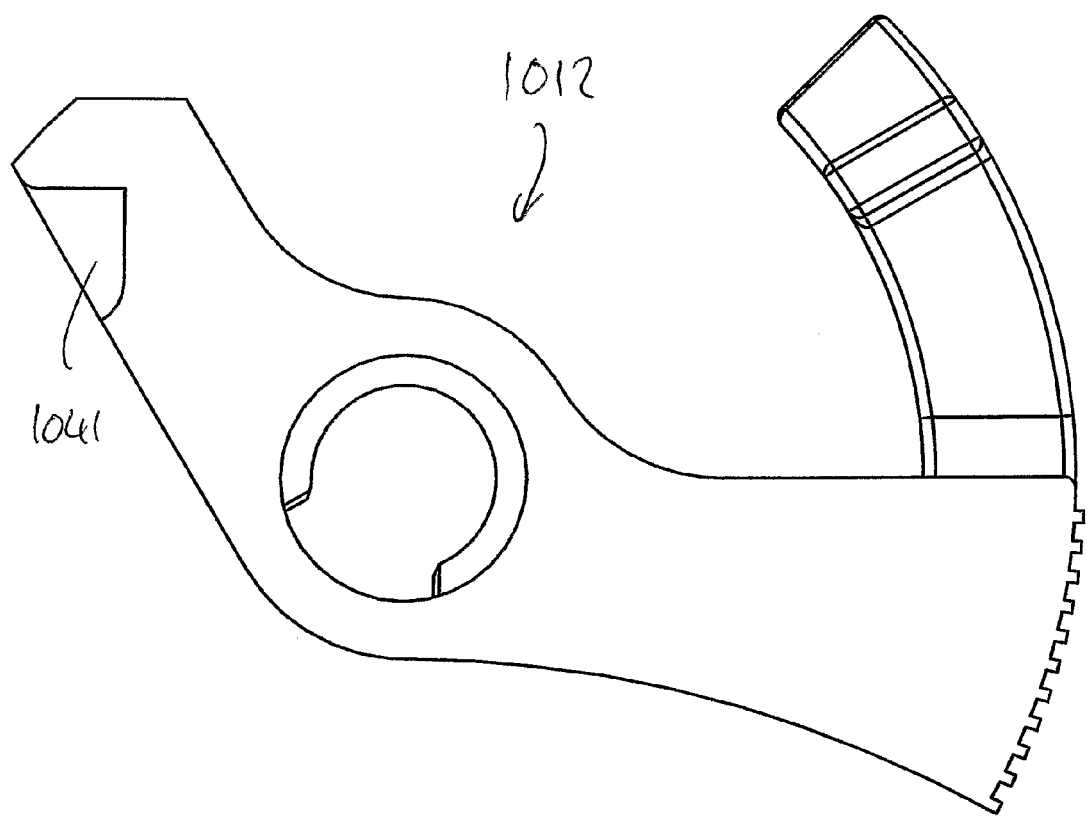
Figure 63:
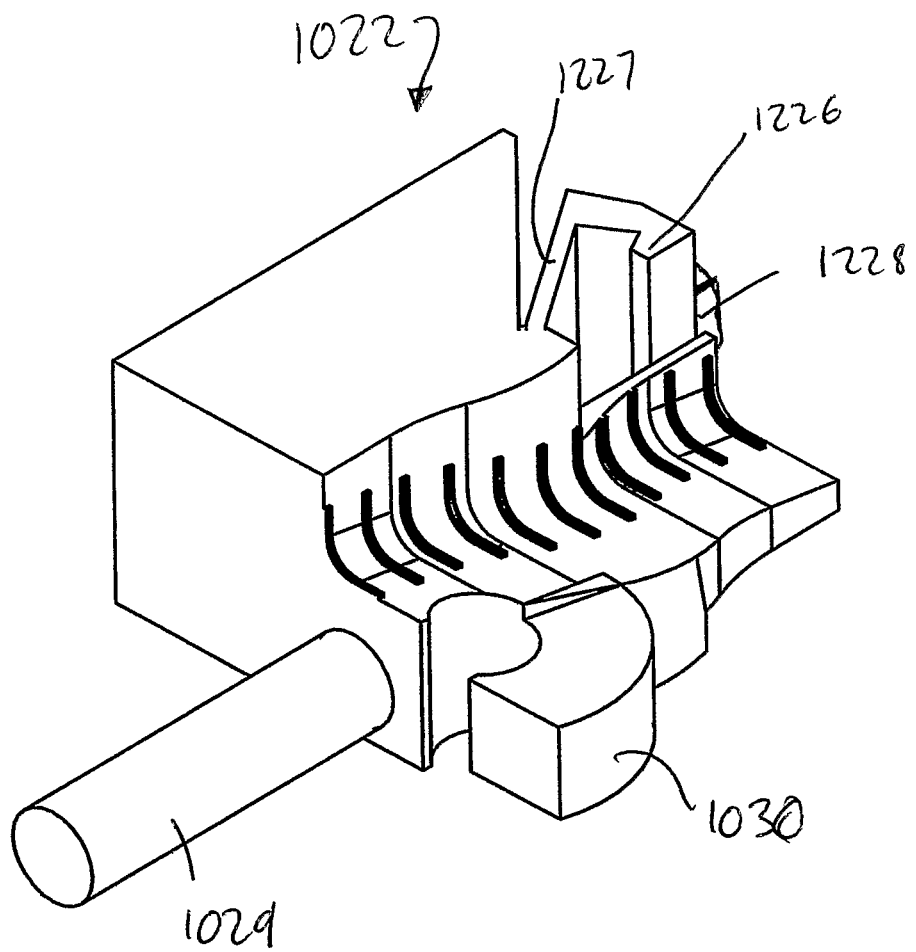
FIG. 63 is a perspective view of a main body of the gripping portion of the embodiment of FIGS. 47 to 56.
Figure 64:
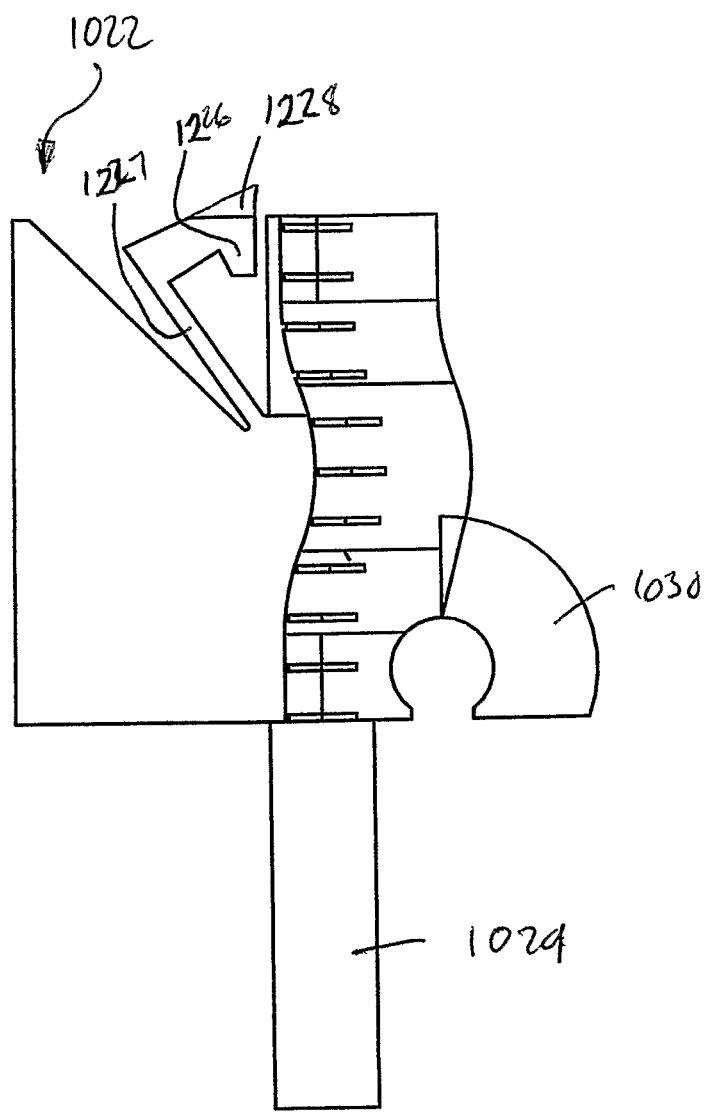
FIG. 64 is a plan view from above of the main body of FIG. 63.
Figure 65:
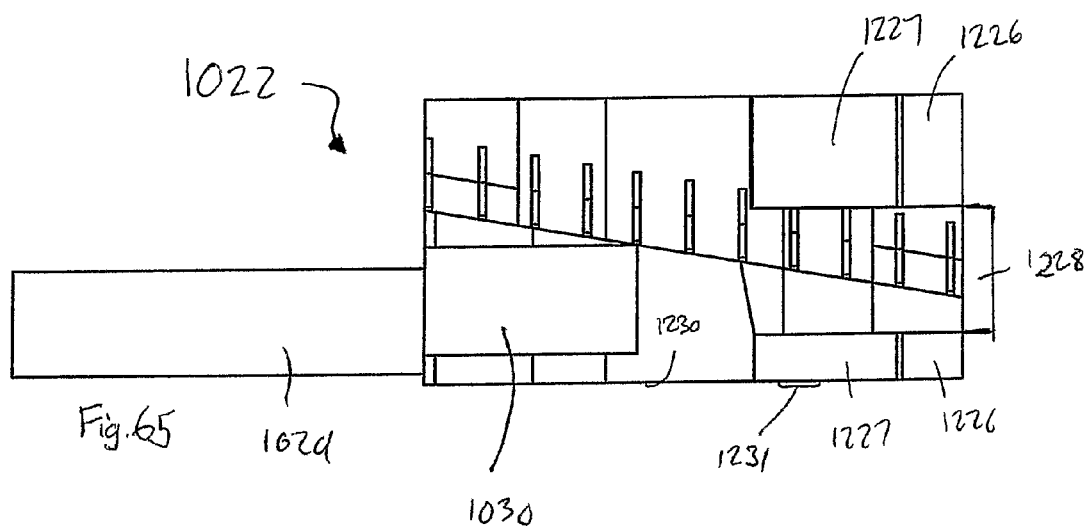
FIG. 65 is a first side view of the main body of FIG. 63.
Figure 66:
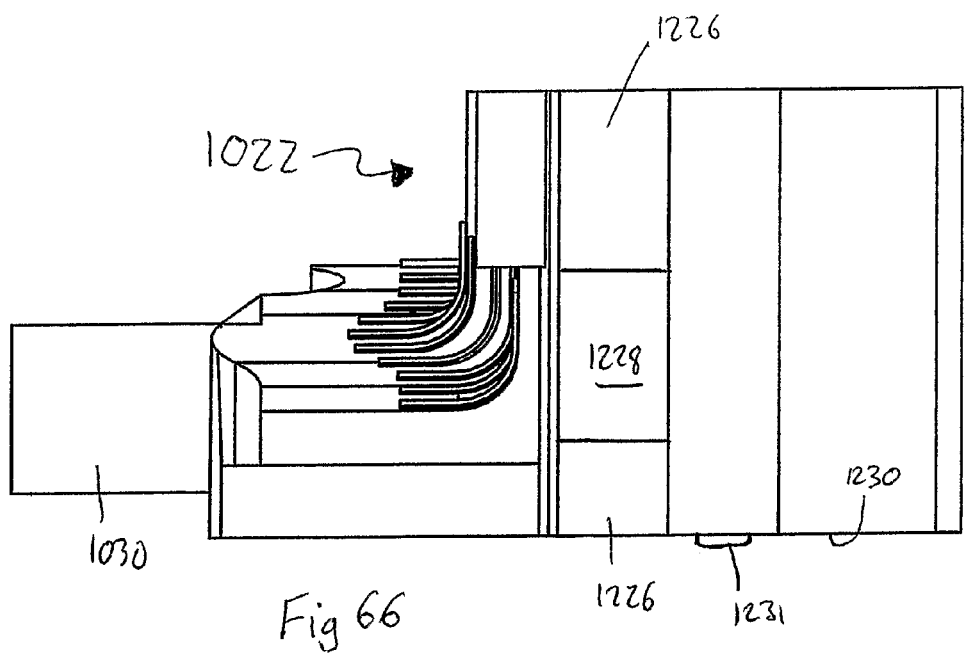
FIG. 66 is a first end view of the main body of FIG. 63.
Figure 67:
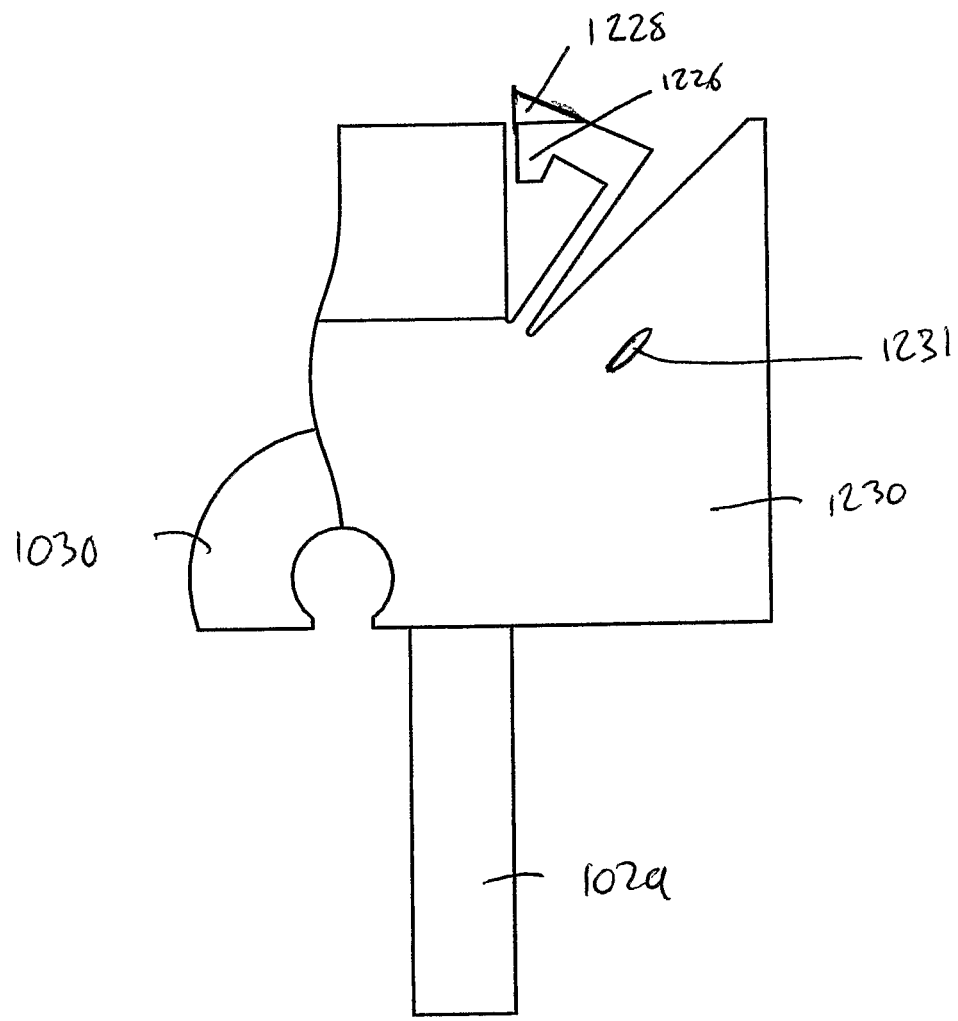
FIG. 67 is a plan view from below of the main body of FIG. 63.
Figure 68:
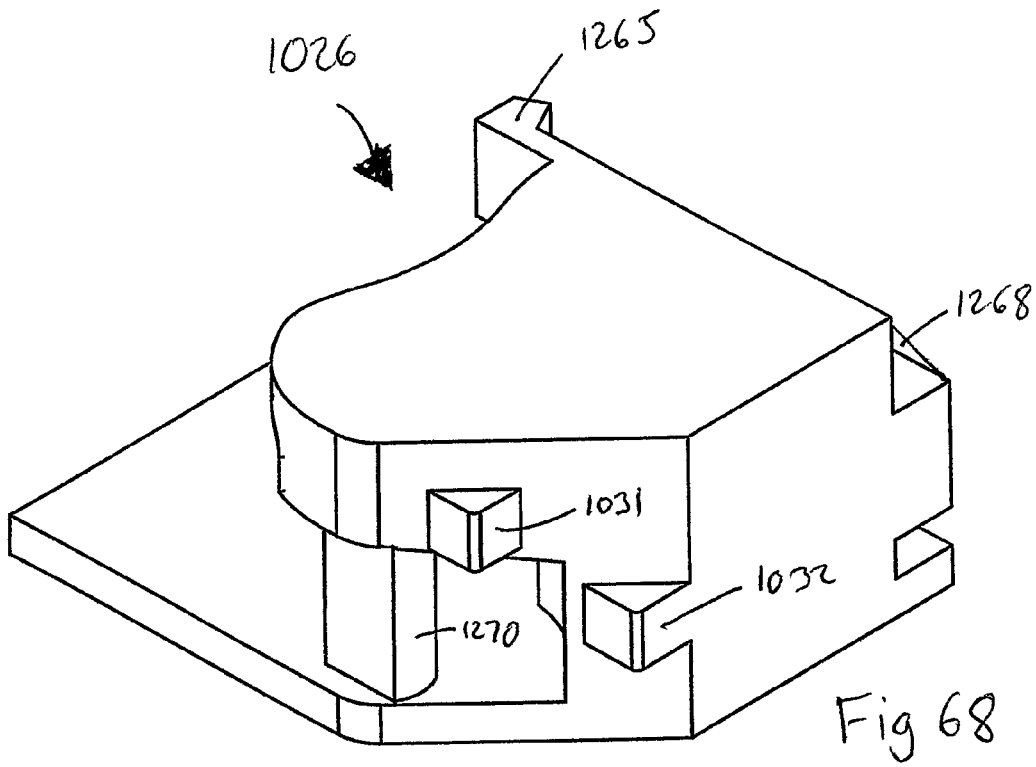
FIGS. 68 and 69 are perspective views from above of a movable element of the gripping portion of the embodiment of FIGS. 47 to 56.
Figure 69:
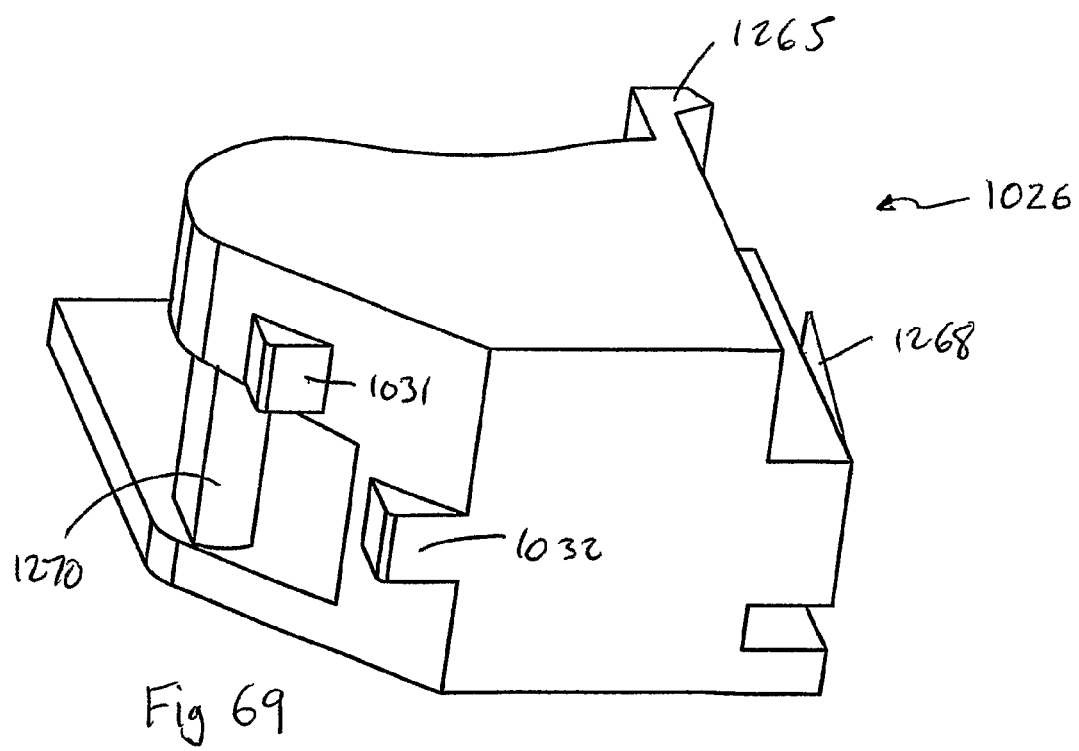
Figure 70:
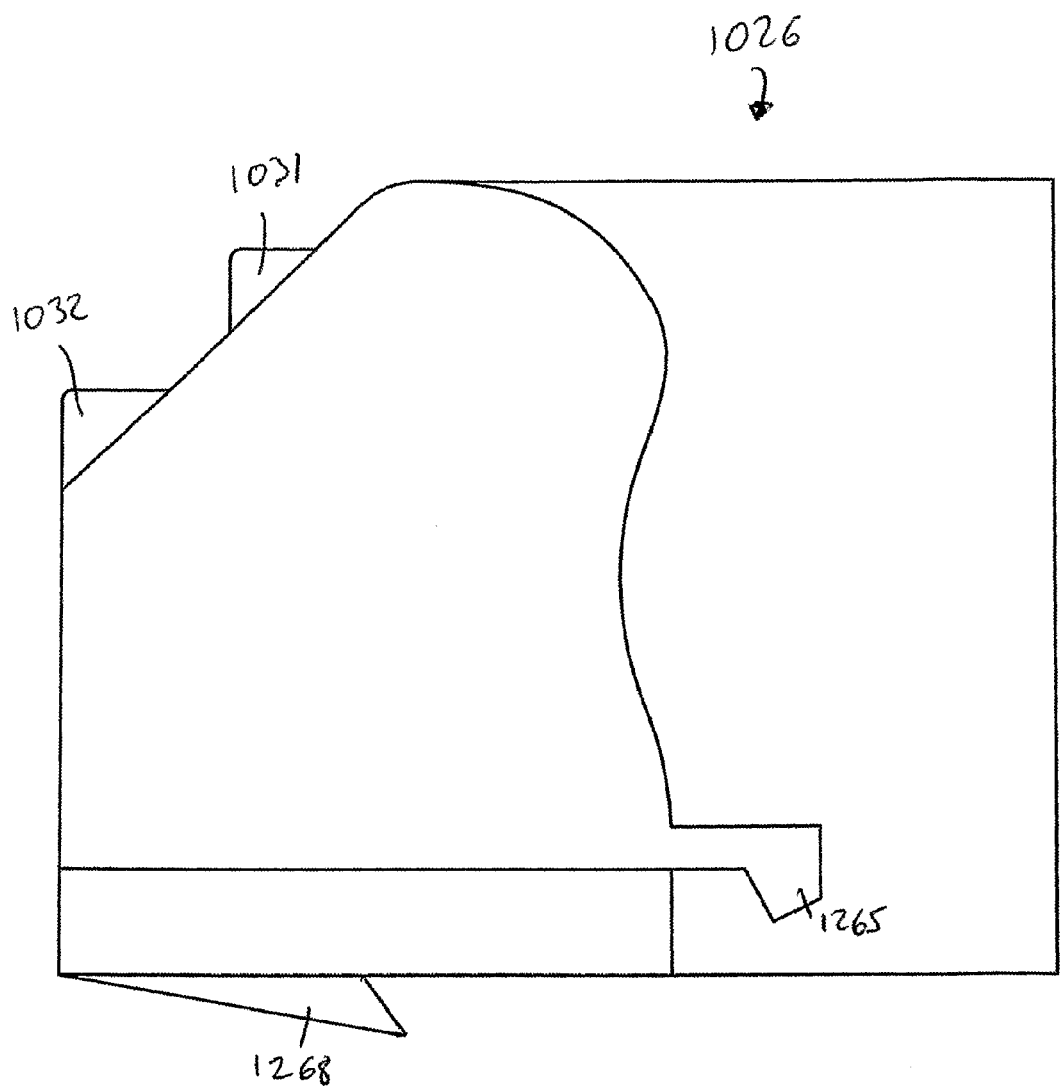
FIG. 70 is a plan view from above of the movable element of FIG. 60.
Figure 71:
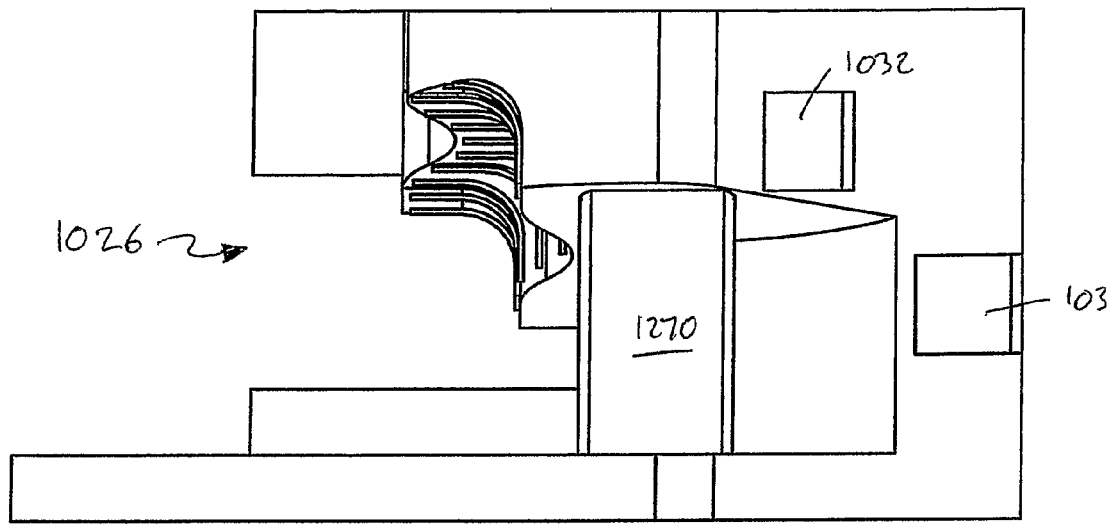
FIG. 71 is a first end view of the movable element of FIGS. 68 and 69.
Figure 72:
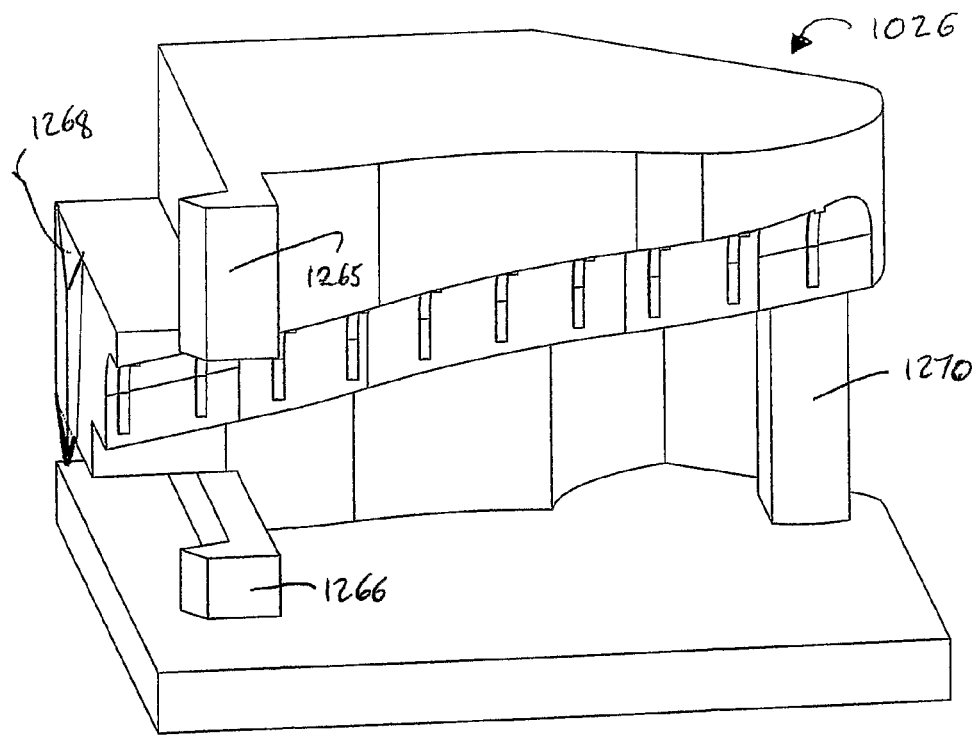
FIG. 72 is a perspective view from above and one side of the movable element of FIGS. 68 and 69.
Figure 73:
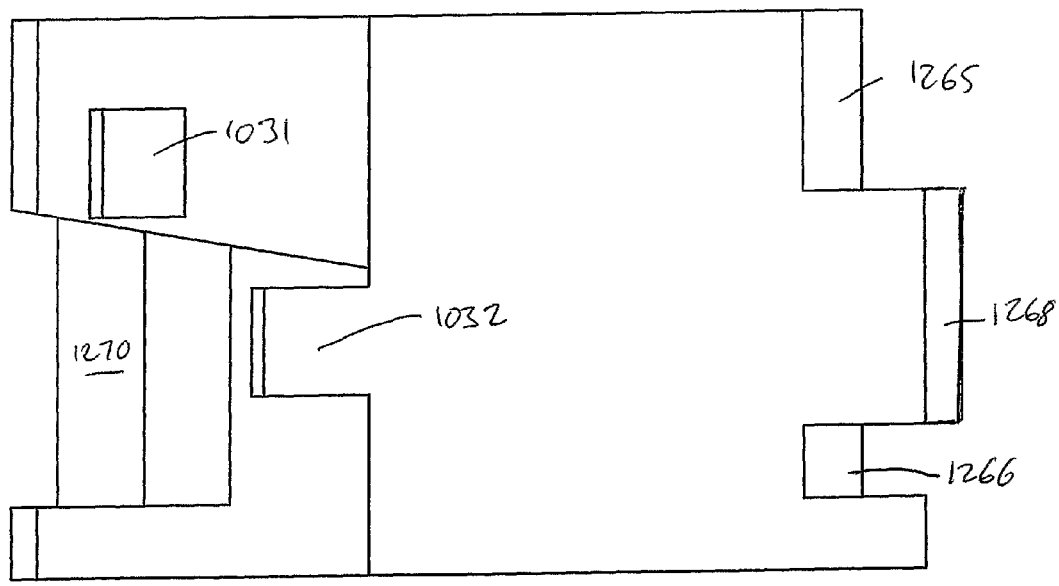
FIG. 73 is a first side view of the movable element of FIGS. 68 and 69.
Figure 74:
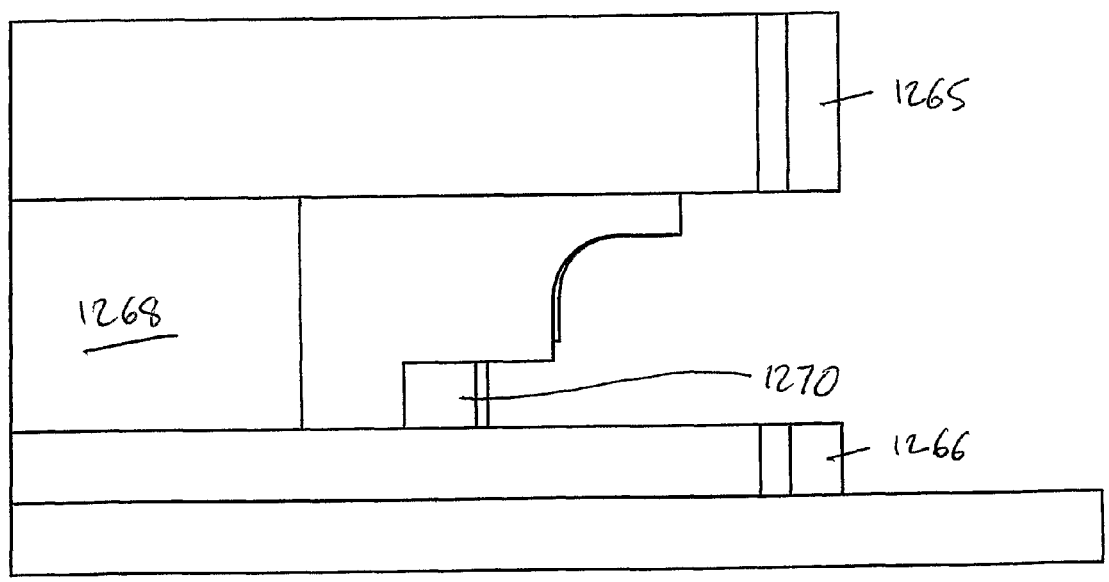
FIG. 74 is a second end view of the movable element.
Figure 75:
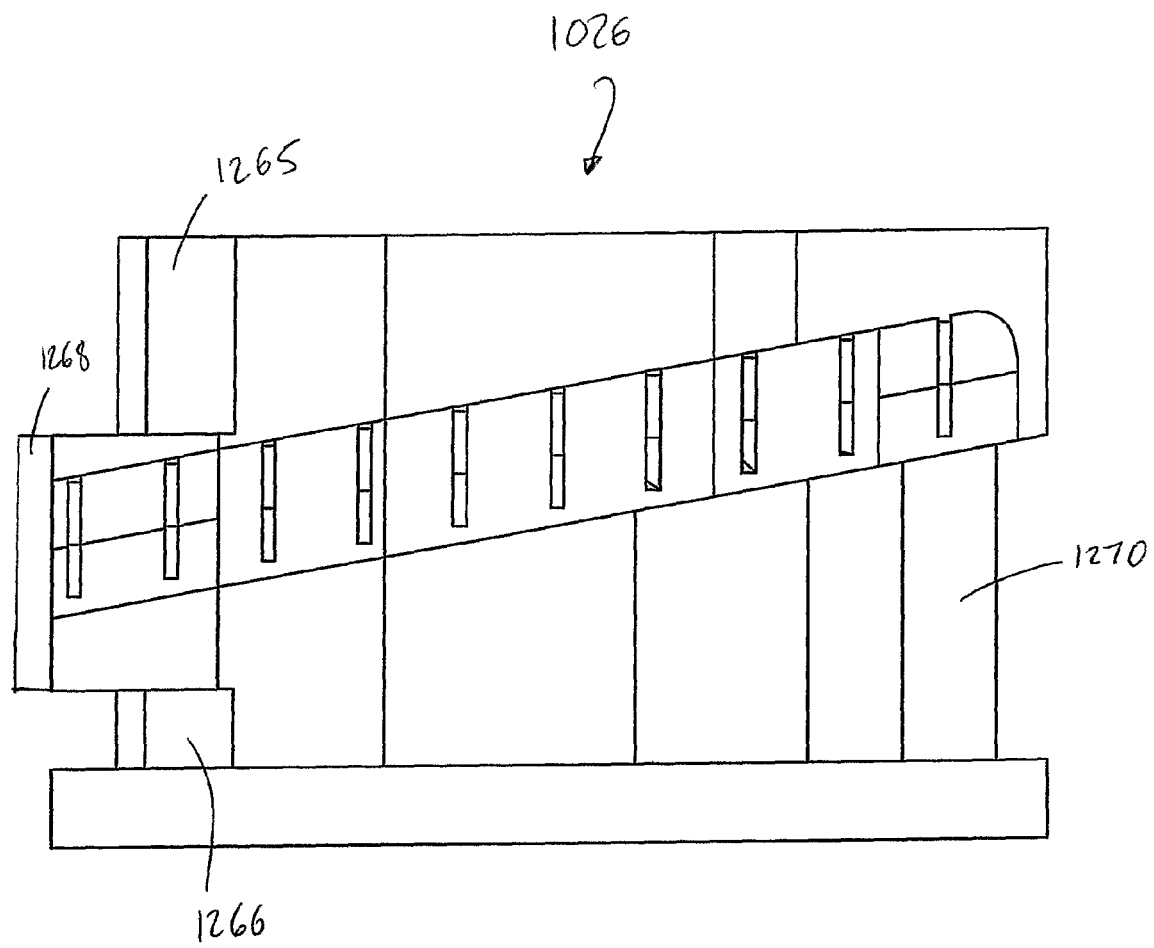
FIG. 75 is a second side view of the movable element.
Figure 76:
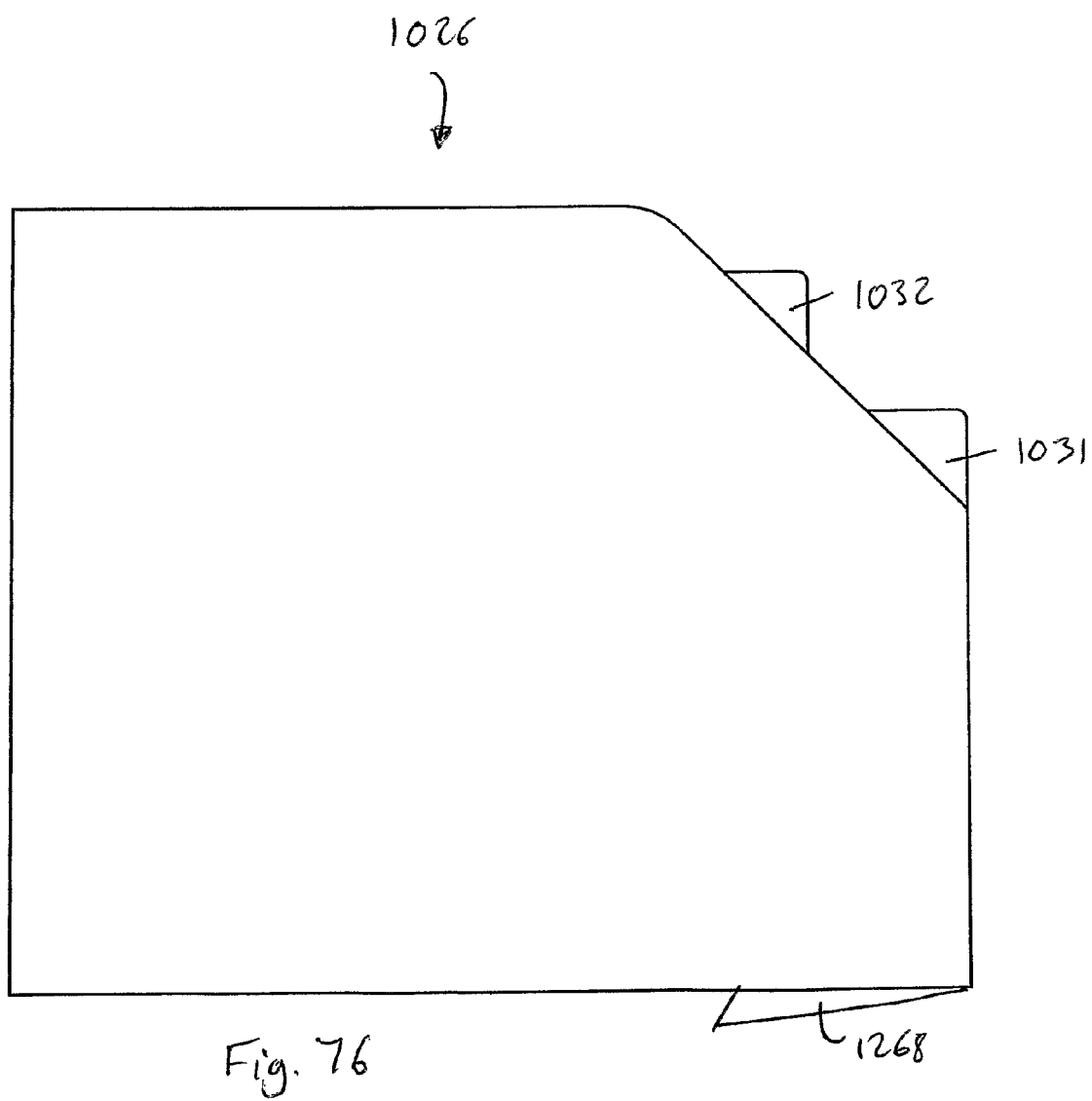
FIG. 76 is a plan view from below of the movable element of FIGS. 68 and 69.
Figure 77:
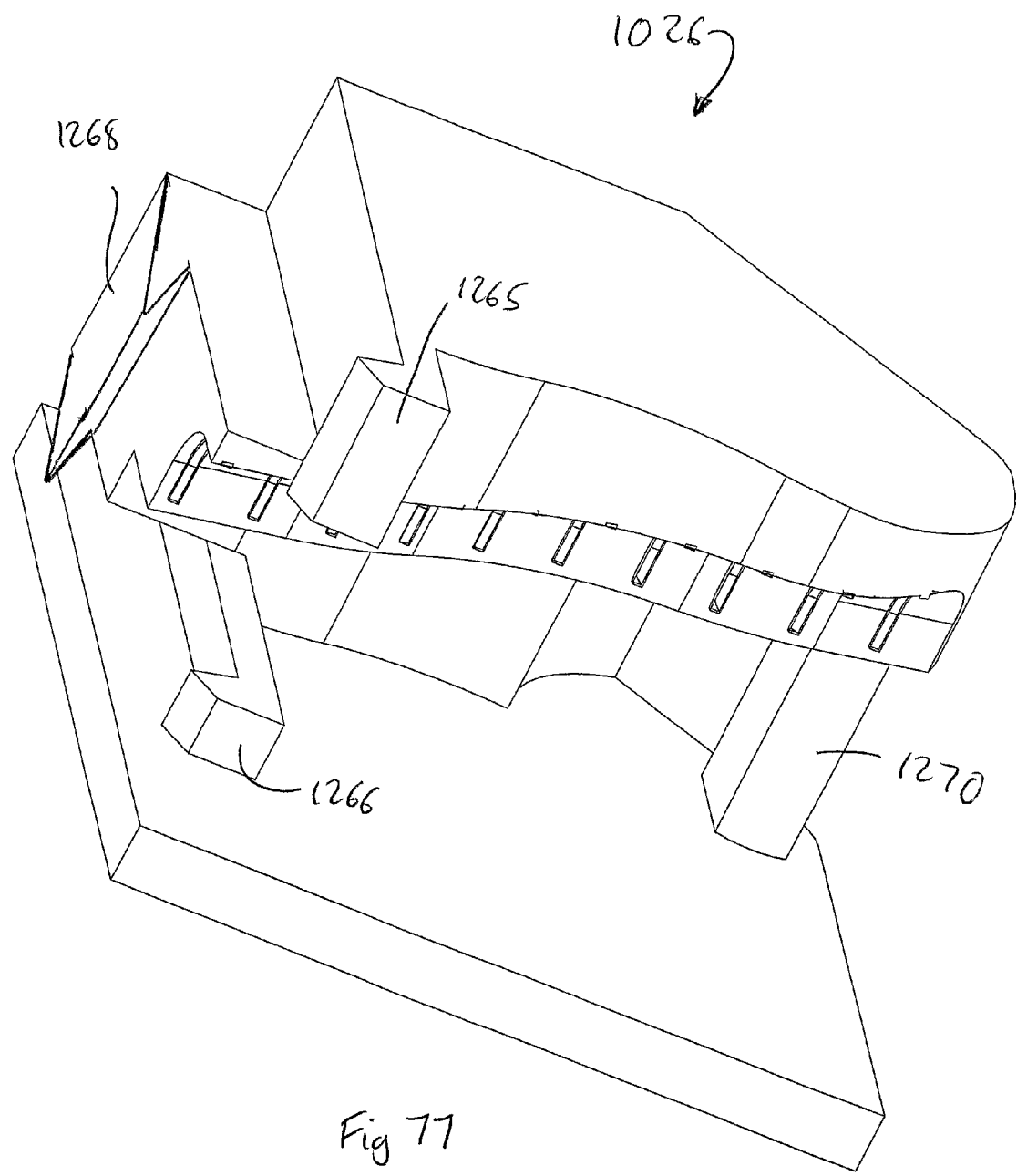
FIGS. 77 and 78 are further perspective views of the movable element of FIGS. 68 and 69.
Figure 78:
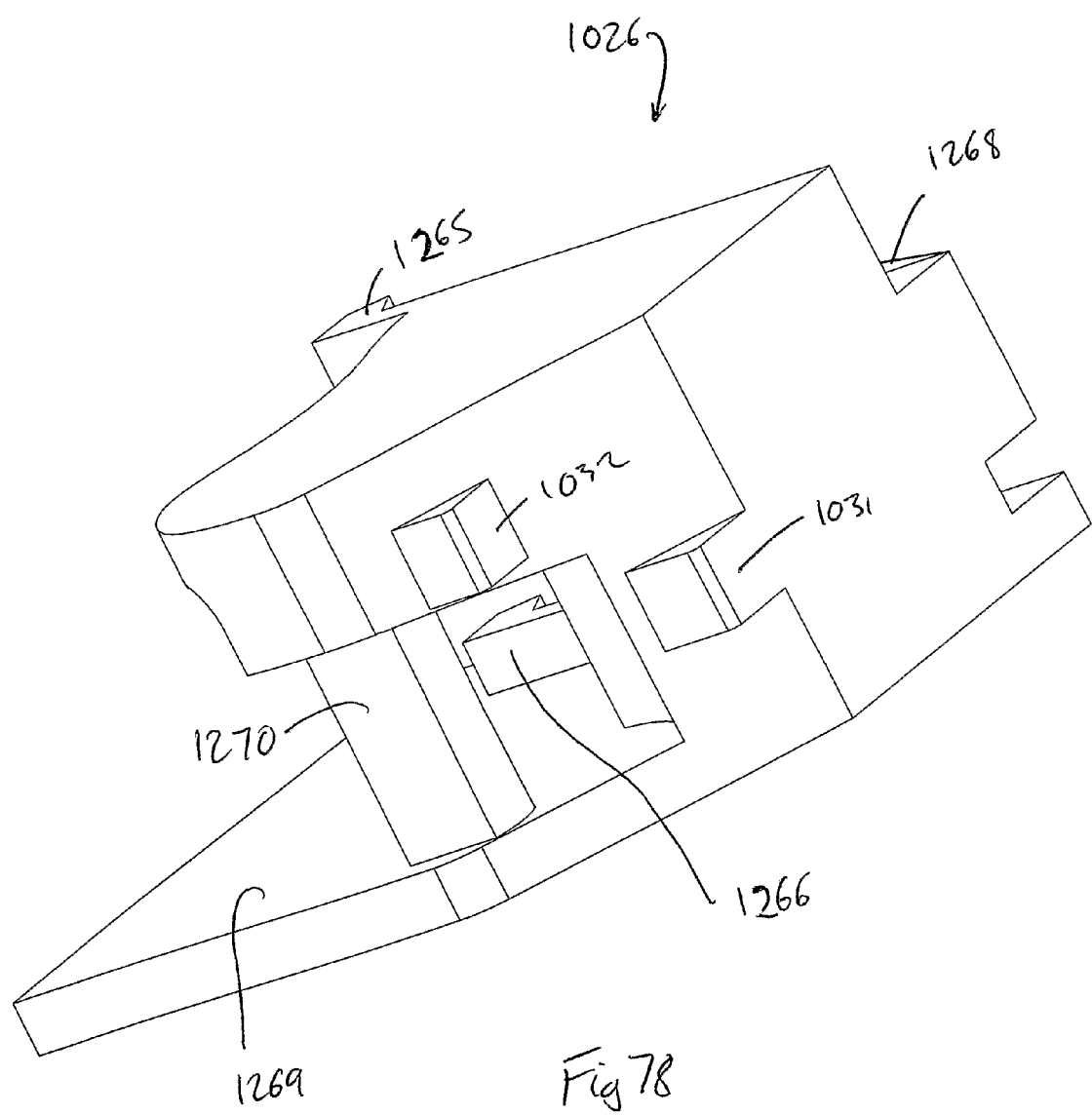
Figure 79:
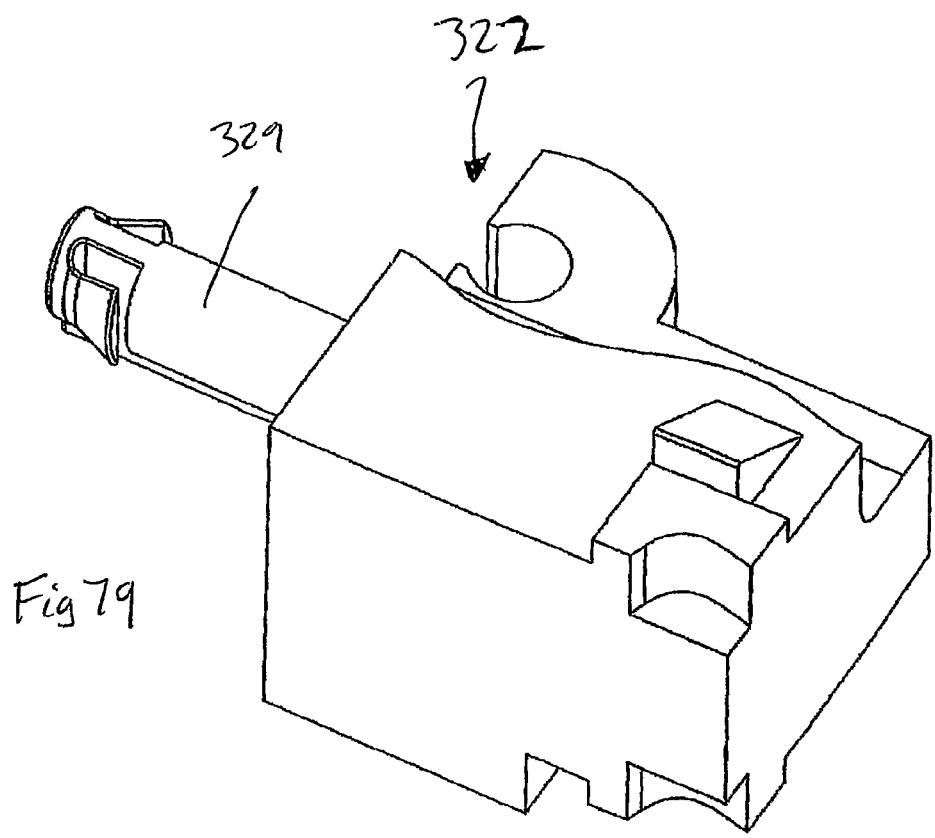
FIGS. 79 to 85 are illustrations of a variation of the main body illustrated in FIGS. 27 to 34.
Figure 80:
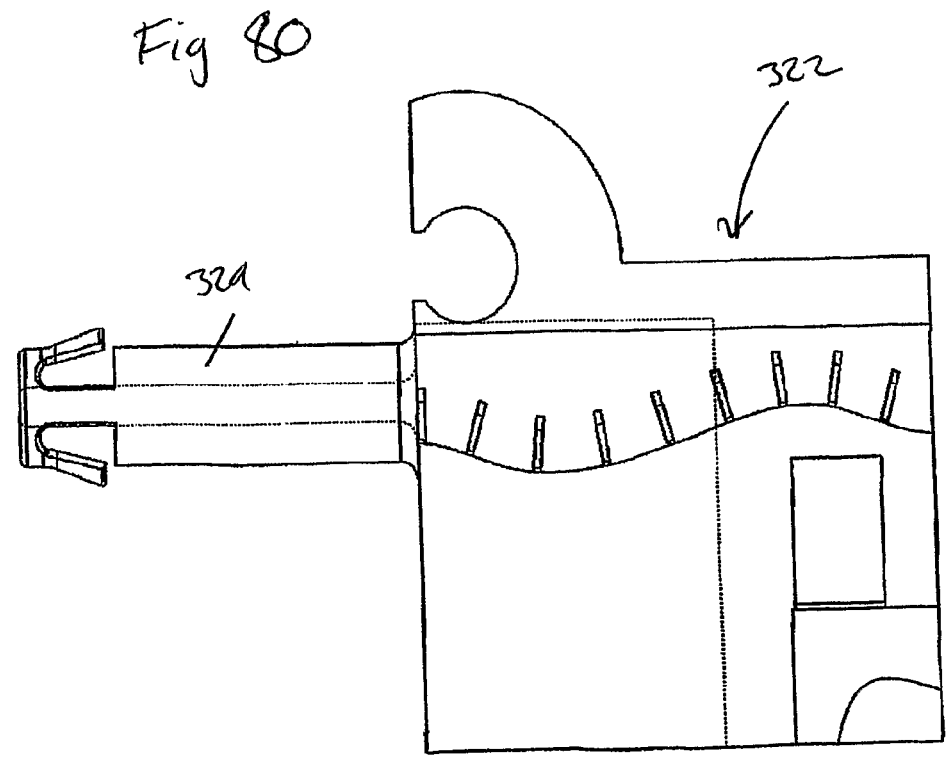
Figure 81:
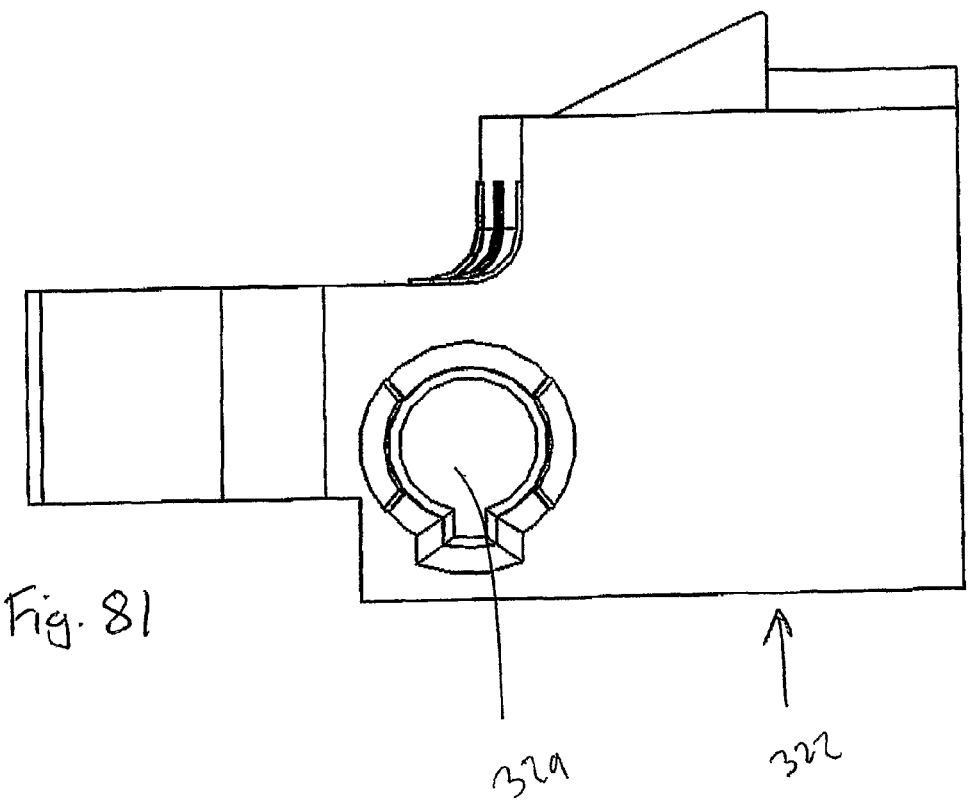
Figure 82:
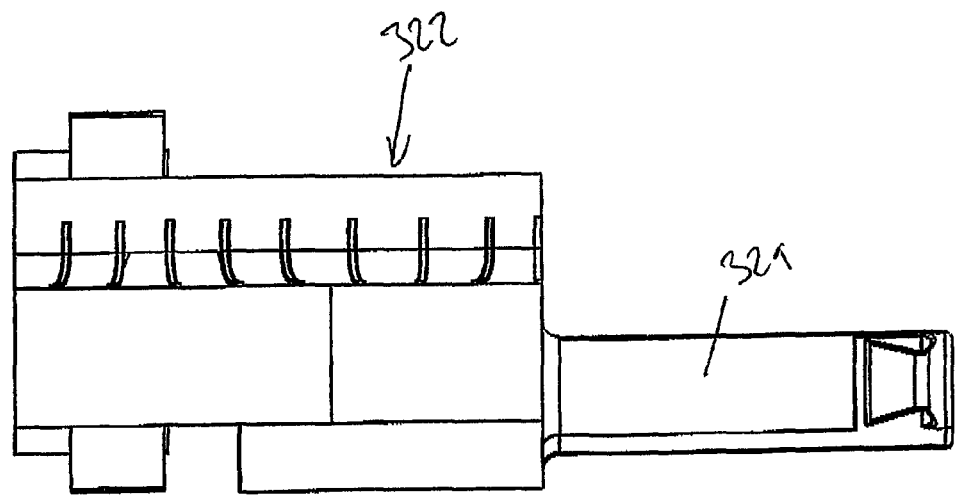
Figure 83:
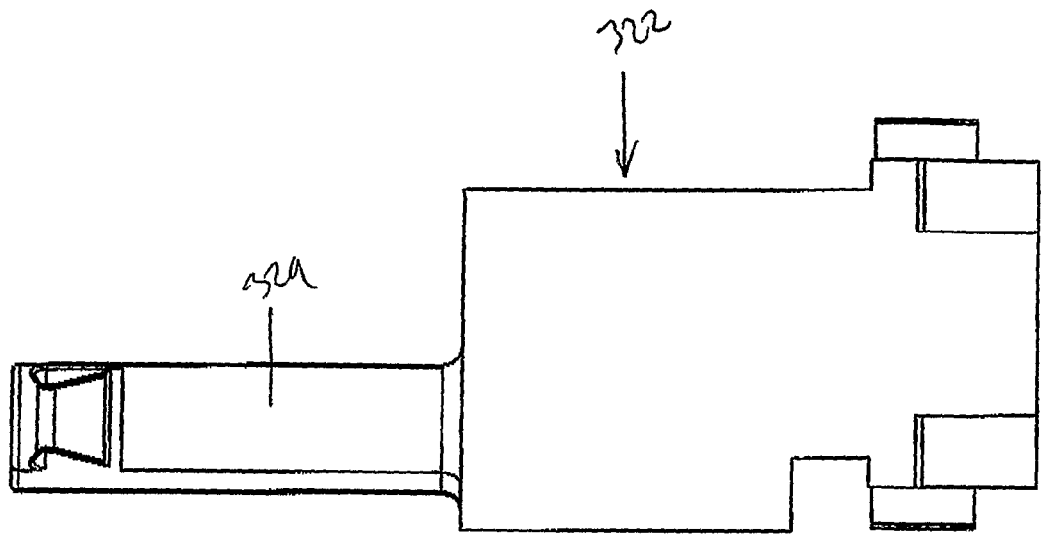
Figure 84:
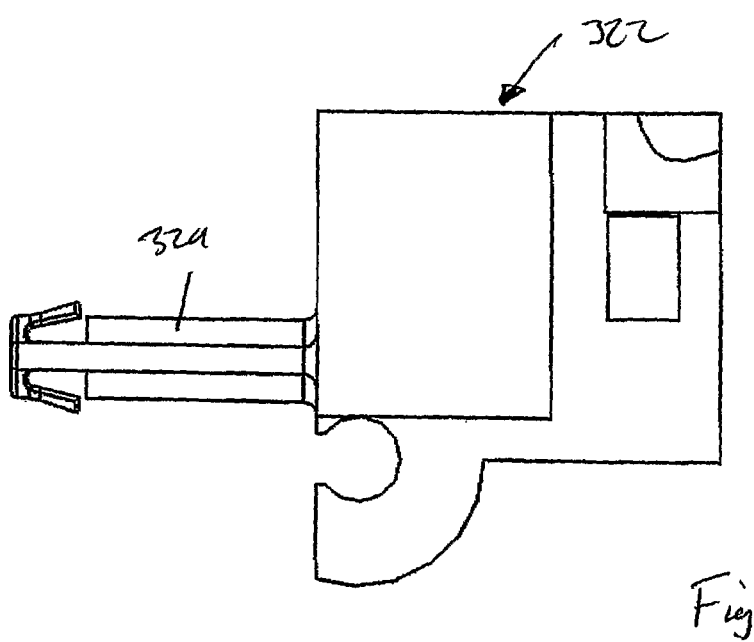
Figure 85:
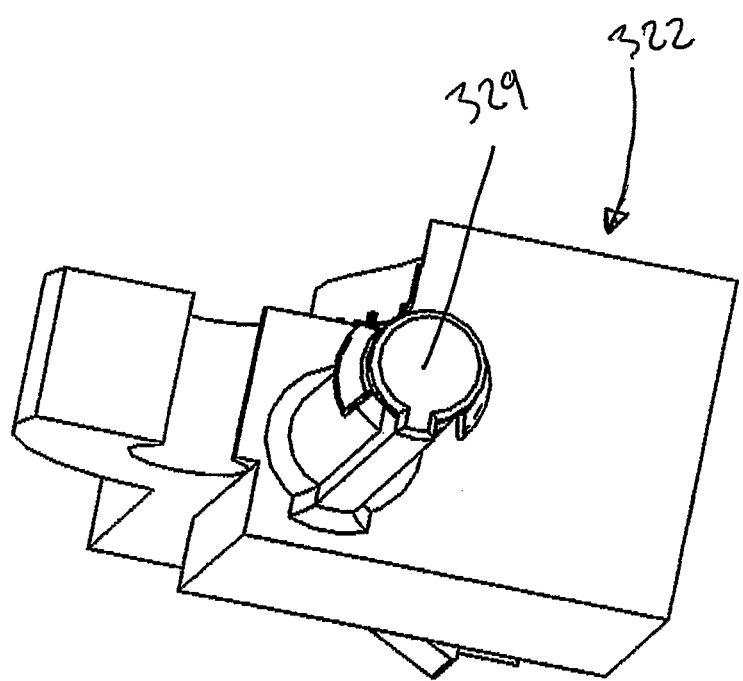

As illustrated in FIG. 56, when the clip portion 1010 is in its closed position the locking projections 1031, 1032 do not prevent operation of the gripping portion from the closed to the open position because the clip bodies 1012, 1016 are no longer positioned so that they will contact the locking projections 1031, 1032, even with the gripping portion in its open configuration.

It will be appreciated that the piercing members or prongs have been omitted from the illustrations of the attachment device 1001 for clarity, but that prongs similar or identical to those of the attachment device 1 would be used in practice.

Attachment device 1001 further differs from attachment device 1 in the structure of the clasp for locking the gripping portion 1020 in its closed position. In the attachment device 1001 the main body 1022 is provided, at a rear end thereof, with a clasp element 1225 comprising a clasp engagement portion 1226 which is attached, somewhat resiliently, to the main body 1022 by a clasp arm 1227. The movable element 1026 is provided with upper and lower clasp elements 1265, 1266 which are substantially rigidly attached thereto. The clasp element 1225 is adapted to engage and lock onto the upper and lower clasp elements 1265, 1266 when the gripping portion 1020 is moved to its closed position, in order to effectively lock the gripping portion 1020 in its closed position. However, because the clasp arm 1227 is resilient bendable, and because the angle of engagement of the engaging parts of the clasp elements 1225, 1265, 1266 is appropriate, the clasp can be unlocked by application of an appropriate force to the main body clasp element 1225. The clasp for locking the gripping portion 1020 in its closed position is preferably structured so that unlocking is extremely difficult without the use of a suitable tool. This is important since accidental unlocking can have serious consequences.

In the illustrated embodiment an unlocking projection 1228 is provided on the clasp engagement portion 1226 of the clasp element 1225. Applying an adequate force to the unlocking projection 1228 so as to force it in the direction away from the movable element 1026 causes the clasp arm 1227 to bend sufficiently to release the clasp elements 1265, 1266 of the movable element 1026 and thereby effectively unlock the gripping portion. A second unlocking projection 1268 is provided on the movable element 1026. It is intended that the unlocking operation would be performed by applying forceps (or another suitable tool) between the unlocking projection 1228 and the second unlocking projection 1268, and operating the tool (preferably opening the forceps) to force apart the unlocking projection 1228 and the second unlocking projection 1268. In the illustrated embodiment, the unlocking projection 1228 and the second unlocking projection 1268 are intended to be too small, and require too great a force, to allow adequate purchase to unlock the gripping portion 1020 without the use of tools. Of course alternative arrangements for locking the gripping portion 1020, and/or for allowing deliberate unlocking of the gripping portion 1020, while avoiding inadvertent unlocking, could be provided.

Attachment device 1001 further differs from attachment device 1 in that the moveable element is provided with a basal plate 1269 which slides under the main body 1022 when the gripping portion 1020 is closed, and which provides a basal surface for contact with the skin. The main body 1022 also has a basal surface 1230, (which does not contact the patient when the gripping portion 1020 is closed, since it is covered by the basal plate 1269) and a retaining projection 1231 is provided on the main body basal surface 1230. The retaining projection 1231 contacts the leading edge of the basal plate 1269 when the gripping portion is in its open position (as illustrated in eg FIG. 51) and prevents the basal plate 1269, and thus the movable element 1026, from moving towards the closed position unless a predetermined closing force (adequate to force the leading edge of the basal plate 1269 past the retaining projection 1231) is applied. Thus the gripping portion is effectively maintained in its open position until deliberately closed. This means of retaining the gripping portion in its open position may replace, or be in addition to, the mechanism described in relation to the attachment device 1 for retaining the gripping portion 20 in its open configuration.

Attachment device 1001 further differs from attachment device 1 in that the passage way in which the tube is to be held is not parallel to the basal surface. That is, the passage is not intended to be parallel to the skin, in use. Instead the passage is inclined somewhat so as to direct the tube slightly towards the skin at the rear of the attachment device 1001. This provides a lower profile for the tube and reduces the chance of inadvertent snagging or catching of the secured tube.

Operation of the attachment device 1001 is essentially the same as operation of the attachment device 1, except that the clip portion 1010 cannot be operated before the gripping portion 1020. However, if necessary the gripping portion 1020 could be re-opened after operation of the clip portion 1010 to allow further adjustment of the position of the tube. The gripping portion 1020 may be configured so that a tube may be gently gripped between upper parts of the main body 1022 and moveable element 1026 when the gripping portion is open.

FIGS. 79 to 85 show perspective views of a variation of the main body 22. The main body 322 of FIGS. 79 to 85 is similar to the main body 22 and includes a very similar attachment element 329. However, the main body 322 is squarer in overall shape and therefore has a slightly greater base area for contact with the skin of a patient.

Figure 86:
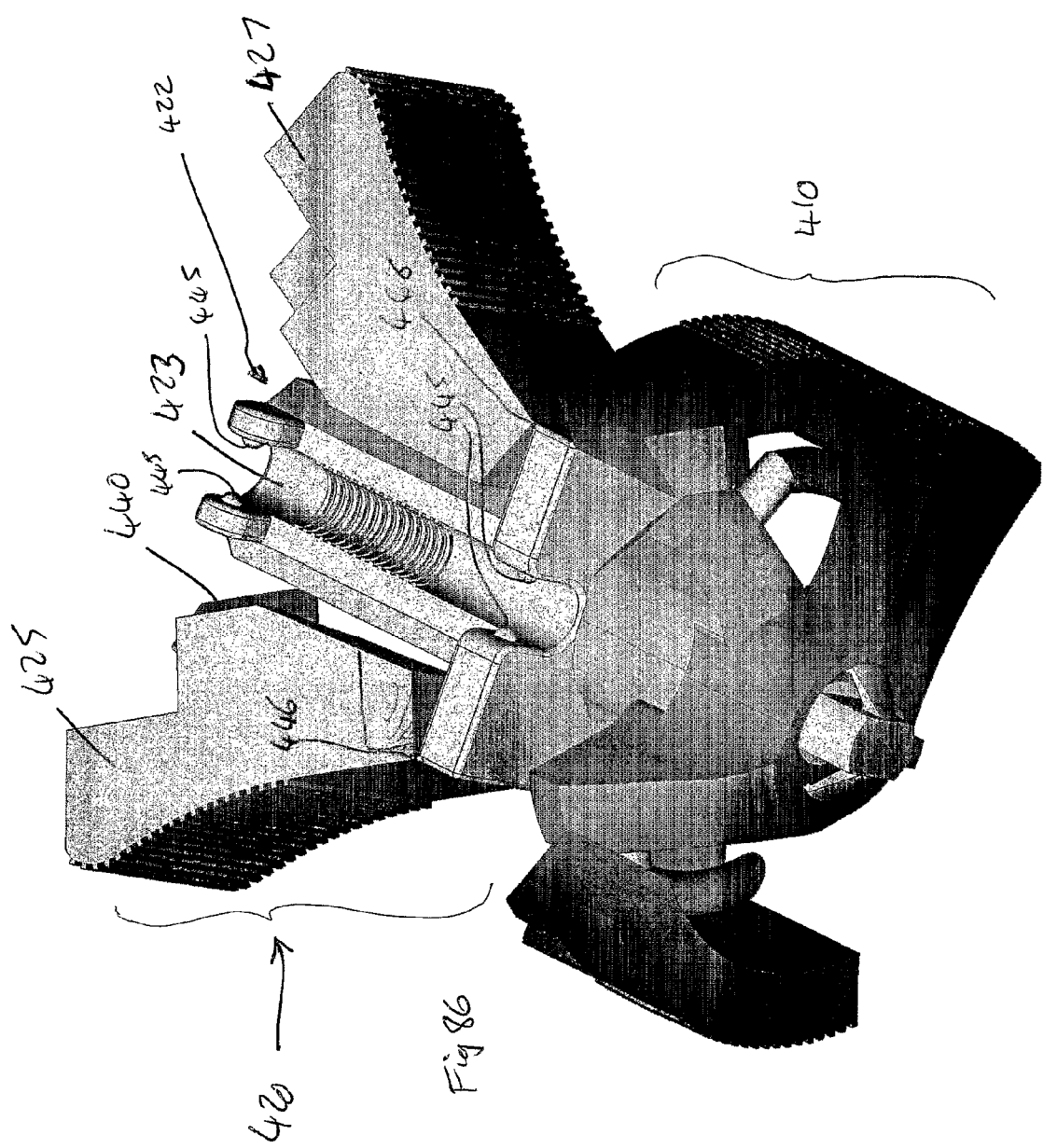
FIGS. 86 to 88 are perspective views of an alternative embodiment of an attachment device in which, in particular, the gripping portion is different to that of the previously illustrated embodiments.
Figure 87:
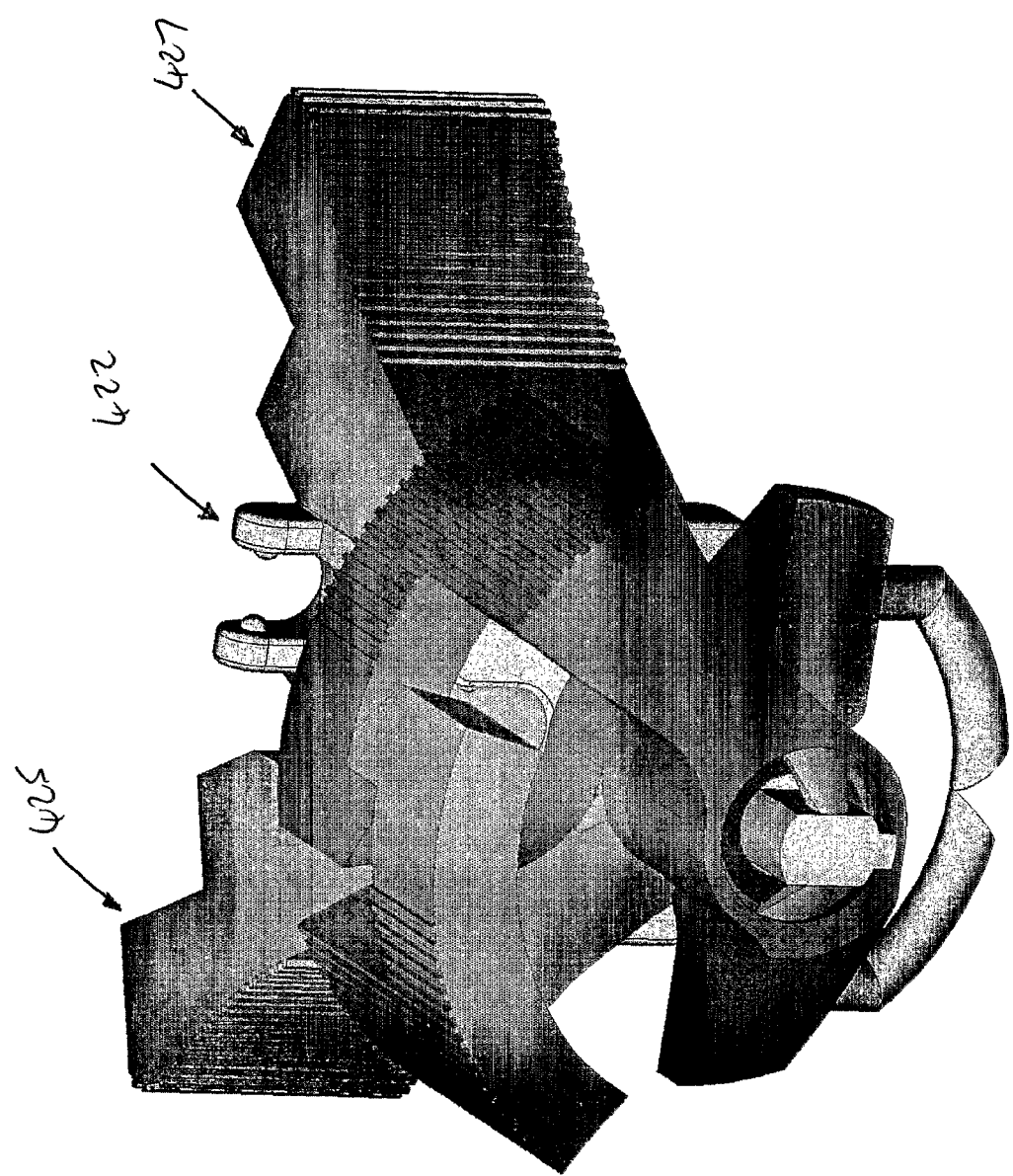
Figure 88:
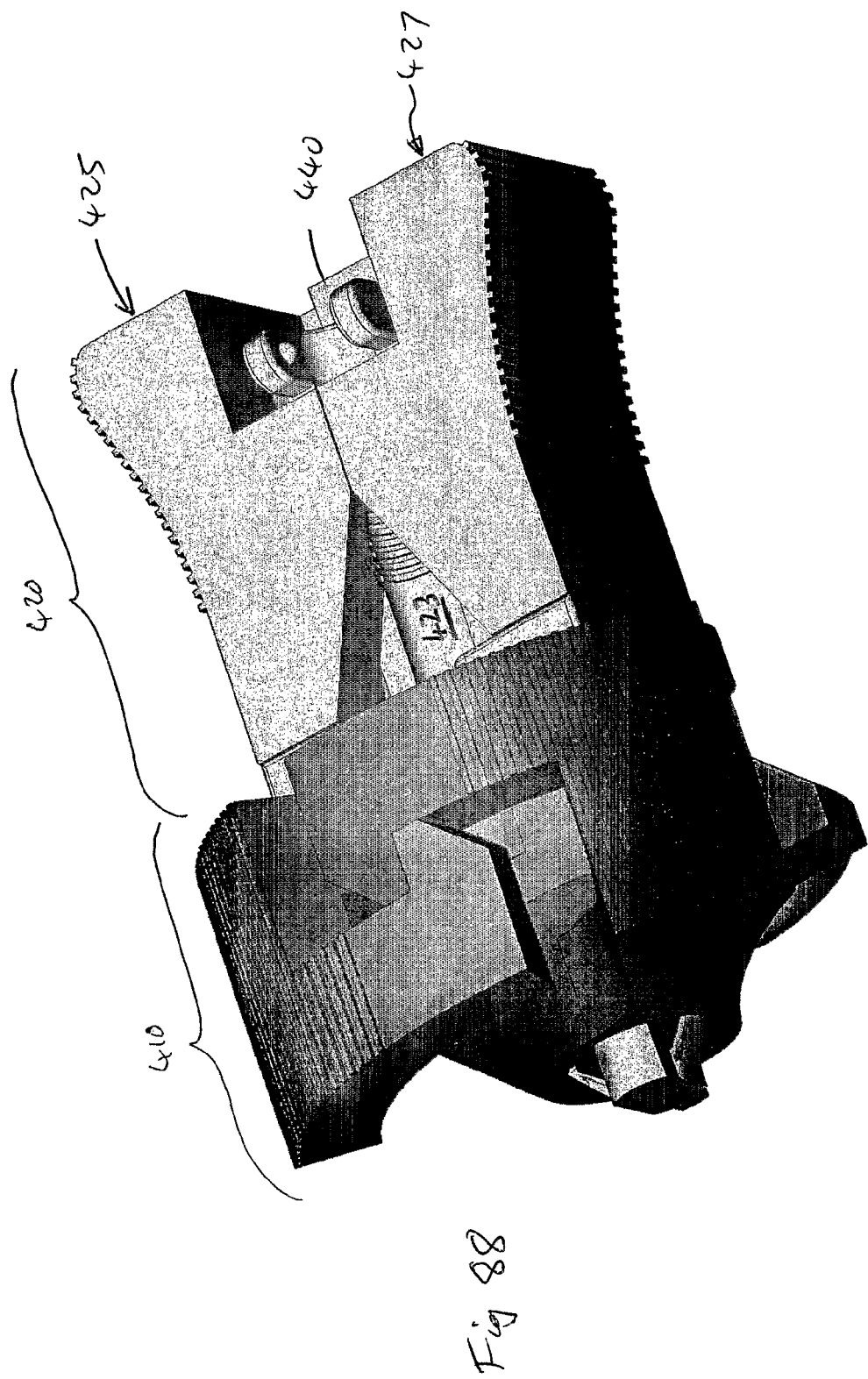
Figure 95:
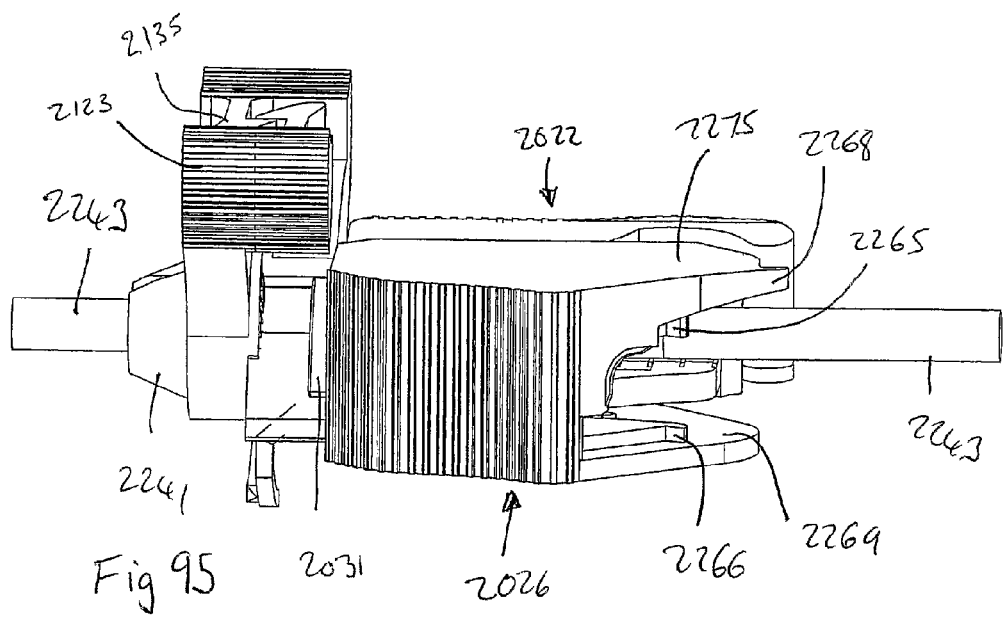
FIG. 95 is a perspective view from slightly above the point of view of FIG. 94.
Figure 96:
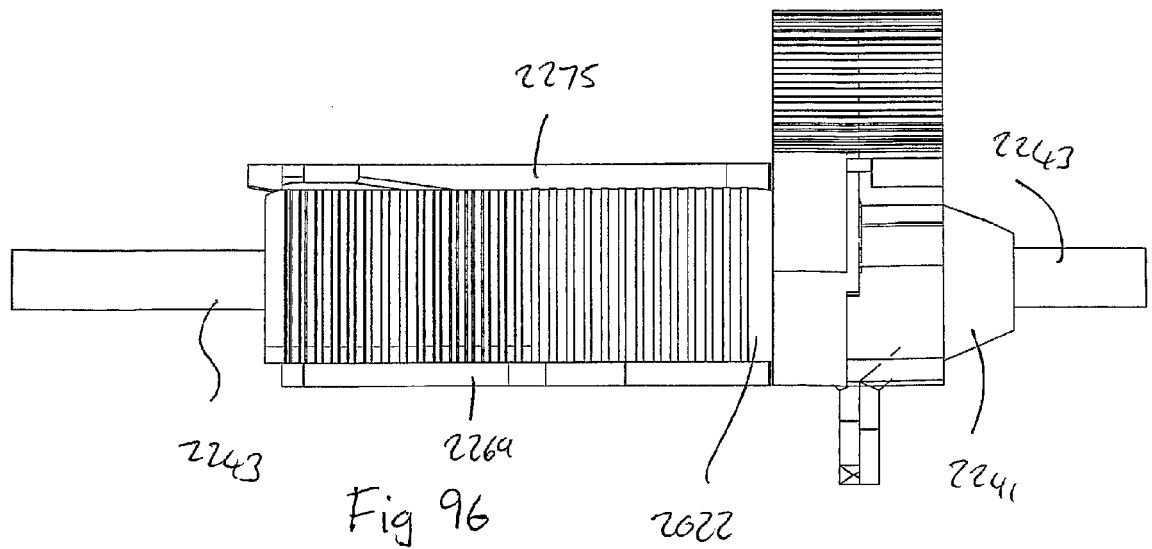
FIG. 96 is a second side view corresponding to FIG. 90.
Figure 97:
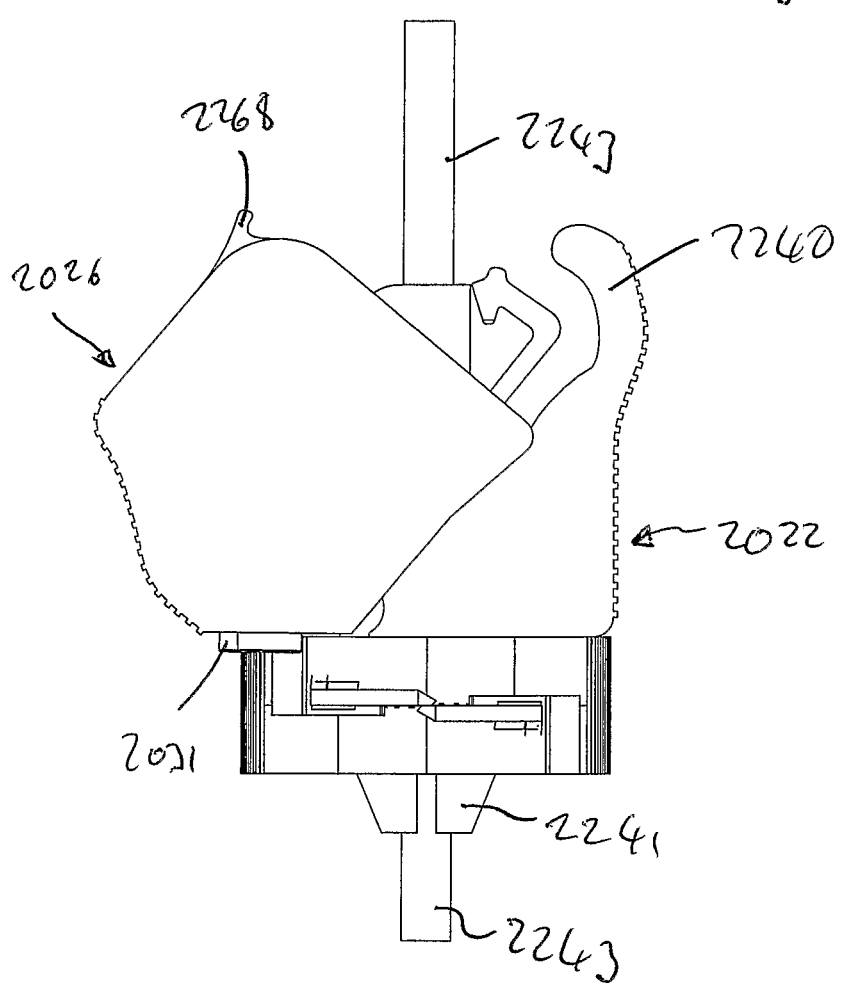
FIG. 97 is a bottom plan view corresponding to FIG. 90.
Figure 98:
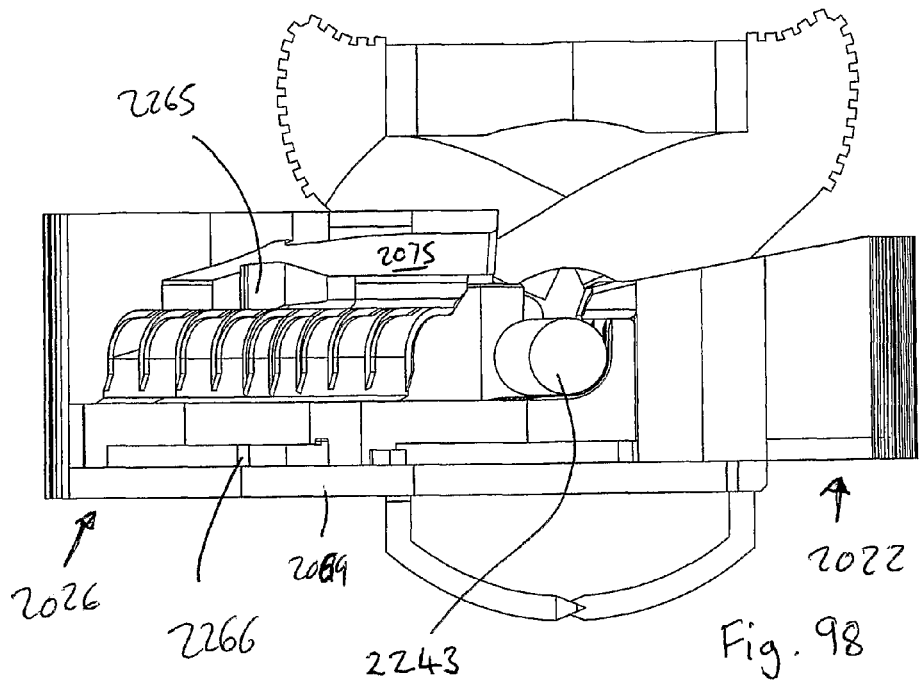
FIG. 98 is a second end view corresponding to FIG. 90.
Figure 99:
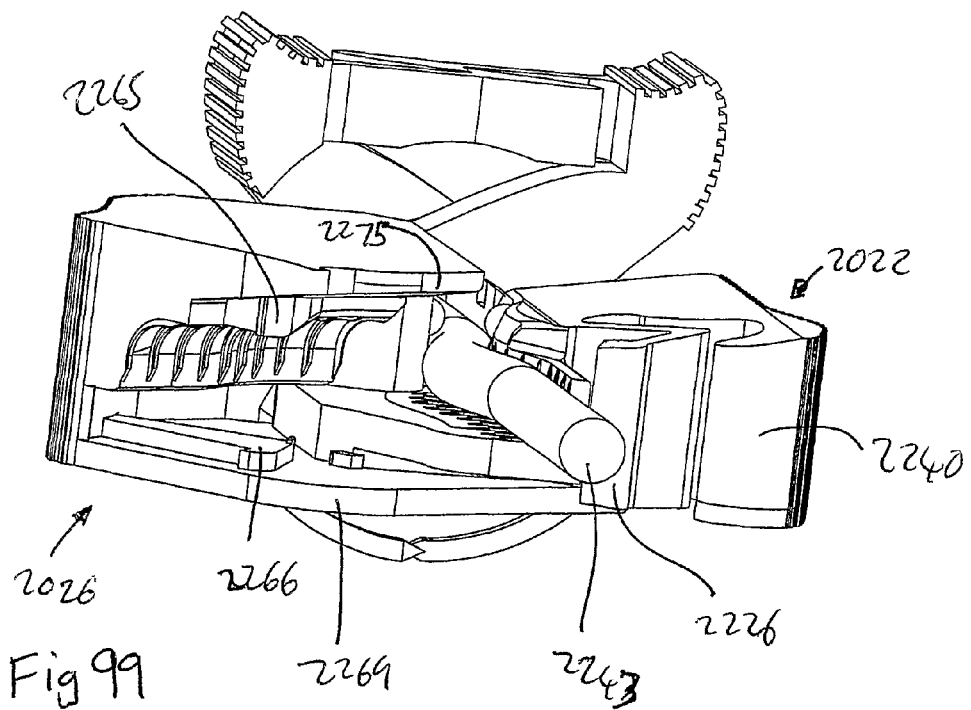
FIGS. 99 and 100 are further perspective views, generally from the second end, corresponding to FIG. 90.
Figure 100:
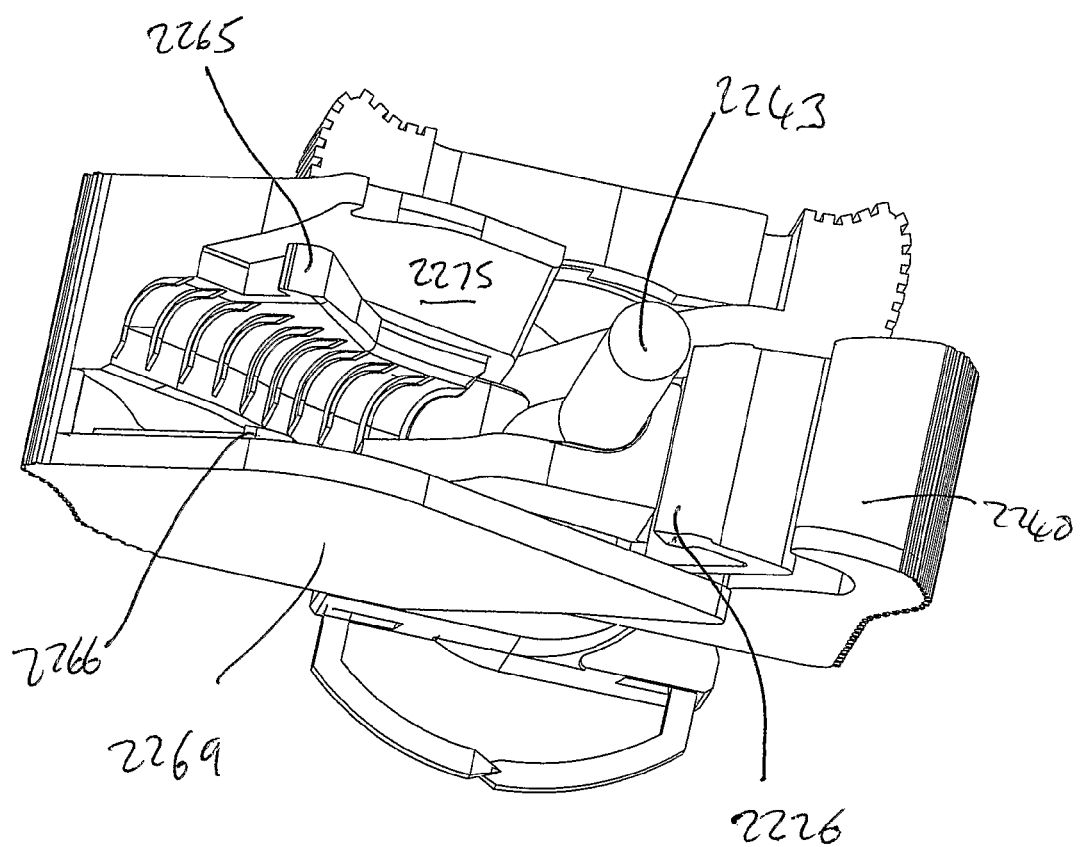
Figure 101:
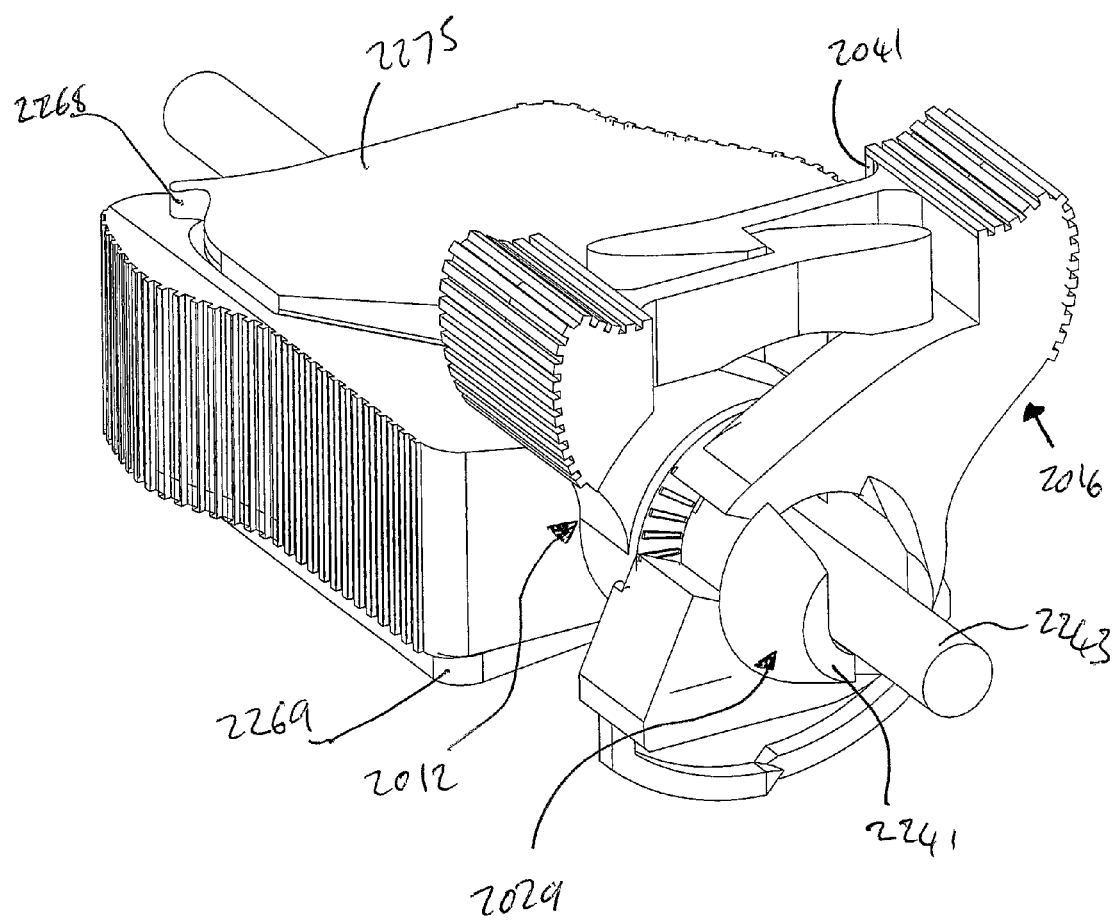
FIG. 101 is a perspective view of the embodiment of FIG. 90, with the clip portion and gripping portion both shown in their closed positions.

FIGS. 86 to 88 show an attachment device in which a gripping portion 420 comprises a main body 422 comprising a substantially half-cylindrical channel portion 423 and first and second movable elements 425, 427 each including a substantially quarter-cylindrical channel portion (not shown), and a clasp portion 440 for locking the gripping portion 420 in its closed position. Preliminary gripping projections 445 on the main body 422 allow gentle gripping of, for example, a catheter tube, prior to the secure gripping provided by closing the gripping portion 420.

In this embodiment the gripping portion 420 may be injection moulded from a suitable plastic as a single unit with one-piece hinges 446 formed from parts of the plastic material with reduced thickness. FIG. 89 shows a horizontal cross-sectional view of the device of FIGS. 86 to 88 in a configuration with both the gripping portion 420 and clip portion 410 in their closed positions. The clip portion 410 is very similar to the clip portion 10 of the earlier described embodiment and FIG. 89 may give some additional insight into the structure of the clip portions 10, 1010.

With reference to FIGS. 90 to 119 a further alternative embodiment, attachment device 2001, will be described. It will be appreciated that this alternative embodiment has many similarities to the embodiment of FIGS. 1 to 46, and still more to the embodiment of FIGS. 47 to 78. Consequently, in the following description many of the similarities will be assumed and the emphasis will be on the differences between the embodiments (although similarities will be mentioned to enhance clarity).

Similarly to the embodiments described above, attachment device 2001 comprises a clip portion 2010 for attaching the device to the tissue of a user, and a gripping portion 2020 for gripping a tube. The clip portion 2010 comprises first and second clip bodies 2012, 2016. The gripping portion 2020 comprises a main body 2022 and a moveable element 2026.

The gripping portion 2020 provides an attachment element 2029 which extends forwardly from the main body 2022 of a gripping portion 2020 and on which first and second clip bodies 2012, 2016 are mounted in use. The attachment element 2029 may be regarded as being generally in the form of a rod, and has a deformably widened end portion 2241, distal to the main body 2022, which facilitates mounting of the first and second clip bodies 2012, 2016, but avoids inadvertent demounting thereof. Unlike the attachment elements of the above described embodiments, the attachment element 2029 defines a channel 2242 therein, which is adapted to accommodate a tube 2243 of a medical device, therein, in use.

As can be seen in, for example, FIGS. 90, 92, 94, 95, 96, 97, 101 and 102, in use the tube 2243 effectively passes through the attachment device and extends axially out of the end portion 2241 of the attachment element 2029. FIGS. 107, 108, 109, 111 and 112 show the main body 2022 in isolation, and show the attachment element 2029 with the channel 2242 extending generally axially therethrough. The channel 2242 may be regarded as generally U-shaped, the attachment element 2029 having an elongate opening (continuous with the channel) which extends along its length to facilitate non-axial insertion of a tube. That is, a tube can be inserted into the channel, via the elongate opening, by moving the tube in a generally radial direction (in this case, by moving a generally horizontal tube downwardly). In this embodiment the elongate opening is on an upper side of the attachment element 2029 (that is, a side which is adapted, in use, to be further from the adjacent tissue of a patient).

It will be noted that the attachment element 2029 has an axial slot 2244 provided therein, which (together with the elongate opening of the channel) effectively separates the attachment element 2029 into two spaced apart lateral portions (and which, in this embodiment runs substantially the entire length of the attachment element). The two spaced apart lateral portions can resiliently be forced together, providing a degree of deformability for the widened end portion 2241 which will be discussed in more detail in due course. (Of course, in other embodiments the deformability of the end portion 2241 could be provided in alternative ways.)

FIGS. 104 to 106(b) illustrate the form and use of the clip bodies 2012, 2016 of this embodiment of attachment device 2001. The clip bodies 2012, 2016 differ, in a number of ways, from those of attachment devices 1 and 1001. The two clip bodies 2012, 2016, are identical (but oriented differently in the assembled attachment device 2001) so although some of the designations provided on FIGS. 104 and 105 relate to the first clip body 2012, it will be appreciated that the second clip body 2016 corresponds, and that reference numerals used in the written description that relates to FIGS. 104 and 105 may reflect this. (Of course, although it is preferred that clip bodies 2012, 2016, are identical, since this is considered to facilitate manufacture and assembly, it will be appreciated that the first and second clip bodies are not required to be identical.)

Figure 104:
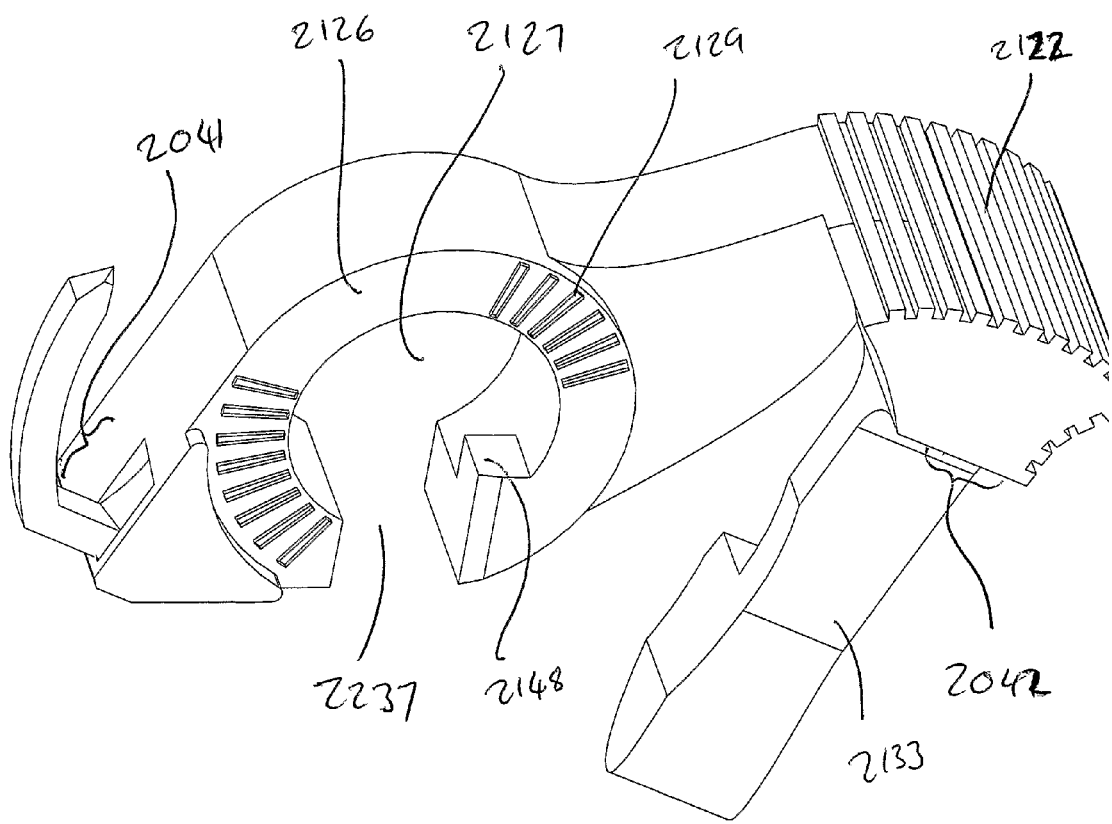
FIGS. 104 and 105 are perspective views of a clip body, which forms part of the clip portion of the embodiment of FIGS. 90 to 103, from respective first and second ends.
Figure 105:
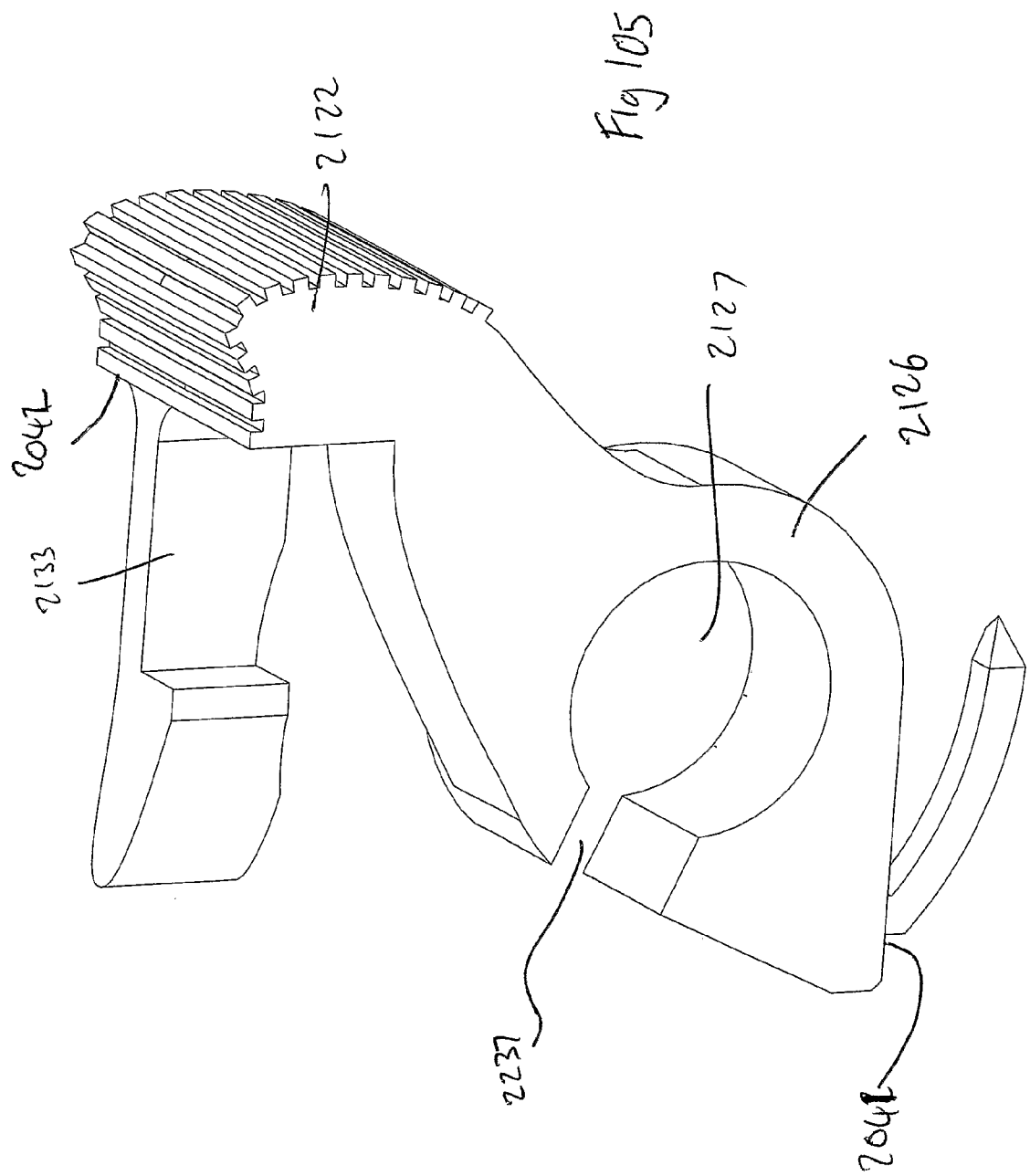

With reference to, in particular, FIGS. 104 and 105, each clip body 2012, 2016 is provided with a middle portion 2126 which defines a through aperture 2127, for mounting the clip body on the attachment member 2029. However, the middle portion 2126 does not entirely circumferentially surround the through aperture 2127, but leaves a circumferentially extending gap 2237 extending approximately one sixth of the circumference of the middle portion 2126.

It will be appreciated that in use, one side of the middle portion 2126 of each clip body slidingly engages the middle portion 2126 of the other clip body. These slidingly engaging parts are, in this embodiment, provided with a plurality of small projections 2129, so that the sliding engagement provides a positive action, and so that a definite force must be applied to rotate the clip bodies 2012, 2016 relative to each other.

Each clip body 2012, 2016 is provided with a first abutment surface 2041 close to the point where the prong projects from the clip body, and a second abutment surface 2042 close to where a clasp portion 2133 projects from an operating portion 2122 of the clip body.

Each clip body 2012, 2016 is also provided with a projection 2148 which extends from the middle portion 2126 a small distance into the otherwise generally cylindrical through aperture 2127. In use, the projections 2148 on the respective clip bodies 2012, 2016 interact with restriction parts 2149 (see FIG. 107) of the attachment member to limit the extent of available rotation of the clip bodies relative to the attachment member 2029.

It will be appreciated that in order to assemble the device the clip bodies 2012, 2016 are pushed axially onto the attachment member 2029. This is possible because the widened end portion 2241 is deformable so that it can be passed through the apertures 2127 in the clip bodies 2012, 2016. In this embodiment the widened end portion 2241 is provided by separate parts which are, in equilibrium, spaced apart, and which may be forced towards each other in order to reduce the effective size of the end portion 2241. As illustrated (although variations are possible) the widened end portion 2241 is provided by two laterally separate parts which are, in equilibrium, laterally spaced apart, and which may be forced towards each other in order to reduce the effective lateral width of the end portion 2241. It will be appreciated that in the illustrated embodiment the effective size of the end portion 2241 in the direction which is, in use, perpendicular to the skin of a patient (referred to, for convenience as the "height" direction) cannot vary to the same extent as the lateral size. This determines the orientation of the clip bodies 2012, 2016 as they are mounted onto the attachment member 2029, since the gap 2237 must be aligned above the remainder of the through aperture 2127 in order for the portion 2241 to pass though the aperture 2127. This orientation corresponds to the open, sharps safe, position of the clip portion, as will be appreciated from the following description.

Figure 106A:
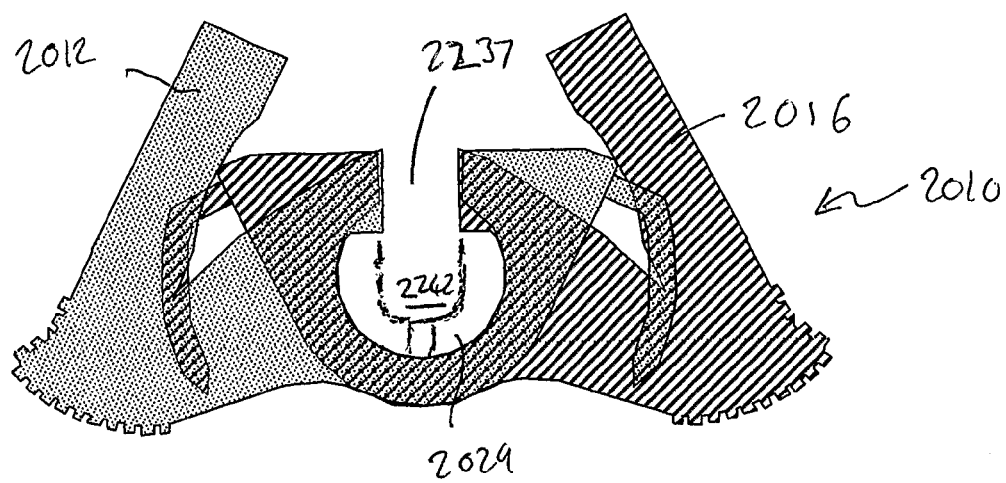
FIGS. 106(a) and 106(b) show schematically the relative positions of two clip bodies when the clip portion is in respectively, open and closed positions.

With reference to FIG. 106(a), which should be regarded as schematic only, it will be appreciated that the gaps 2237 are positioned and aligned on the clip bodies 2012, 2016 such that when the clip bodies 2012, 2016 are mounted on the attachment member 2029 oriented such that the clip portion 2010 is in its open position, the gaps 2237 align with the open top of the channel 2242.

Figure 106B:
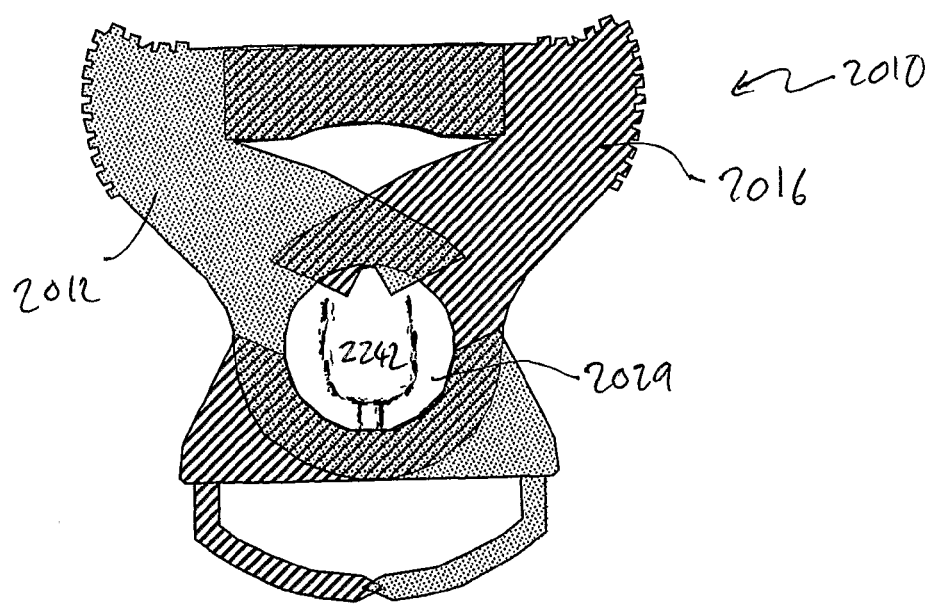

When the clip bodies 2012, 2016 are mounted on the attachment member 2029 oriented such that the clip portion 2010 is in its closed position, the gaps 2237 are not aligned with the open top of the channel 2242, as illustrated schematically in FIG. 106(b).

The openings in the middle portions 2126 of the clip bodies thus allow the tube 2243 to be placed into the channel 2242 of an assembled attachment device 2001 when the clip portion 2010 is in its open position. However, when the clip bodies 2012, 2016 are mounted on the attachment member 2029 oriented such that the clip portion 2010 is in its closed position, the middle portions 2126 extend across, and close off, the opening of the channel 2242.

The attachment device 2001 provides a projecting element 2031 on a wall of the moveable element 2026 which is similar in function to the first and second locking projections 1031, 1032 of the attachment device 1001, and is provided so that when both the gripping portion 2020 and clip portion 2010 are in their open positions the clip portion 2010 cannot be closed.

Figure 106C:
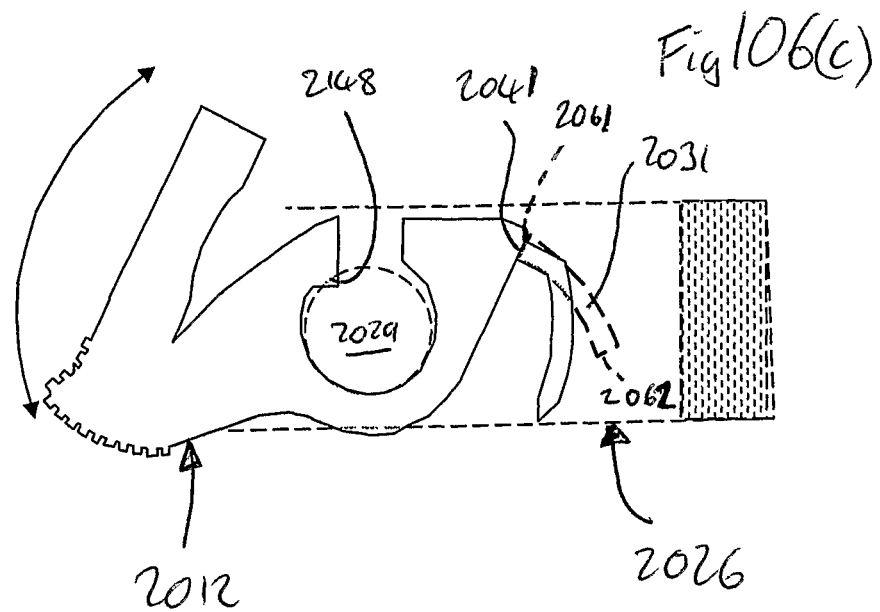
FIGS. 106(c) and 106(d) show schematically a mechanism for retaining a clip portion of the device in an open position when a gripping portion of the device is in an open position.
Figure 106D:
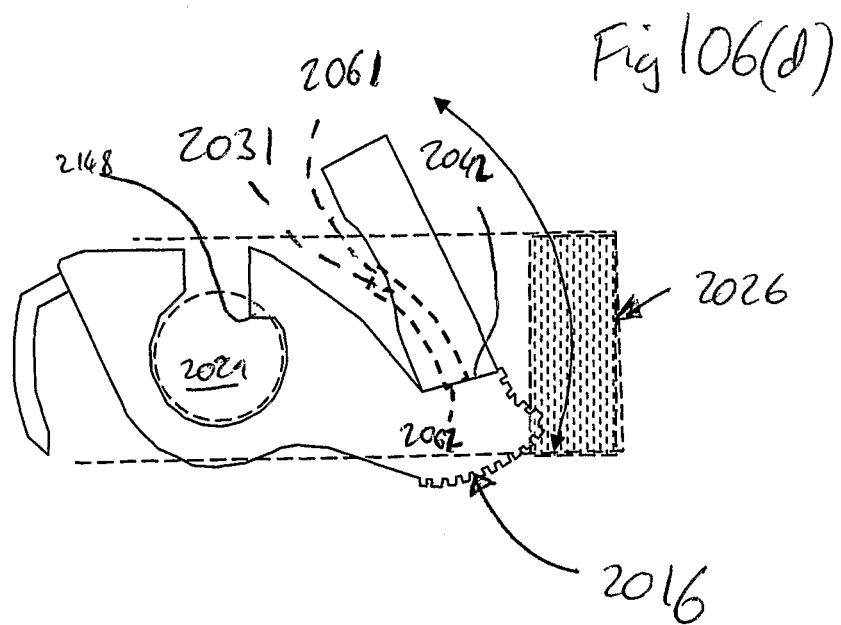
Figure 108:
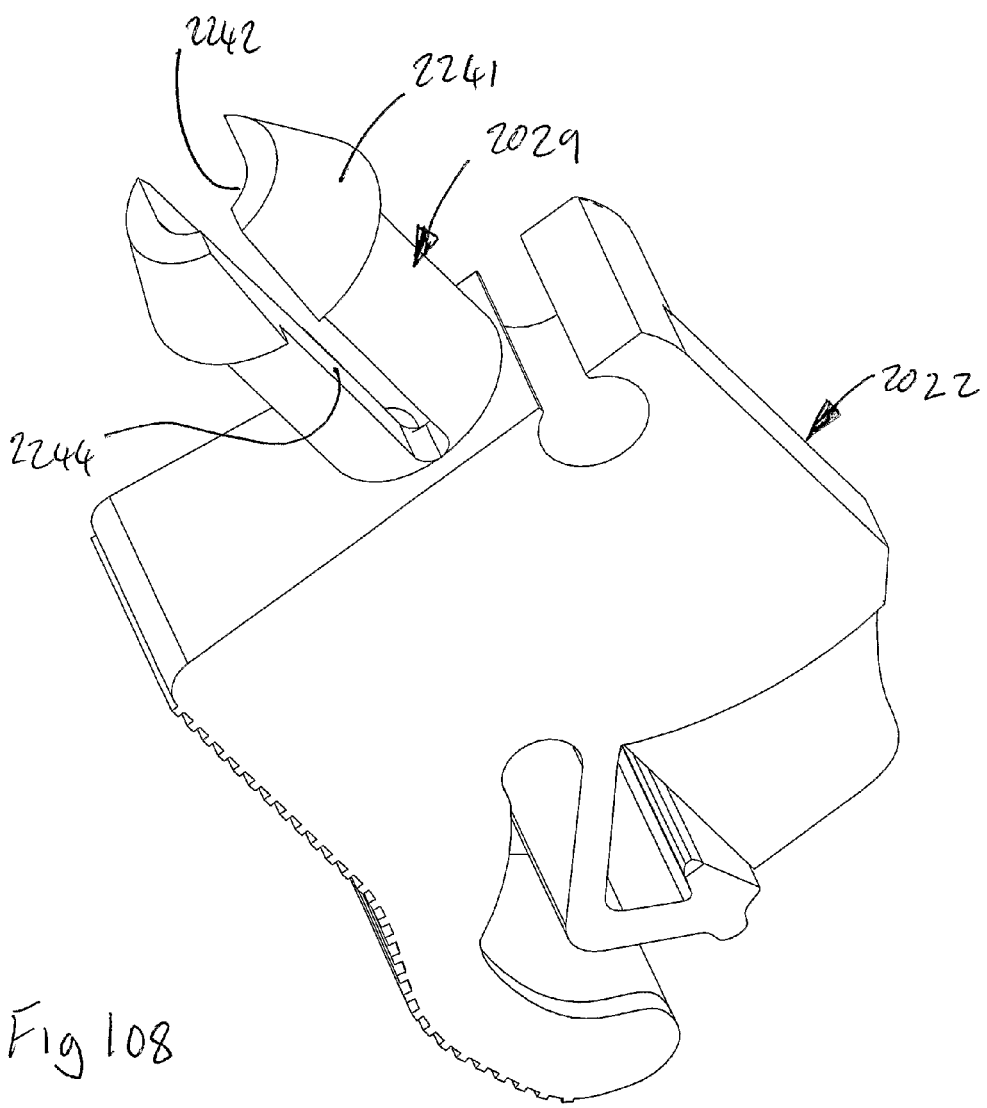
Figure 109:
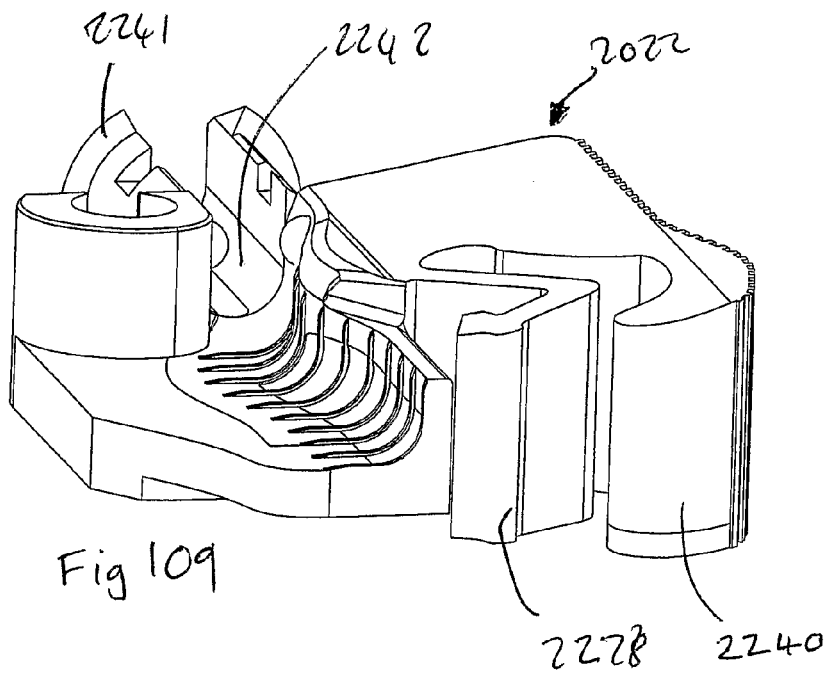
Figure 110:
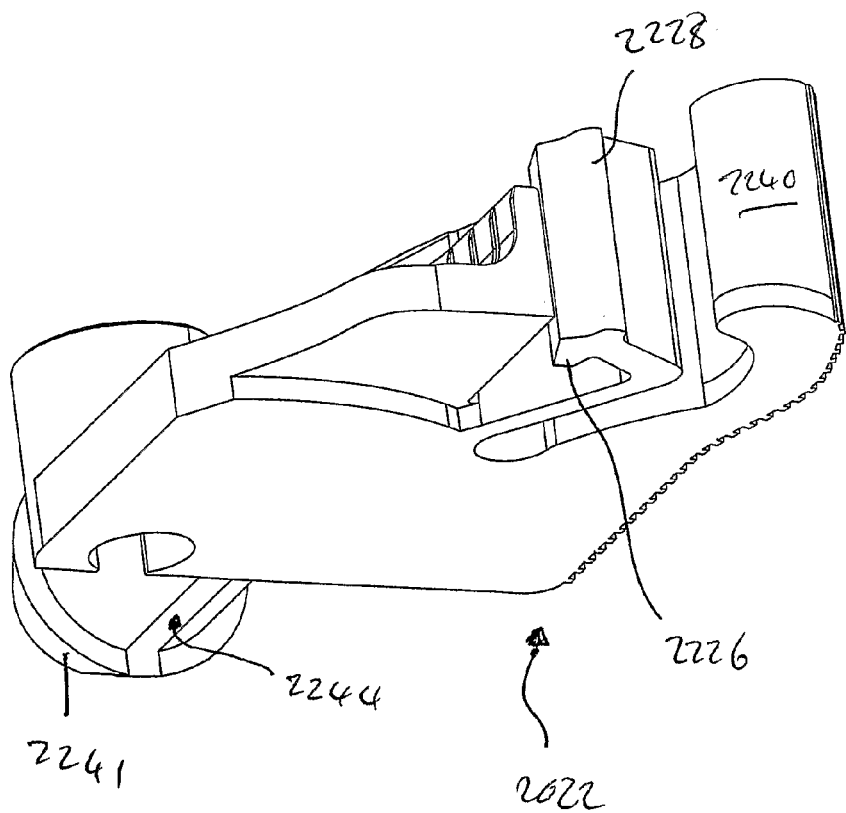
Figure 111:
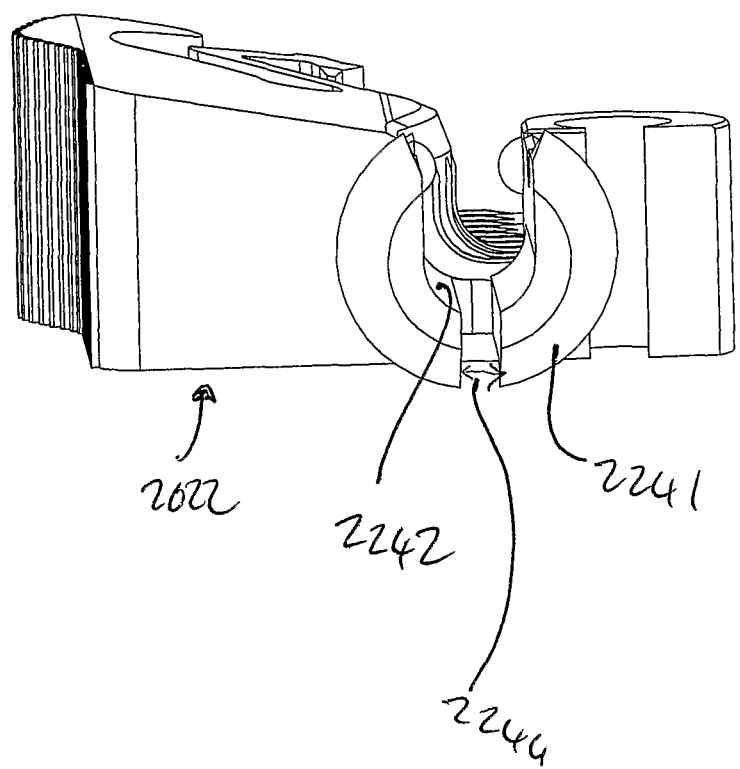

FIGS. 106(c) and 106(d) illustrate the position of the clip bodies 2012, 2016 when the clip portion 2010 is in its open position, and show schematically the mechanism for retaining the clip portion 2010 of the device in its open position when the gripping portion 2020 is in its open position.

As can be seen in FIG. 106(c) the projecting element 2031 has a first abutment end 2061 which abuts the first abutment surface 2041 of the first clip body 2012, and thus prevents the first clip body 2012 from rotating about the attachment element 2029 from the open position of the clip portion to the closed position of the clip portion.

As can be seen in FIG. 106(d) the projecting element 2031 has a second abutment end 2062 which abuts the second abutment surface 2042 of the second clip body 2016, and thus prevents the second clip body 2016 from rotating about the attachment element 2029 from the open position of the clip portion to the closed position of the clip portion.

Although only one clip body is shown in each of FIGS. 106(c) and 106(d), this is for clarity only, and it will be appreciated that in use, both of the clip bodies 2012, 2016 will be mounted on the attachment element 2029 and the projecting element 2031 will interact with both, providing of course that the moveable element 2026 is positioned appropriately, ie providing the gripping portion is in its open position.

Similarities between the projecting element 2031 and the locking projections 1031, 1032 of the attachment device 1001, will be evident and will not be described explicitly herein. Similarly, similarities in the arrangement of the clip bodies on the attachment elements of the embodiments 1001 and 2001 will be evident and will not be described explicitly herein.

From consideration of similarities between the attachment device 2001 and the attachment device 1001 described above, it will be appreciated that when the gripping portion 2020 is closed, upper and lower clasp elements 2265, 2266 on the moveable element 2026 engage with a clasp engagement portion 2226 on the main body 2022 in order to lock the gripping portion 2020 in its closed configuration, allowing a tube, such as tube 2243, of a medical device to be securely held. In use, the clip portion 2010 would then be operated by rotating the body portions 2012, 2016 about the attachment member 2029, in order to secure the attachment device 2001, and consequently the gripped tube, to the patient. Unlike the attachment device 1001, the attachment device 2001 provides a top plate 2275 on the moveable element 2026, as well as a basal plate 2269. The top plate 2275 covers a substantial part of the main body 2022 when the gripping portion 2020 is in its closed configuration. Provision of the top plate 2275 on the moveable element 2026 allows the top of the main body 2022 to be shaped in order to allow easier positioning of the tube (prior to closing the gripping portion) because the top of the main body 2022 is relieved of the task of protecting the tube when the gripping portion 2020 is closed.

In the attachment device 2001 a first unlocking projection 2228 is provided on the clasp engagement portion 2226. A second unlocking projection 2268 is provided on the top plate 2275 of the moveable element 2026, such that as the gripping portion 2020 is closed the second unlocking projection 2268 moves past the first unlocking projection 2228. See for example the relative positions of the first and second unlocking projections 2228, 2268 in FIG. 92 (gripping portion 2020 open) and FIG. 102 (gripping portion 2020 closed). In the attachment device 2001, applying an adequate force to the unlocking projections 2228, 2268 (when the gripping portion 2020 is closed) so as to force them towards each other causes the clasp engagement portion 2226 to release the clasp elements 2265, 2266 of the movable element 2026 and thereby effectively unlock the gripping portion. In the circumstances that it is not desired that a tool should be required to unlock the gripping portion, this is a more convenient unlocking action than that provided by the attachment device 1001, since the fingertips can be used to perform this action so that a simple pinching action both unlocks and at least partially opens the gripping portion 2020.

Figure 112:
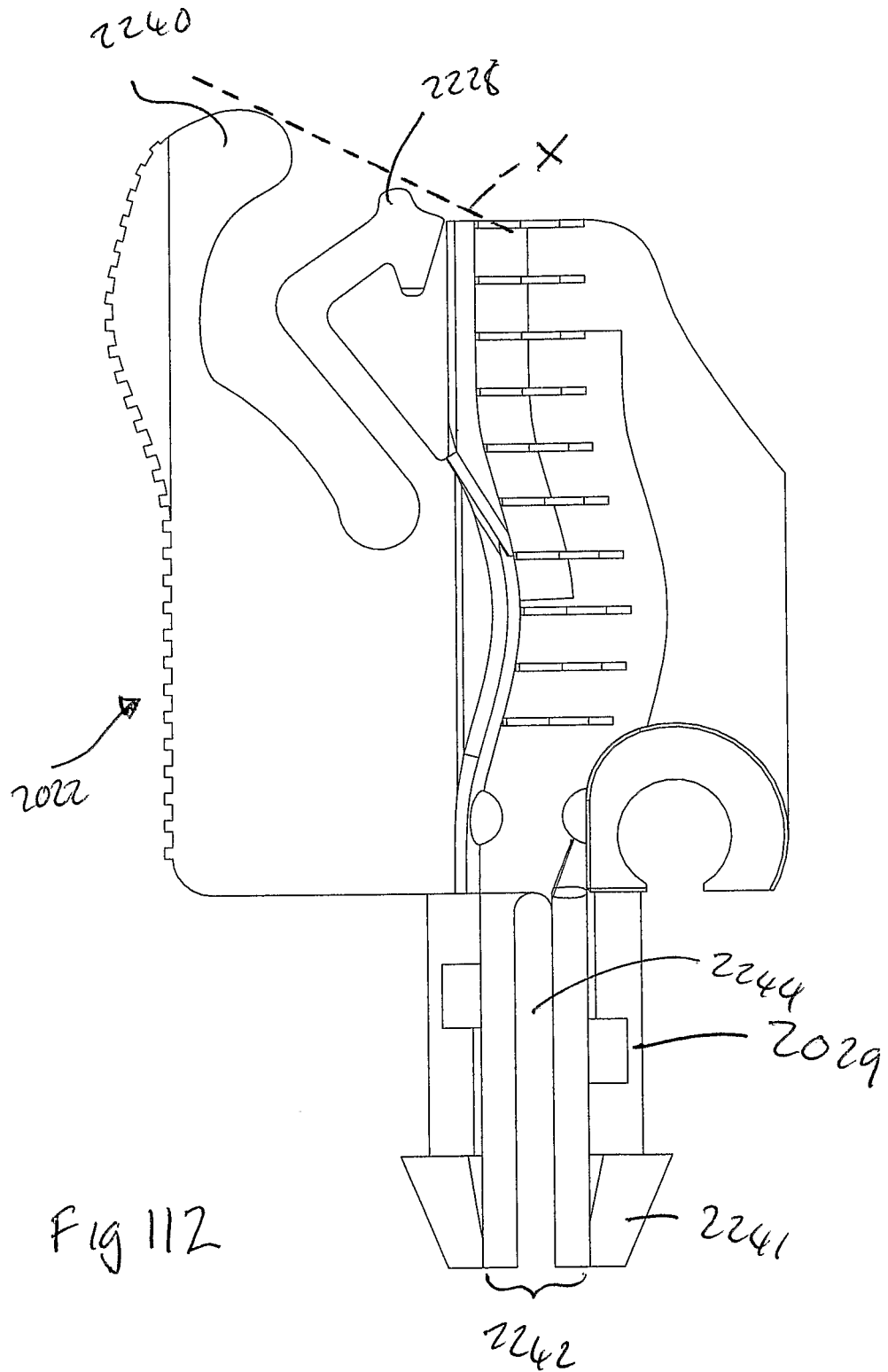
FIG. 112 is a plan view from above of the main body of FIGS. 107 to 111.
Figure 113:
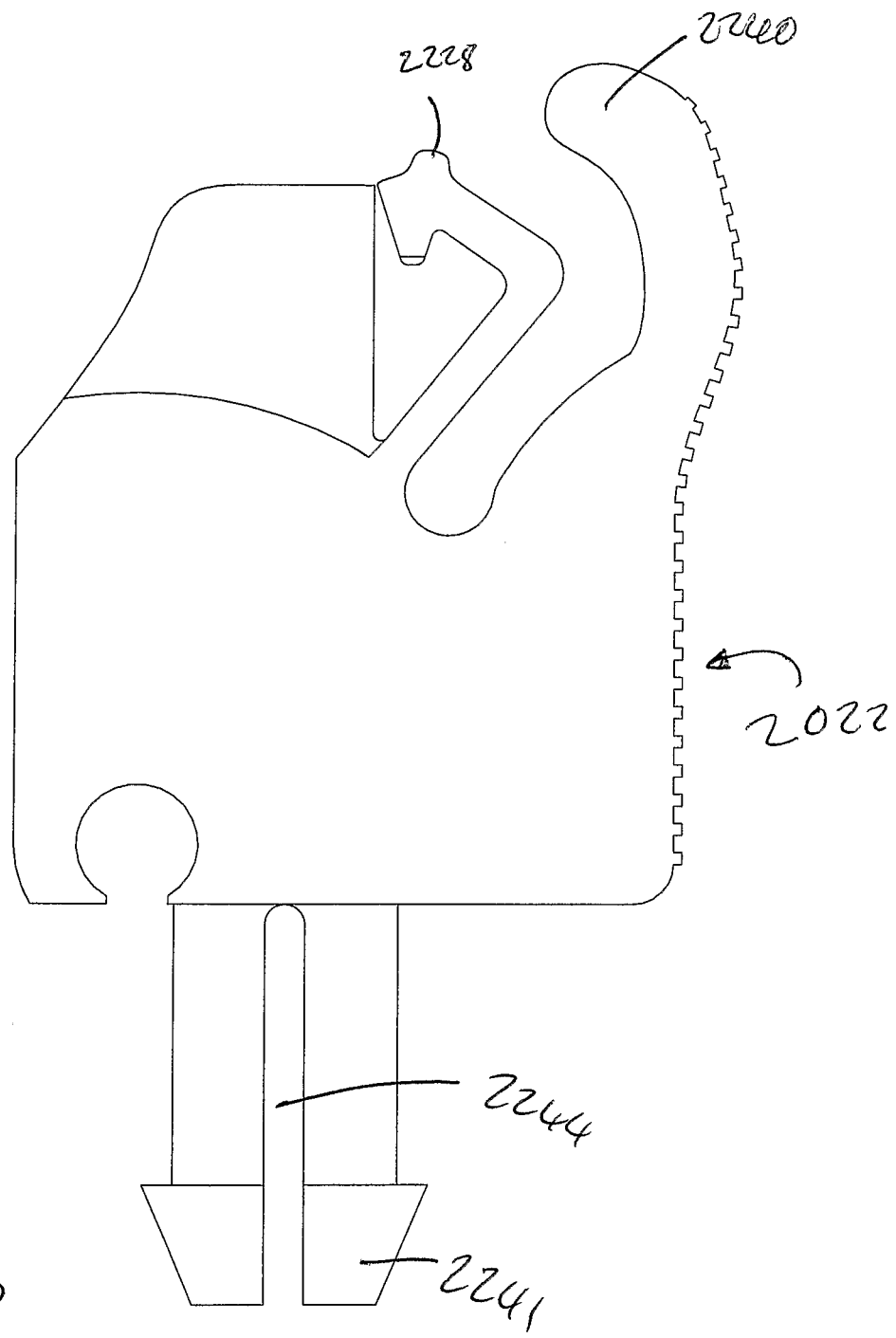
FIG. 113 is a plan view from below of the main body of FIGS. 107 to 111.
Figure 114:
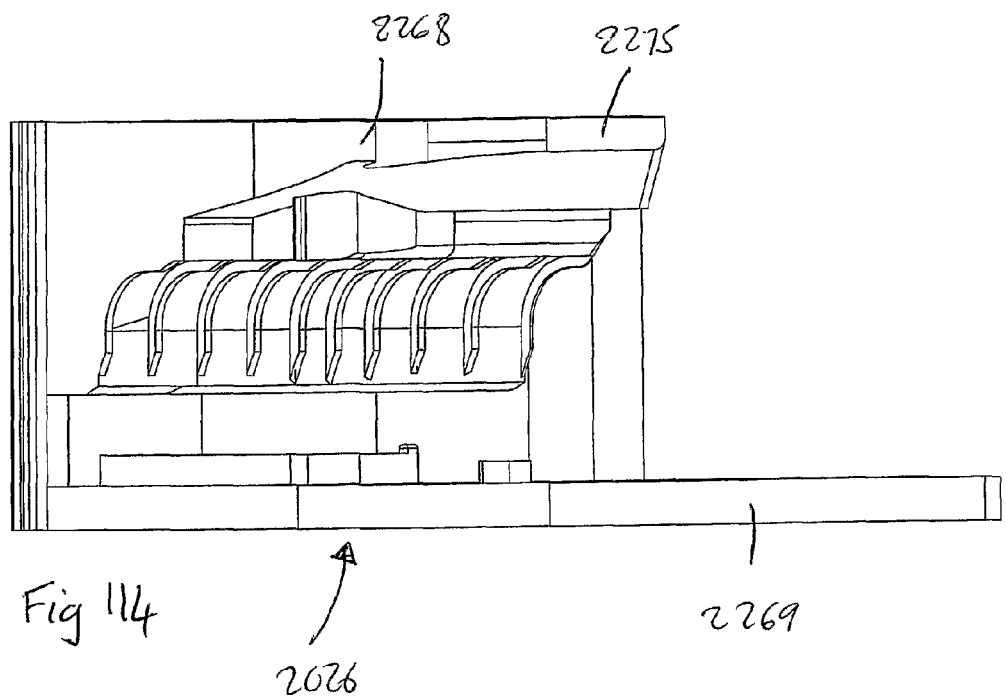
FIGS. 114 to 116 are perspective views of a movable element of the gripping portion of the embodiment of FIGS. 90 to 103, substantially from above the points of view of FIGS. 98, 99, and 100 respectively.
Figure 115:
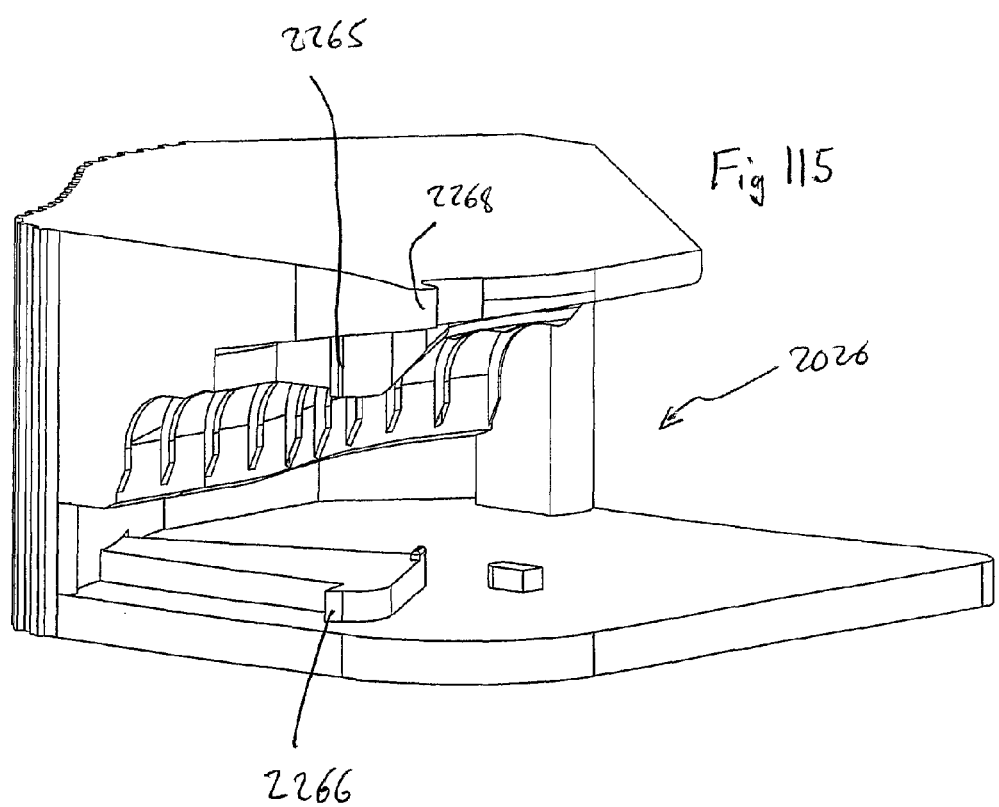
Figure 116:
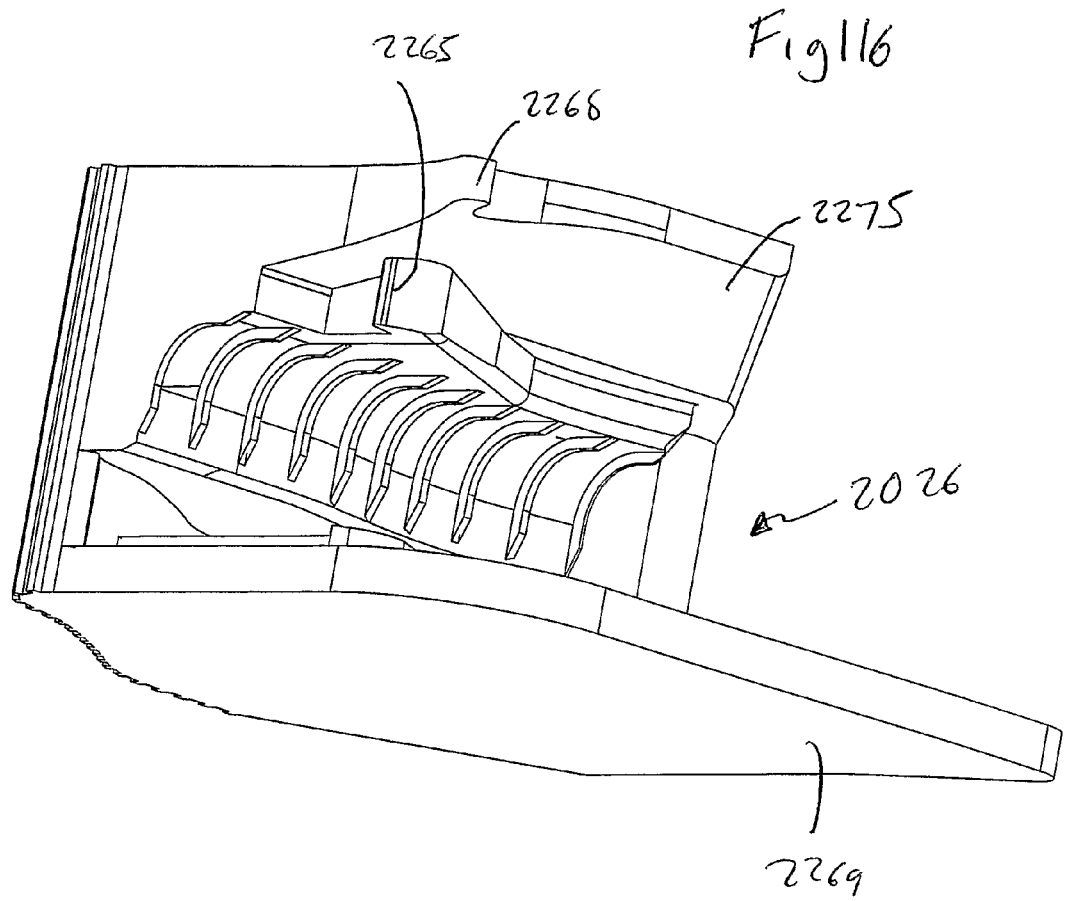
Figure 117:
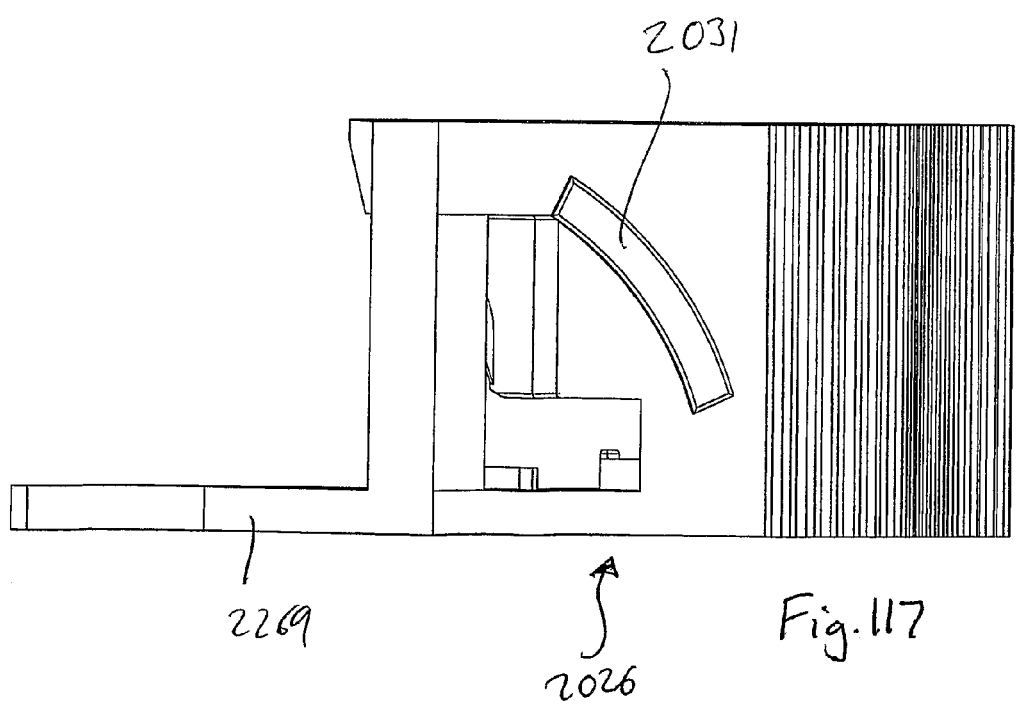
FIG. 117 is a view of the movable element of the gripping portion of the embodiment of FIGS. 90 to 103, substantially from above the point of view of FIG. 93.
Figure 118:
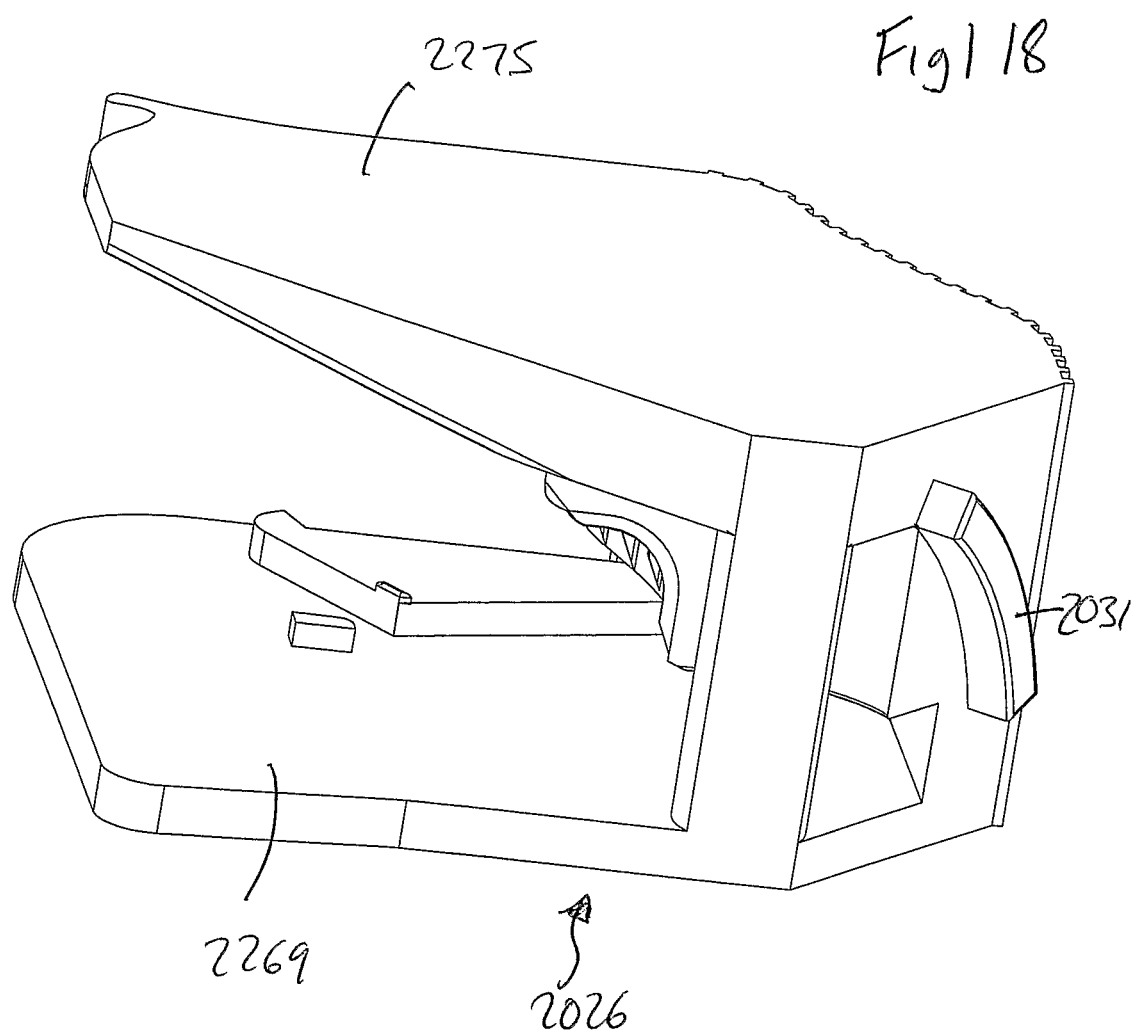
FIG. 118 is another perspective view from above of the movable element of FIGS. 114 to 117.
Figure 119:
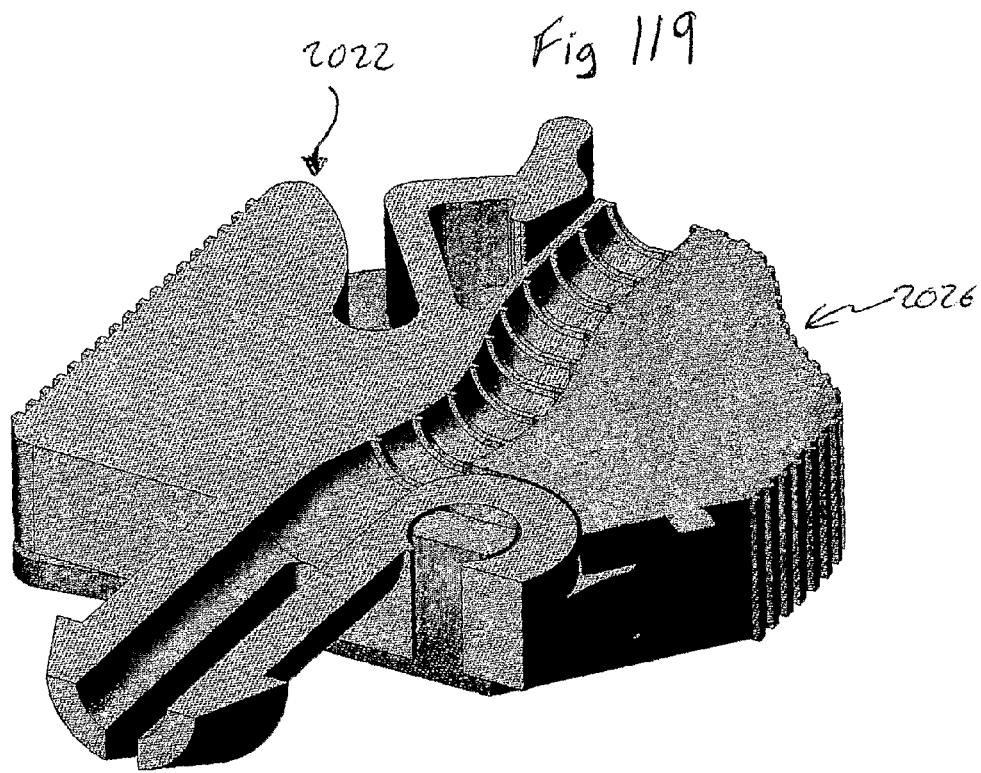
FIG. 119 is a horizontal cross sectional view showing the relative positions of two parts of the gripping portion of the attachment device of FIGS. 90 to 103 when the gripping portion is in its closed position.

Of course, it is important to avoid accidental opening of the gripping portion. For this reason a shield 2240 is provided to protect the first unlocking portion 2228. The shield 2240 is in the form of a part of the main body 2022 which shields the first unlocking portion 2228. In this embodiment, as best illustrated in FIG. 112, the shield 2240 extends rearward beyond the first unlocking portion 2228 so that a straight line (broken line X in FIG. 112) between the end of the tube accommodating passageway and the shield 2240 does not intersect the first unlocking portion 2228 (nor any other part of the gripping portion clasp mechanism). This ensures that even if the tube is pulled hard, and at an extreme angle relative to the device (ie so as to extend in a direction similar to the direction of the broken line X) the tube cannot contact or apply pressure to the first unlocking portion 2228. Without the shield 2240, it is possible that the tube might accidentally operate the unlocking mechanism.

Figure 102:
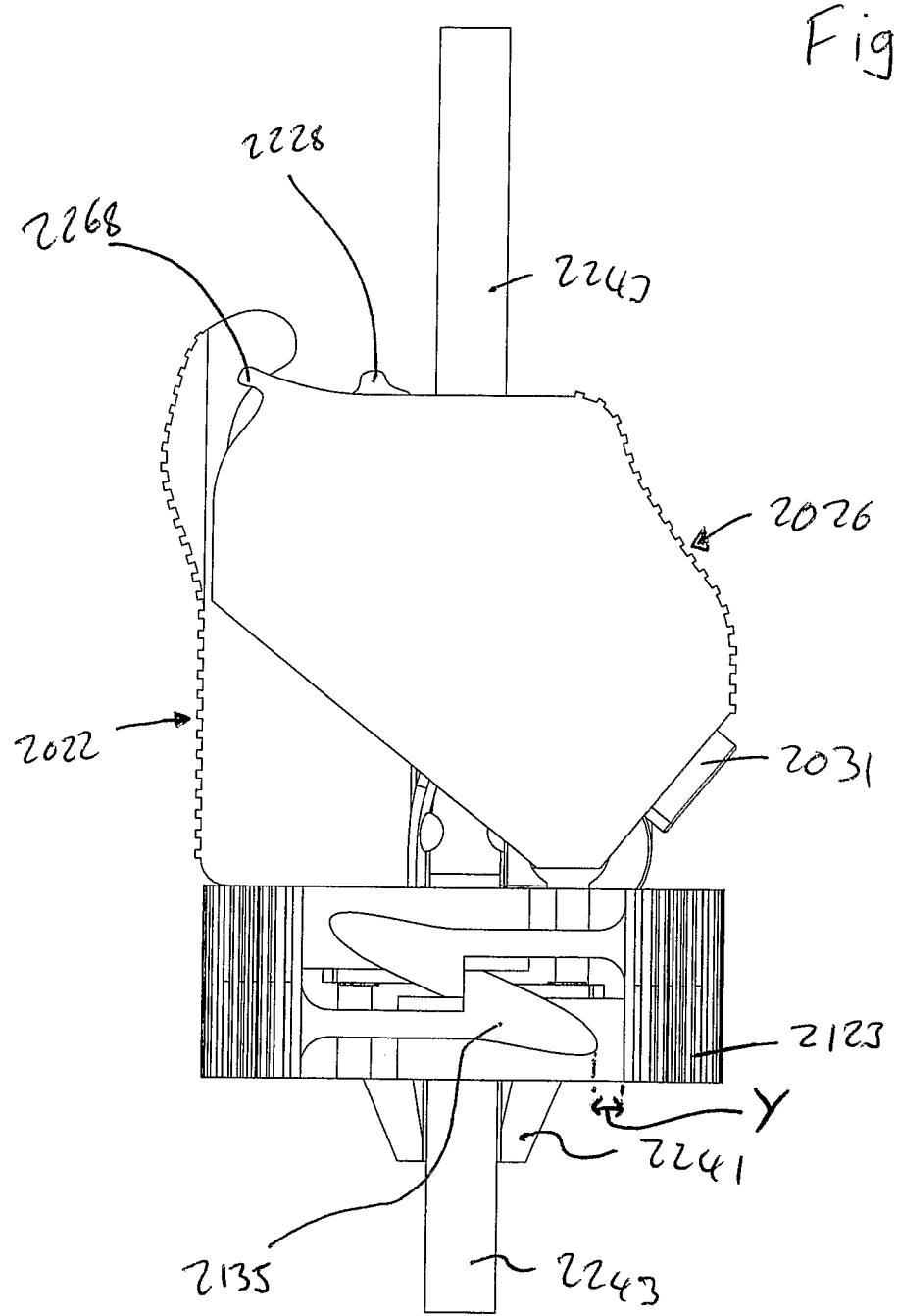
FIG. 102 is a plan view from above, corresponding to FIG. 101.
Figure 103:
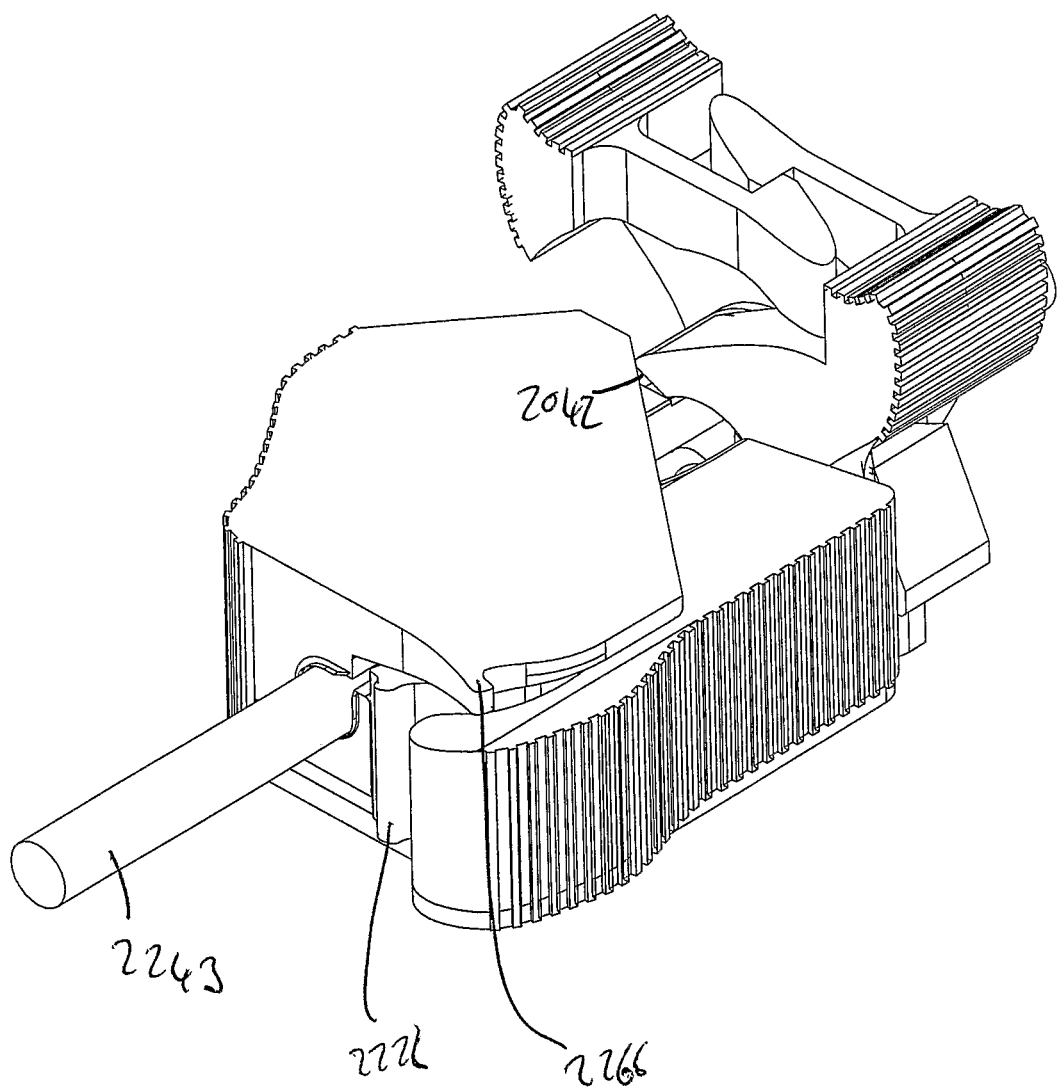
FIG. 103 is a perspective view from one end and above corresponding to FIGS. 101 and 102.

It is also important to avoid accidental opening of the clip portion 2010. The clasp part of the clip portion 2010 of the attachment device 2001 is designed to avoid inadvertent operation by the medical device tube being secured. In particular, inspection of, for example, FIG. 102 illustrates that the gap, designated Y in FIG. 102, between each clasping element 2135 and an adjacent operating portion 2123 of the clip portion 2010, is substantially smaller than the diameter of the tube 2243. Also, as is evident from, for example, FIG. 95, the clasping element 2135 does not project above the adjacent operating portion 2123 of the clip portion 2010. These precautionary features avoid the tube 2243 becoming caught in, or inadvertently operating, the clasp mechanism of the clip portion 2010.

Of course there are alternative means of reducing the likelihood of accidental opening of the gripping and/or clip portions and, in particular, of reducing the likelihood of accidental opening of the gripping and/or clip portions by interaction with the tube. For example, different clasping/locking mechanisms could be used which are more secure, but less easy to open (for example, requiring specific tools). In use, the attachment device will typically be covered by a dressing and/or adhesive tape or sheet, and the tube may also be taped to the patient close to the attachment device. This will help reduce the likelihood of accidental opening.

Attachment device 2001 differs from attachment device 1001 in that the passageway in which the tube is to be held is provided substantially in a plane which will be generally parallel to the skin, in use. The passageway includes one or more curved parts to enhance resistance to the tube being pulled axially from either end of the device. It is not considered necessary to have the passage inclined to direct the tube towards the skin at the rear of the attachment device 2001, since this embodiment already provides a lower profile for the tube than the attachment device 1001 by having the tube pass through, rather than over, the attachment element 2029.

Operation of the attachment device 2001 is similar to operation of the attachment device 1001, including the feature that the clip portion 2010 cannot be operated before the gripping portion 2020. If necessary the gripping portion 2020 can be re-opened after operation of the clip portion 2010 to allow further adjustment of the position of the tube.

In use, the tube is placed in a first channel portion 2220 of the main body 2022, where it is gently retained by preliminary gripping projections 2445 on the main body 2022 (which function analogously to the gripping projections 445 illustrated in FIG. 86) and allow gentle gripping of, for example, a catheter tube, prior to the secure gripping provided by closing the gripping portion 2020. The gripping portion 2020 is operated to secure the tube relative to the attachment device 2001, and the clip portion is then operated to secure the attachment device 2001 to the tissue of the patient.

Figure 120:
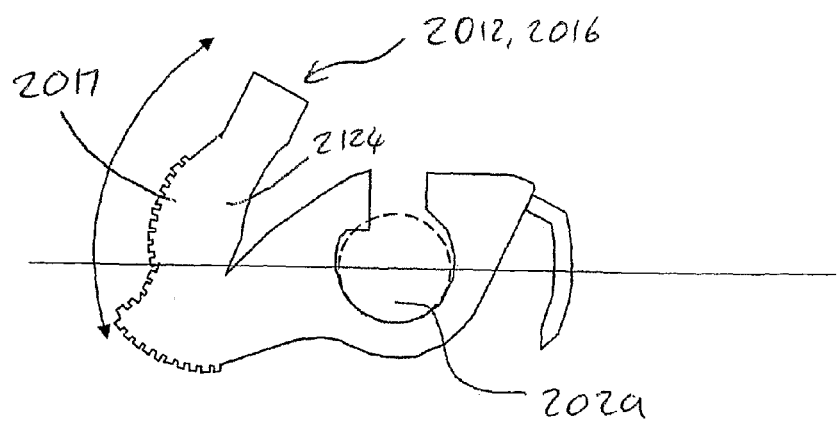
FIG. 120 is a schematic illustration of variation of the clip body of FIGS. 104 and 105.

One further variation which may beneficially be included in the attachment device 2001 is that, as illustrated in FIG. 120, the clip bodies 2012, 2016 may each be provided with a further operating portion 2017 located on the shank portion 2124. The further operating portion 2017 is located above the level (represented by the horizontal line in FIG. 120) of the centre of rotation of the clip body 2012, 2016. This facilitates operation of the clip portion 2010, which is effectively performed by pinching together the operating portions 2123 of the clip bodies, an operation which might be rendered less convenient if the operating portions of both clip bodies were below the level of the centre of rotation. This feature could, of course, be included in other embodiments if desired. It should be appreciated that in preferred embodiments the clip bodies are sufficiently small that no substantial repositioning of the fingertips would be required to complete the operation of closing the clip portion.

The preferred embodiments therefore provide an attachment device which can be used to secure an elongate object, and especially a tube such as a catheter tube or surgical drain tube to a patient in two simple clipping operations, each of which can essentially consist of pinching together two portions of the device with a thumb and forefinger. This allows rapid anchoring of tubes under stressful surgical conditions, potentially reducing ill effects on the patient which might otherwise occur due to delay in fixing the tube. A total operating time for operating the anchoring portion and the tube holding portion may be only a few seconds. The chance of needle stick injury to the medic anchoring the tube is also reduced compared to normal suturing methods of attachment. The anchoring of the tube is believed to be more secure and durable than methods relying solely on the use of adhesives. The position of the tube held by preferred devices may be adjusted in situ, and without detaching the attachment device from the patient, by opening the gripping portion, adjusting the position of the tube as required and re-closing the gripping portion. The main elements of the attachment device (except the prongs) can be injection moulded from a plastic.

Embodiments of the attachment device might be provided with apertures or shaped portions to facilitate additional fixing to the patient by suturing.

Modifications and improvements may be incorporated without departing from the scope of the present invention.

In the claims which follow and in the preceding description of the invention, except where the context requires otherwise due to express language or necessary implication, the word "comprise" or variations such as "comprises" or "comprising" is used in an inclusive sense, ie. to specify the presence of the stated features but not to preclude the presence or addition of further features in various embodiments of the invention.

The invention claimed is:

1. An attachment device for anchoring to tissue of a patient, the attachment device comprising:
   (a) at least one body element provided with a base surface for overlying and contacting said tissue, the body element comprising an elongated rod defining a rotation axis extending longitudinally through the rod; and
   (b) an anchoring portion mounted on the rod and comprising a pair of clip bodies being rotatable relative to the rod and one another around the rotation axis, wherein the anchoring portion comprises:
      (i) a first clip body comprising:
         a first mounting portion rotatably mounted on the rod, a first support portion extending radially outwardly from the first mounting portion, a first operating portion extending radially outwardly from the first mounting portion, and a first locking portion extending from the first operating portion;
         a first piercing member for anchoring the device by insertion of a first insertion portion, comprising at least a pointed end part of the first piercing member, into the tissue of a patient, the first piercing member being fixed relative to, and supported by, the first support portion;
      (ii) a second clip body comprising:
         a second mounting portion rotatably mounted on the rod, a second support portion extending radially outwardly from the second mounting portion, a second operating portion extending radially outwardly from the second mounting portion, and a second locking portion extending from the second operating portion, the second locking portion being complementary to the first locking portion;
         a second piercing member for anchoring the device by insertion of a second insertion portion, comprising at least a pointed end part of the second piercing member, into the tissue of a patient, the second piercing member being fixed relative to, and supported by, the second support portion;
      wherein the first and second mounting portions are rotatably mounted on the rod such that the first and second clip bodies are rotatable relative to each other around the rotation axis between an open position of the anchoring portion in which the anchoring portion is inoperative and a closed position of the anchoring portion for anchoring the device to the tissue of a patient, wherein the first and second clip bodies are configured such that rotating the first and second operating portions toward each other in opposite directions is effective to move the first and second clip bodies from the open position to the closed position;

wherein in the open position of the anchoring portion:
the first operating portion provides a first shielding portion which shields at least the pointed end part of the second piercing member against inadvertent contact with another object, and
the second operating portion provides a second shielding portion which shields at least the pointed end part of the first piercing member against inadvertent contact with another object; and
wherein in the closed position of the anchoring portion in use:
the first and second locking portions inter-lock with each other to resist rotation of the first and second clip bodies toward the open position;
wherein the first and second clip bodies are configured such that rotating the clip bodies from the open position to the closed position is effective to rotate the first and second piercing members in opposing directions away from the second and first shielding portions, respectively, toward each other until the piercing members are in contact with each other, and to rotate the first and second locking portions in opposing directions toward each other until the locking portions engage and inter-lock with each other.

2. The attachment device as claimed in claim 1, wherein there are two anchoring portions, each anchoring portion having first and second piercing members.

3. The attachment device as claimed in claim 1, wherein the attachment device comprises a limiting mechanism to limit relative rotation of the first and second clip bodies, relative to the at least one body element.

4. The attachment device as claimed in claim 3, wherein the body element is provided with a coupling member for receipt in, and coupling to, cavities in the first and second clip bodies, and wherein the coupling member is provided with a channel therein for accommodating an elongate object which it is desired to attach to a patient.

5. The attachment device as claimed in claim 1, wherein the first and second locking portions are substantially secure against manual unlocking without tools, and are adapted to be unlocked by insertion of a tool between the complementary first and second locking portions.

6. The attachment device as claimed in claim 1, wherein the attachment device comprises an anchoring portion retaining mechanism for retaining the anchoring portion in its open position, and wherein the anchoring portion retaining mechanism is adapted to prevent closure of the anchoring portion when a force less than a predetermined force is applied to close the anchoring portion of the device, but to allow closure of the anchoring portion when a force greater than a predetermined force is applied to close the anchoring portion of the device, and the predetermined force is of a magnitude that can be applied to the device by the grip of a finger and thumb by a single hand of a user.

7. The attachment device as claimed in claim 1, wherein the attachment device further comprises at least one restraining element adapted to prevent operation of the anchoring portion from its open position to its closed position.

8. The attachment device as claimed in claim 1, wherein the attachment device further comprises a holding part, for securely holding an elongate object to be secured to a patient in order to effect attachment of the elongate object to the attachment device.

9. The attachment device as claimed in claim 8, wherein the holding part comprises a first holding portion for engaging a first surface part of an elongate object and a second holding portion for engaging a second surface part of an elongate object, the first and second holding portions being mutually relatively movable, between an open position which allows removal of said elongate object and a closed position adapted to securely retain said elongate object.

10. The attachment device as claimed in claim 1, wherein said device is configured so that the anchoring portion is operable from its open position to its closed position by drawing together said first and second operating portions, by an operator engaging the first operating portion with a finger of one hand, engaging the second operating portion with a finger of the said hand, and drawing together the finger and a thumb in a pinching action.

11. The attachment device as claimed in claim 1, wherein:
the first support portion and the first operating portion are connected to the first mounting portion at respective locations that are angularly offset from each other around the rotation axis; and
the second support portion and the second operating portion are connected to the second mounting portion at respective locations that are angularly offset from each other around the rotation axis.

12. The attachment device as claimed in claim 11, wherein:
the first support portion and the first operating portion are connected to the first mounting portion at diametrically opposed locations; and
the second support portion and the second operating portion are connected to the second mounting portion at diametrically opposed locations.

* * * * *